United States Patent [19]
Williamson, IV et al.

[11] Patent Number: 6,042,607
[45] Date of Patent: *Mar. 28, 2000

[54] MEANS AND METHOD OF REPLACING A HEART VALVE IN A MINIMALLY INVASIVE MANNER

[75] Inventors: Warren Williamson, IV, Loveland, Ohio; Paul A. Spence, Louisville, Ky.; George T. Christakis, Toronto, Canada; Thomas J. Ward, Grandview Heights, Ohio; Dominic P. DiNovo, Columbus, Ohio; George A. Keller, Grandview Heights, Ohio; Cecil R. Robinson, Hilliard, Ohio; E. Dale VanHoose, Columbus, Ohio

[73] Assignee: CardioVascular Technologies LLC, Loveland, Ohio

[ * ] Notice: This patent is subject to a terminal disclaimer.

[21] Appl. No.: 08/802,948

[22] Filed: Feb. 21, 1997

Related U.S. Application Data

[63] Continuation-in-part of application No. 08/606,343, Feb. 23, 1996, Pat. No. 5,716,370.

[51] Int. Cl.[7] .......................................................... A61F 2/24
[52] U.S. Cl. ................................. 623/2; 623/11; 606/153; 606/151
[58] Field of Search .......................... 623/2, 11; 606/149, 606/150, 151, 153

[56] References Cited

U.S. PATENT DOCUMENTS

| 3,657,744 | 4/1972 | Ersek ....................................... 606/153 |
| 5,250,058 | 10/1993 | Miller et al. .............................. 606/153 |
| 5,261,920 | 11/1993 | Main et al. ................................ 606/153 |
| 5,554,162 | 9/1996 | DeLange .................................. 606/153 |
| 5,571,116 | 11/1996 | Bolanos et al. ........................... 606/151 |
| 5,593,424 | 1/1997 | Northrup, III ............................ 606/232 |
| 5,669,918 | 9/1997 | Balazs et al. ............................. 606/153 |
| 5,707,380 | 1/1998 | Hinchliffe et al. ........................ 606/153 |
| 5,716,370 | 2/1998 | Williamson, IV et al. ............... 606/153 |
| 5,720,755 | 2/1998 | Dakov ...................................... 606/153 |
| 5,733,331 | 3/1998 | Peredo ......................................... 623/2 |
| 5,817,113 | 10/1998 | Gifford, III et al. ...................... 606/153 |
| 5,893,886 | 4/1999 | Zegdi et al. ................................. 623/1 |
| 5,895,419 | 4/1999 | Tweden et al. .............................. 623/2 |

*Primary Examiner*—Paul B. Prebilic
*Attorney, Agent, or Firm*—Terry M Gernstein

[57] ABSTRACT

A heart valve can be replaced using minimally invasive methods which include a sutureless sewing cuff that and a fastener delivery tool that holds the cuff against the patient's tissue while delivering fasteners, two at a time to attach the cuff to the tissue from the inside out. The tool stores a plurality of fasteners. Drawstrings are operated from outside the patient's body and cinch the sewing cuff to the valve body. The cuff is releasably mounted on the tool and the tool holds the cuff against tissue and drives the fastener through the cuff and the tissue before folding over the legs of the fastener whereby secure securement between the cuff and the tissue is assured. At least two rows of staggered fasteners are formed whereby fasteners are located continuously throughout the entire circumference of the cuff. A minimally invasive surgical method is disclosed, and a method and tool are disclosed for repairing abdominal aortic aneurysms in a minimally invasive manner.

104 Claims, 41 Drawing Sheets

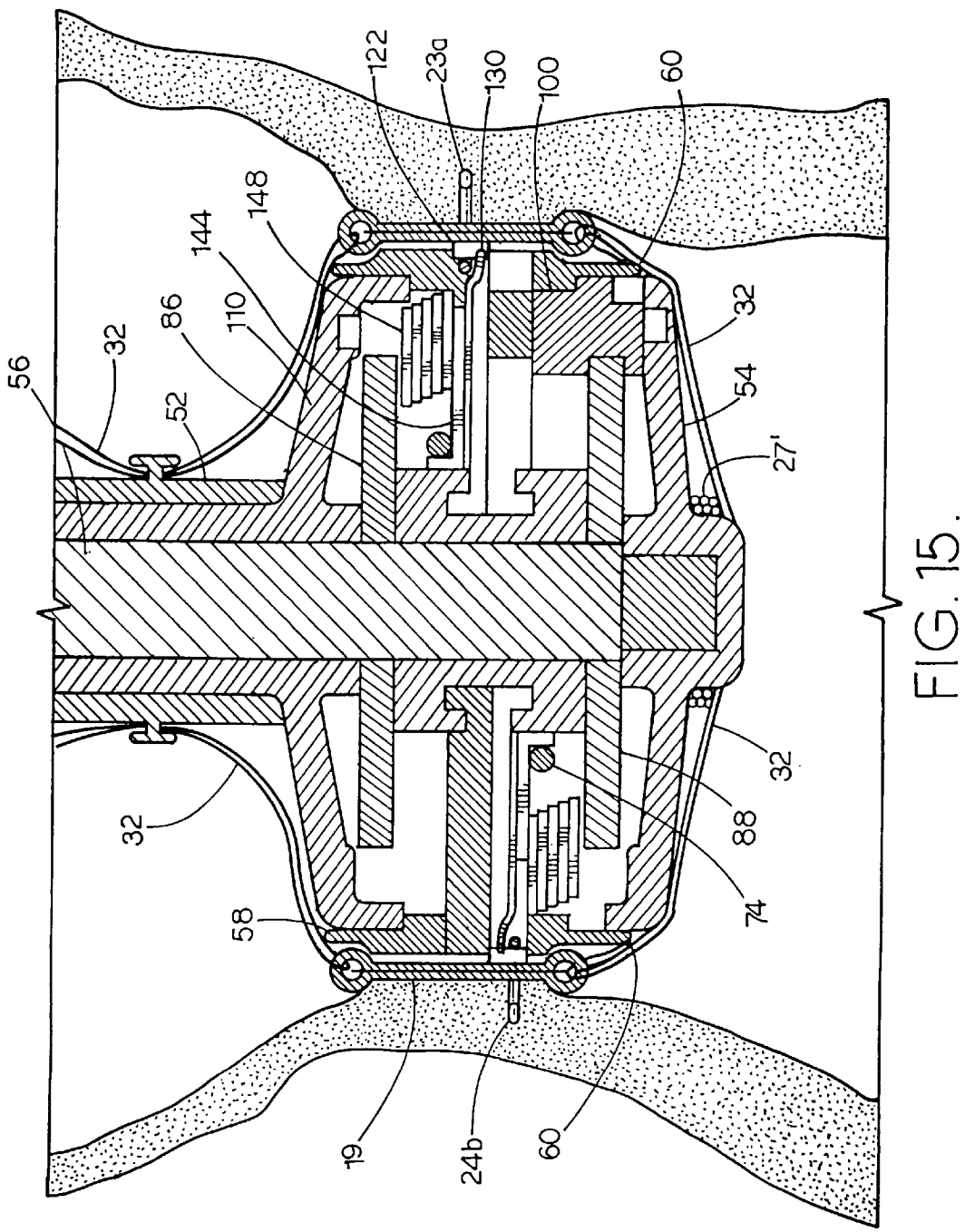

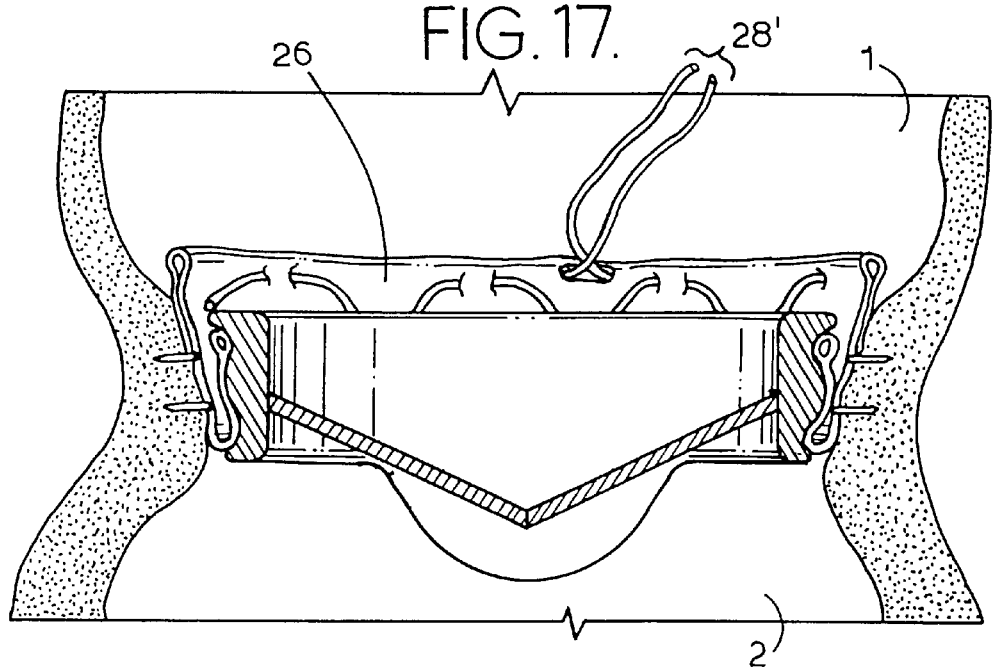
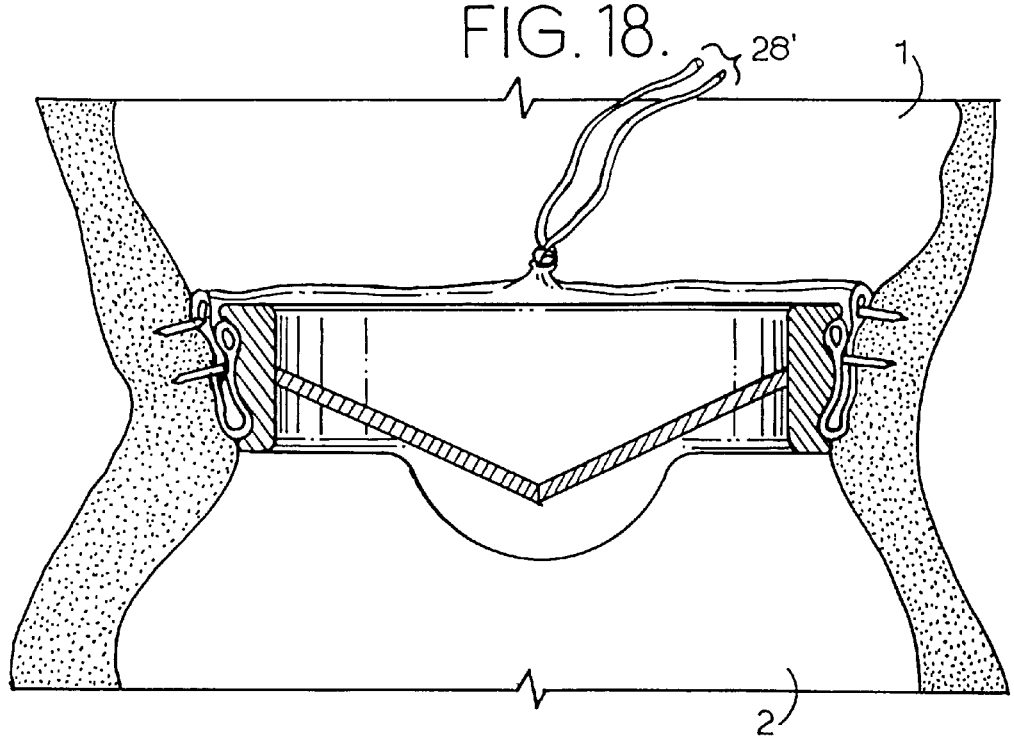

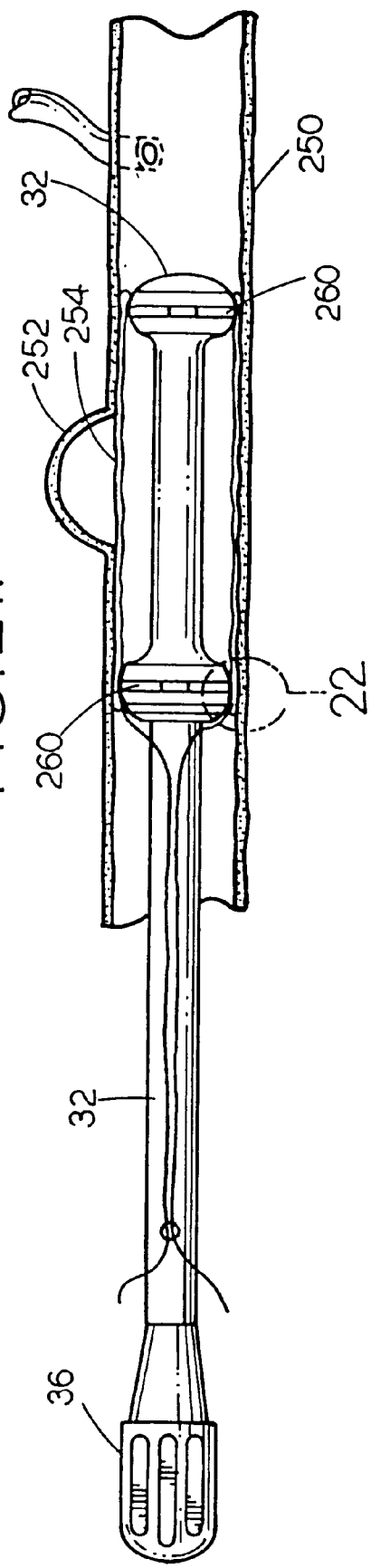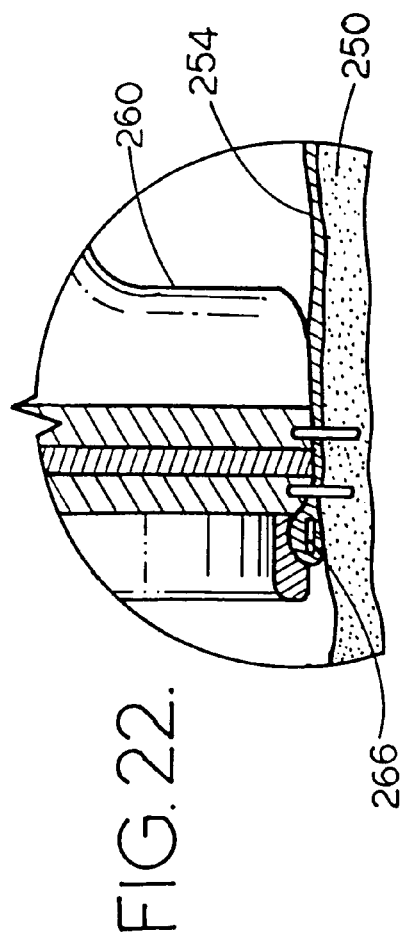

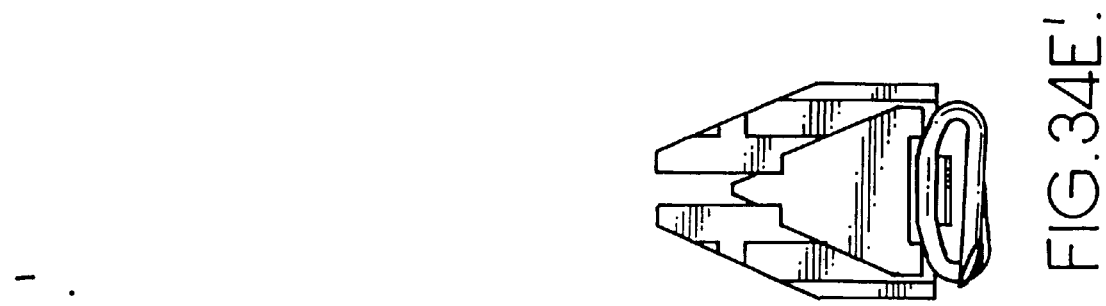
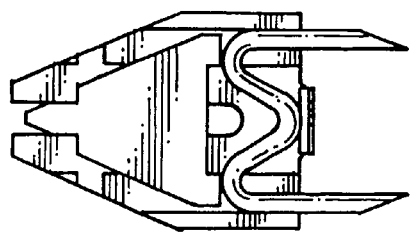
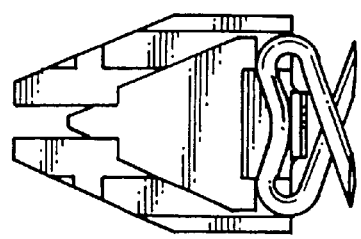
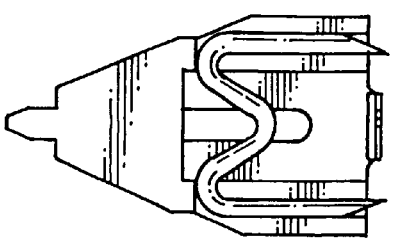
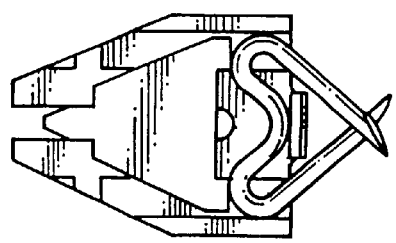

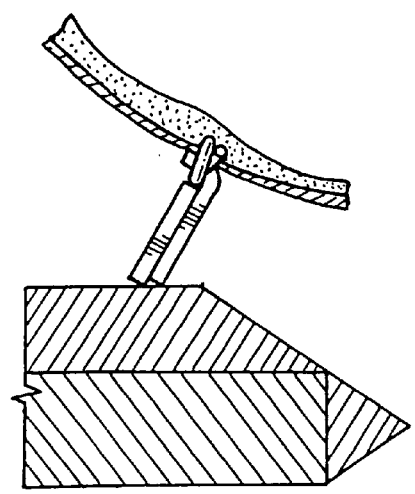
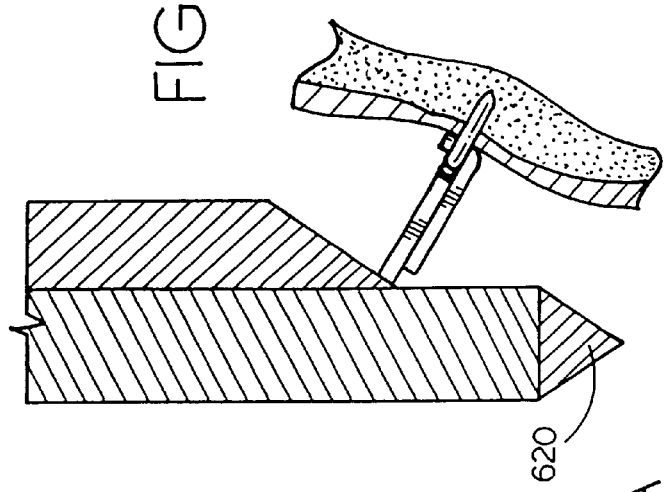
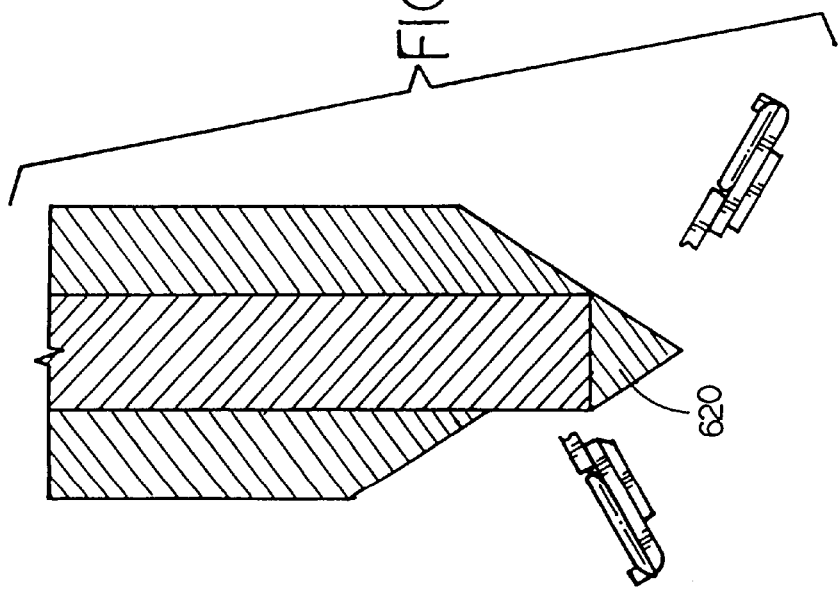

MEANS AND METHOD OF REPLACING A HEART VALVE IN A MINIMALLY INVASIVE MANNER

This application is a continuation-in-part of U.S. Ser. No. 08/606,343 filed Feb. 23, 1996 which is now U.S. Pat. No. 5,716,370.

TECHNICAL FIELD OF THE INVENTION

The present invention relates to the general art of prosthetic devices, and to the particular field of prosthetic heart valves and surgical tools and techniques associated therewith.

BACKGROUND OF THE INVENTION

It is well known that heart diseases may result in disorders of the cardiac valves. For example, diseases such as rheumatic fever can cause the shrinking or pulling apart of the valve orifice, while other diseases may result in endocarditis, an inflammation of the endocardium or lining membrane of the heart. The resulting defects in the valves hinder the normal functioning of the atrioventricular orifices and operation of the heart. More specifically, defects such as the narrowing of the valve stenosis and/or the defective closing of the valve, referred to as valvular insufficiency, result in an accumulation of blood in a heart cavity or regurgitation of blood past the valve. If uncorrected, prolonged valvular stenosis or insufficiency may cause damage to the heart muscle, which may eventually necessitate total valve replacement.

These defects may be associated with any of the cardiac valves. For example, if the mitral valve stenosis connecting the left auricle with the left ventricle narrows, blood will accumulate in the left auricle. Similarly, in the case of mitral insufficiency, the mitral valve does not close perfectly, and blood in the left ventricle is regurgitated past the closed mitral valve into the left auricle when the ventricle closes.

In many cases, complete valve replacement is required. Mechanical artificial heart valves for humans are frequently fabricated from titanium, prolitic carbon or tissue, including tissue from cows, pigs or humans. Such valves have been used because of their nonthrombogenic properties. Human blood does not coagulate on contact with such valves. Moreover, they are lightweight, hard and quite strong. Therefore, such valves have become widely accepted and used by many surgeons. Any new prosthetic valve or surgical technique associated therewith should account for this. One popular prosthetic valve includes such a hard body and a knit fabric sewing or suture cuff fixedly attached thereto as by drawstrings made of plastics-type material. The sewing cuff is sutured in place on the patient's tissue, and that tissue grows into the fabric providing a secure seal for the prosthetic valve. As will be discussed below, even though this is a widely accepted valve, there are problems and drawbacks.

A standard implantable mechanical heart valve usually has an annular valve housing or body to provide a passageway for blood. Occulders are mounted in the annular body and open or close the blood flow passageway. Usually there are one or two occulders, but occasionally triple occulder configurations have been proposed. On the outside of the valve body there is usually an external, circumferential surface configured as a groove. The purpose of this groove is to facilitate attachment of the above-discussed suture ring to the valve body.

As above mentioned, replacement of heart valves has become a widely accepted procedure. Currently, as many as eighty thousand heart valve prostheses are implanted in the United States alone. This procedure is very expensive. It requires the talents of a highly skilled surgeon, perfusionist and anesthesiologist as well as the supporting staff and equipment required to keep the patient on a heart/lung bypass machine during the operation. While this procedure currently works very well, operating time is still extensive and the longer the patient is on bypass equipment, the greater the risk to the patient. Furthermore, hand suturing is tedious and time consuming further lengthening the time the patient is on cardiopulmonary bypass and hypothermia. This may increase the chances of tissue damage to the patient.

Therefore, there is a need for a heart valve replacement procedure that reduces the surgical time required for the operation.

Still further, many currently used surgical techniques are invasive and often require breaking of bones. This increases the time and difficulty of the recovery. Therefore, there is a need to develop a prosthetic heart valve and a procedure for implanting same that reduces the invasiveness of this surgery.

As above mentioned, hand suturing of prosthetic heart valves in place is widely accepted. However, this requires the opening of the patient's chest wall to gain access to the aortic valve through a transverse incision in the ascending aorta. The distance from the incision down to the valve is usually two to two and one halve centimeters with an aortic lumen diameter of between seventeen and thirty millimeters. This creates a very long and narrow tube into which the surgeon must place sutures. While this is a tedious procedure in an "open chest" case, it is very challenging to accomplish through any small incision between the ribs or through a thoracic inlet, as would be required in any minimally invasive procedure. Therefore there is a need for a device and method that can secure the valve remotely from outside the chest wall.

A further problem associated with suturing some prostheses is that the valve is bulky and reduces the inside diameter of the valve body. A reduced inside diameter of the valve reduces the flow area of the valve resulting in increased transvalvular pressure gradients resulting in increased work for the heart muscle. A reduced flow area for such a valve may adversely influence blood flow characteristics associated with the valve, thereby adversely influencing the performance of the valve. This is very counter-productive to the clinical needs of the prosthesis. It is very hard to develop a mechanical valve that has the same flow characteristics of a living tissue valve. This is especially so of many existing multi-part prostheses. Even the so-called sutureless valves that have been disclosed in the art may have this problem. Heart valve designs have been directed toward minimizing the back pressure or restriction of forward flow by maximizing the cross-sectional area of the valve within a given outer diameter base. Housing attachment means within the valve base narrows the inside diameter of the valve body thereby creating adverse flow characteristics. Therefore, there is a need for a prosthetic valve which has the flow area thereof maximized. Reduced flow area may also result in rapid blood acceleration with a concomitant risk of red cell hemolysis and activation of sensitive enzyme systems such as the clotting system.

Yet a further problem with some prosthetic heart valves and the implanting procedures associated therewith, is that there are unwanted projections remaining on the implanted valve. This is especially so for valves that are sutured in place. Blood clots tend to form around foreign objects in the body. The body's natural defenses try to seal off any foreign material and make it non-threatening. However, there is a danger that the formed blood clots may dislodge into the patient's blood stream, which may cause a major problem.

The sutures used in many existing techniques to sew a cuff in place are knotted and cut off. This leaves raw edges exposed to the patient's blood stream. These raw edges of the cut off suture and knot provide surfaces for clot formation and provide potential for clots to break off into the bloodstream as they are newly formed. Loose clots in the bloodstream are dangerous for the patient as they have the potential for producing a stroke. Clots forming on sutures may also extend onto the valve and produce malfunctions by trapping the valve open or shut. It is common practice to treat a post-surgical patient with heparin or some other anticoagulant to minimize the production of clots. Therefore, there is a need for a prosthetic valve and surgical implanting process that minimizes the amount of foreign objects that remain exposed to the patient after the valve has been implanted. The exposed surfaces may also become a site of infection. Circulating bacteria may become attached and lead to infection at the valve. These infections are notoriously difficult to treat with antibiotics.

Yet another problem arises because it is difficult to effect a secure fit between the prosthesis and the patient's tissue. If there are gaps between the lumen and the valve, a leak may develop causing blood to bypass the valve. This can cause disastrous problems. Additionally, in many of the prostheses that are disclosed in the prior art as being sutureless, there is no way to ensure close approximation of the aortic lumen to the valve base prior to setting fasteners. This has allowed the lumen to pull away from the base and create the just-mentioned leak-generated problems. This is because anatomy is different from patient to patient. It is impossible to make the entire spectrum of valve bases to accommodate such differences in anatomy as would be required by some of the systems presently in use. Additionally, differences in diameter are not just in diameter of the lumen, but in the irregularities of the annulus where the valve is to be placed. Still further, disease and calcification can make the placement of known valves unmanageable. Whatever the cause of the imperfect fit between the prosthetic valve and the lumen, the variation in opening size and/or shape must be accounted for in placing the prosthesis. A securely anchored and tightly fit prosthesis is necessary for a successful outcome.

Furthermore, an improper fit between the prosthetic device and the lumen may greatly increase the duration of the operation or require corrective surgery to replace an improperly placed prosthesis.

Therefore, there is a need for a prosthesis valve that can be securely fit to a patient's lumen in an expeditious and reliable manner.

While the art contains several teachings which could be applied to one or more of the above-mentioned problems, such as the above-discussed cuffs, these disclosures have several drawbacks which are in addition to those already mentioned. For example, these prosthetic valves generally include a sewing ring or suture cuff that has some sort of stiffener therein. An example of such a stiffener is soft plastic. Plastic, even easily molded plastic, may require the patient's tissue to be severely handled and still have puckering even after great precautions have been taken. In this situation, stiffening elements may be more difficult to handle than fully flexible elements and may adversely affect the patient's tissue. Therefore, any new prosthesis valve should use a fully flexible material to attach that prosthesis to the patient to avoid the problems of unduly stressing the patient's tissue during the placement of the valve.

Dacron, Polyester and Teflon have been a very popular material for sewing cuffs. It is slightly stretchable, allowing it to be dilated. Needles readily pass through it without tearing or snagging the fabric fibers and the Dacron material has exceptional implant qualities with a proven track record of bioacceptance that allows ingrowth of endothelial cells. Due to its wide acceptance, it will be commercially advantageous to incorporate Dacron into any new prosthesis valve.

Therefore, there is a need for a prosthesis heart valve which can be tightly placed in a patient without requiring undue stressing of the patient's tissue.

There is yet additional need for a prosthesis heart valve which can have its size and shape expeditiously adjusted to produce a secure, non-leaking, fit to the particular patient, again without placing undue stress on the patient's tissue.

Still further, it is highly desirable for the surgeon to be able to adjust the orientation of the valve in situ. This will permit the prosthesis to be customized to the particular patient. While many known valves can be moved in place, there is still need for improvement in the ease and accuracy of such a step.

Still further, because the position of the junction between the coronary arteries and the aorta is variable, the choice of the location of the placement of the prosthesis should be as great as possible. The high profile of many of the finished sewing cuffs of the known devices severely limits this choice.

Still further, in many instances, it is advantageous for the surgeon to move the prosthesis into various positions relative to the sewing cuff. This will allow the valve to sit at the same level, above or below a certain level. For example, it might be advantageous to seat the valve cuff to be seated above the annulus to maximize the effective orifice area. It will be advantageous to be able to place the prosthesis in the most superior position without interference with the coronary arteries thereby allowing a larger diameter prosthesis to be placed. A lower profile cuff allows the surgeon to place the prosthesis as high as possible without interfering with the coronary artery junction.

Therefore, there is a need for a prosthetic heart valve that has a low profile finished cuff whereby the surgeon can have a greater choice in the superior/inferior placement of the prosthesis valve.

Current prosthetic valves are inefficient because the sewing cuff occupies part of the area available for flow through the valve. If a very small prosthesis is placed in the annulus, there can be a mismatch between the patient's cardiopulmonary requirements and the flow area of the valve. If a patient demands a high level of flow due to a larger size, a small sized valve may result in a significant transvalvular gradient. That is, the pressure in the left ventricle is considerably higher than the pressure in the aorta. This results in increased work for the left ventricular muscle and may predispose to myocardial failure.

If the surgeon suspects that the prosthesis placed is going to be too small, he may elect to enlarge the aortic root. Presently, this is accomplished by opening the aortic annulus opened perpendicular to the plane of the annulus in continuity to the aortomy. The incision is extended along the anterior leaflet of the mitral valve for a varying length. A patch of tissue or fabric material is then stitched to this incision to enlarge it. The procedure allows the insertion of a larger prosthesis into the newly enlarged annulus. However, there is an increased risk to the patient, principally because of the risk of bleeding from the suture line. This site is virtually inaccessible to repair after the aorta is closed.

Therefore, there is a need for a simpler way to expand the aortic annulus. Dilation is preferred, and thus, there is a further need to be able to expand the aortic annulus by dilation. Still further, in minimally invasive surgery, it is sometimes difficult to gain access to a proper fastening plane with a straight instrument. Therefore, it is desirable to be able to use an articulated or curved shaft for a fastening or stapling instrument. Still further, it is often desirable to be able to manipulate the fastening instrument into the most advantageous orientation with respect to the area being stapled.

Therefore, there is a need for a fastening instrument that can be operated to gain access to a great number of fastening planes.

Still further, it is often desirable to stretch and manipulate an element prior to fastening that element to the patient. This is not always possible in minimally invasive techniques using instruments that are available prior to the instruments disclosed herein. Therefore, there is a need for an instrument that can stretch and shape a flexible element prior to and during fastening of that element to a patient in a minimally invasive procedure.

Still further, tough tissue, calcium deposits and the like make fastening an element to a patient difficult, especially in the context of a minimally invasive technique. Therefore, there is need for an instrument that can force a staple through tough tissue and/or calcium covered tissue in a minimally invasive technique. This should be achieved without bunching or damaging the tissue or the element being stapled.

Often, in minimally invasive surgery, it is difficult to place staples in precisely proper locations. This is especially true if the staples are being placed in a circular pattern. Since the circumference of a circle is often not evenly divisible by the width of a staple the gaps between staples are often difficult to establish with proper accuracy so gaps in the staple coverage or bunching of either tissue or material is avoided.

Therefore, there is a need for a device that can be used in minimally invasive surgery for properly placing staples.

Staple placement can be effected by manually locating the staple delivery assembly or by automatically locating the staple delivery assembly. If a manual location technique is used, it is desirable that the surgeon be given an opportunity to choose between a manufacturer's suggestion and his own assessment of the situation. Therefore there is a need for a stapling device for use in minimally invasive surgery that will allow a surgeon to manually locate staples or to select a suggested location for the staples.

As above discussed, the placement of staples in a minimally invasive situation may be difficult to effect in an even manner. Therefore, there is a need for a means and a method for placing staples in a pattern wherein the spacing of the staples is even and no overlap or unwanted gaps occur even if an aorta or other such organ being stapled is an "off size." bbb Still further, it is desirable that a staple used in a minimally invasive surgical technique drive through the tissue and the material being attached to the tissue in a manner that is most effective. Thus, no bunching or gaping should occur, even if the tissue is tough. The effort to drive the staple through the tissue should be minimized if possible since the mechanical advantage is not the most effective in many situations.

Therefore, there is a need for a staple that can be used in a minimally invasive surgical technique that can be driven through tough tissue in an effective manner.

Still further, there is a need to close the aortomy after completion of valve replacement surgery. This is now achieved using sutures. However, this is time consuming. Therefore, there is a need for a means and a method for closing the aortomy in an efficient and effective manner.

OBJECTS OF THE INVENTION

It is a main object of the present invention is to provide a prosthesis heart valve which can be implanted in a surgical procedure that is minimally invasive.

It is another object of the present invention to provide a prosthesis heart valve that can be implanted in an expeditious surgical procedure.

It is another object of the present invention to provide a prosthesis heart valve that can present the largest possible flow area to the patient.

It is another object of the present invention to provide a prosthesis heart valve that reduces the number of objects exposed to the patient after implantation.

It is another object of the present invention to provide a prosthesis heart valve which can be customized to the particular patient without placing undue stress on the patient's tissue.

It is another object of the present invention to provide a prosthesis heart valve which can utilize widely accepted materials while still realizing the advantages set forth herein.

It is another object of the present invention to provide a prosthesis heart valve which utilizes a fully flexible sewing cuff.

It is another object of the present invention to provide a prosthesis heart valve which can use a Dacron sewing cuff.

It is another object of the present invention to provide a prosthesis heart valve which has a finished cuff that has a low profile above the valve.

It is another object of the present invention to provide a prosthesis heart valve which eliminates suturing as a means for attaching the prosthetic device to the patient.

It is another object of the present invention to provide a surgical technique associated with the implanting of a prosthesis heart valve which is minimally invasive.

It is another object of the present invention to provide a surgical technique associated with the implanting of a prosthesis heart valve which is minimally invasive yet which is accurate, expeditious and results in a firmly, accurately and fixedly placed prosthetic device.

It is another object of the present invention to provide a surgical technique associated with the implanting of a prosthesis heart valve which reduces the amount of stress that is placed on the patient's tissue during the placement procedure.

It is another object of the present invention to provide a surgical technique associated with the implanting of a prosthesis heart valve which does not require opening the patient's chest wall.

It is another object of the present invention to provide a surgical technique associated with the implanting of a prosthesis heart valve which attaches the prosthesis valve with fasteners that are hidden inside the device whereby the chances of infection and thrombosis are significantly reduced.

It is a specific object of the present invention to provide a surgical technique associated with the implanting of a prosthesis heart valve which hides the fasteners inside the sewing cuff.

It is a specific object of the present invention to provide a surgical technique associated with the implanting of a prosthesis heart valve which significantly reduces the chances of the cuff puckering during the implanting procedure.

It is another specific object of the present invention to provide a surgical technique associated with the implanting of a prosthesis heart valve which dilates the graft or cuff and the lumen together to provide intimate contact during the fastening procedure.

It is another object of the present invention to provide a surgical technique associated with the implanting of a prosthesis heart valve which allows for endoscopic visualization of the placement of the valve in the heart.

It is another object of the present invention to provide a surgical technique associated with the implanting of a prosthesis heart valve which permits both dilation and placement of fasteners in a sewing ring or graft.

It is another object of the present invention to provide a surgical technique associated with the implanting of a prosthesis heart valve which assures secure attachment of the prosthetic device to the patient.

It is another object of the present invention to permit a surgeon to use a larger valve if such larger valve is indicated.

It is another object of the present invention to provide a means and method wherein the annulus of the aorta can be stretched as a prosthetic valve is being placed.

It is another object of the present invention to allow insertion of a larger prosthesis without opening the annulus and adding a patch.

It is another object of the present invention to provide a means and a method whereby annuloplasty can be performed.

It is another object of the present invention to provide a device that will allow the addition of standard sutures to repair or reinforce any area of potentially weak attachment of the suture ring to the annulus.

It is another object of the present invention to provide a means and a method for minimally invasive surgery which can gain access to a proper fastening plane.

It is another object of the present invention to provide a means and a method for minimally invasive surgery is able to manipulate the fastening instrument into the most advantageous orientation with respect to the area being stapled.

It is another object of the present invention to provide a means and a method for minimally invasive surgery which can stretch and manipulate an element prior to fastening that element to the patient.

It is another object of the present invention to provide a means and a method for minimally invasive surgery that can force a staple through tough tissue and/or calcium covered tissue in a minimally invasive technique without bunching or damaging the tissue or the element being stapled.

It is another object of the present invention to provide a means and a method for minimally invasive surgery for properly placing staples.

It is another object of the present invention to provide a means and a method for minimally invasive surgery that will allow a surgeon to manually locate staples or to select a suggested location for the staples.

It is another object of the present invention to provide a means and a method for minimally invasive surgery that includes a staple that can be used in a minimally invasive surgical technique that can be driven through tough tissue in an effective manner.

It is another object of the present invention to provide a means and a method for minimally invasive surgery for closing an aortomy in an efficient and effective manner.

SUMMARY OF THE INVENTION

These, and other, objects are achieved by a sutureless prosthetic heart valve or graft which has a flexible sewing cuff stapled in place prior to placement of the heart valve body. The objects are also achieved by a tool and a surgical procedure for effecting placement of the prosthetic valve in a minimally invasive manner.

More specifically, the prosthetic valve includes a flexible sewing cuff, such as Dacron, or the like, which is stapled to heart tissue using a special tool that is inserted into the patient via an incision located in the thorax, either via a retrostenal approach or by removal or separation of the ribs. The tool releasably carries the cuff and includes means for continuously pressing the flexible cuff against the patient's tissue during the stapling procedure. By using a special non-gathering staple, puckering is essentially eliminated.

The cuff is attached to the valve body using drawstrings which extend outside the patient's body. The valve body is positioned in the in-situ cuff and the drawstrings are operated. Because the cuff is flexible, stretching of the tissue is minimized since inaccuracies are, at least, partially, absorbed by the flexible cuff.

The system disclosed herein should have improved blood flow and biological acceptance in the patient because suture knots and felt pledgets are not used. This provides additional advantages to use of this system due to a potentially reduced risk of stroke and infection post-surgery and potential for use of lower doses of anticoagulant and antibiotics post surgery.

Still further, due to the minimally invasive nature of the procedure, there is a possibility of applying the teachings of this invention to emergency procedures that may be performed outside of an operating room environment.

Yet another advantage of the present system is the low profile of the finished cuff above the valve base. This allows the surgeon greater choice in the superior/inferior placement of the valve. This is important because the position where the coronary arteries join the aorta is extremely variable. The low profile of the cuff allows for more distance between the cuff and the coronary junction.

Because the cuff of the present device is formed of material that has already been successful and is widely accepted, the commercial advantages associated with this device are enhanced.

Due to the surgical techniques that can be utilized with the present invention, it is possible to use video appliances, such as miniature video endoscopes.

The presently disclosed means and method can be used to perform annuloplasty where the cuff is fastened to an aorta above a leaky but salvageable human tricuspid valve. A ring is then inserted into the cuff to size the annulus and impart a compressive force on the valve causing the leaflets to close more securely. The ring could be malleable metal or plastic to allow the surgeon to shape it correctly to impart forces in right area. This could be applied to mitral and other locations as well.

The placed cuff can be inspected by the surgeon to be sure that it is placed securely. If the surgeon decides that hand-placed sutures will be helpful, he can place such sutures as needed.

If desirable, the surgeon can use a staple delivery mechanism to place staples either according to a prescribed path or according to his best judgement at the time. The hereinbelow disclosed device includes a staple delivery instrument that can be used to place staples one at a time along a predetermined path, or in conjunction with a guide, automatically along a helical path. The helical path will place staples in a desired spacing and can be used with staples of different widths. The advantage of a helical path is that it can accommodate many different saple widths and placements inot the same path. By simply adding one or more staples at the end of the helical path, different staple widths and placements can be accommodated.

Still further, the device disclosed herein can be used to close an aortomy. If desired, a surgeon can use the staple delivery device to place staples along a path set by icons until he becomes more confident in an automatic placement technique. The instrument saves time in placing staples.

Yet another form of the stapling instrument delivers staples in staggered rows while being able to engage a cuff to force and stretch that cuff against the patient's tissue to ensure proper placement of the cuff.

BRIEF DESCRIPTION OF THE DRAWING FIGURES

FIG. 15 is a sectional view of the fastener driving tool in the assembled condition.

FIG. 17 shows the in-situ cuff with the valve body in place prior to attaching the valve body to the cuff.

FIG. 18 shows the cuff attached to the patient and to the valve body that has been moved from the FIG. 16 position to the FIG. 17 position.

FIG. 21 shows an alternative form of the tool having two fastener-delivering heads and which can be used to repair an aneurysm.

FIG. 22 is an exploded section of FIG. 21.

FIGS. 34a–34e and 34a'–34e' show the steps through which a staple according to the present invention follows as it is being forced into and through elements to be stapled.

Figure 35:
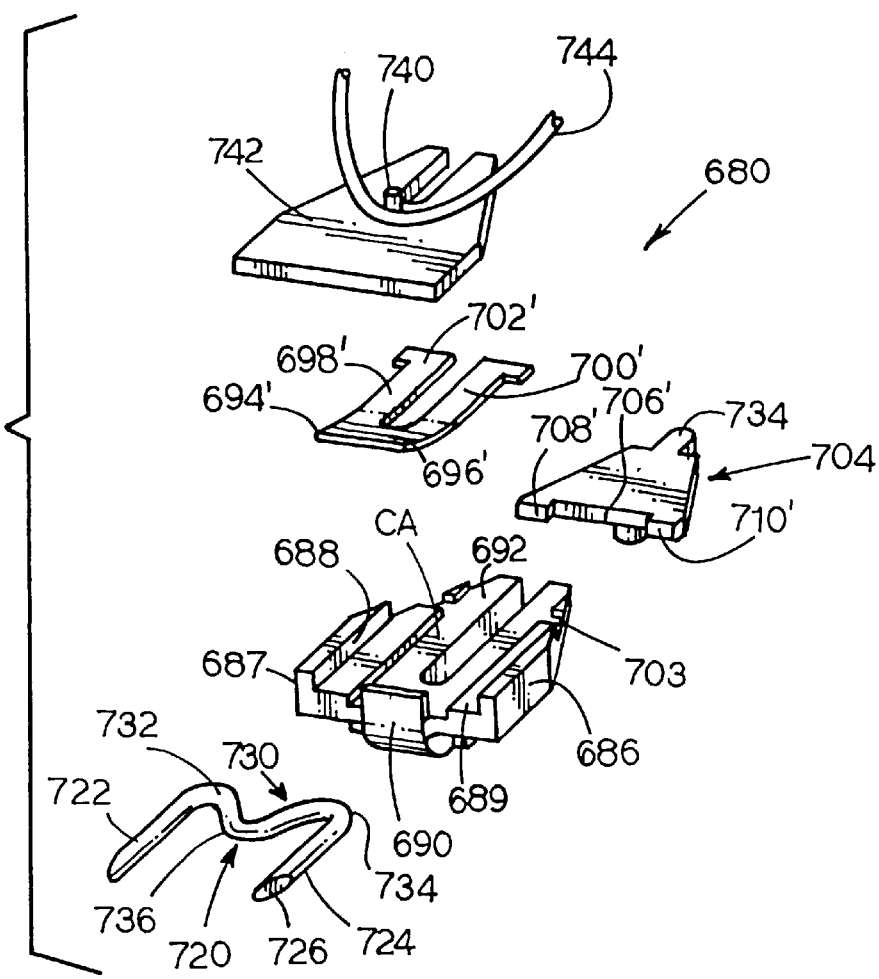

FIG. 35 is an exploded perspective view of another form of staple delivery assembly in which the assembly is returned to an initial position by an elastomeric element.

Figure 36:
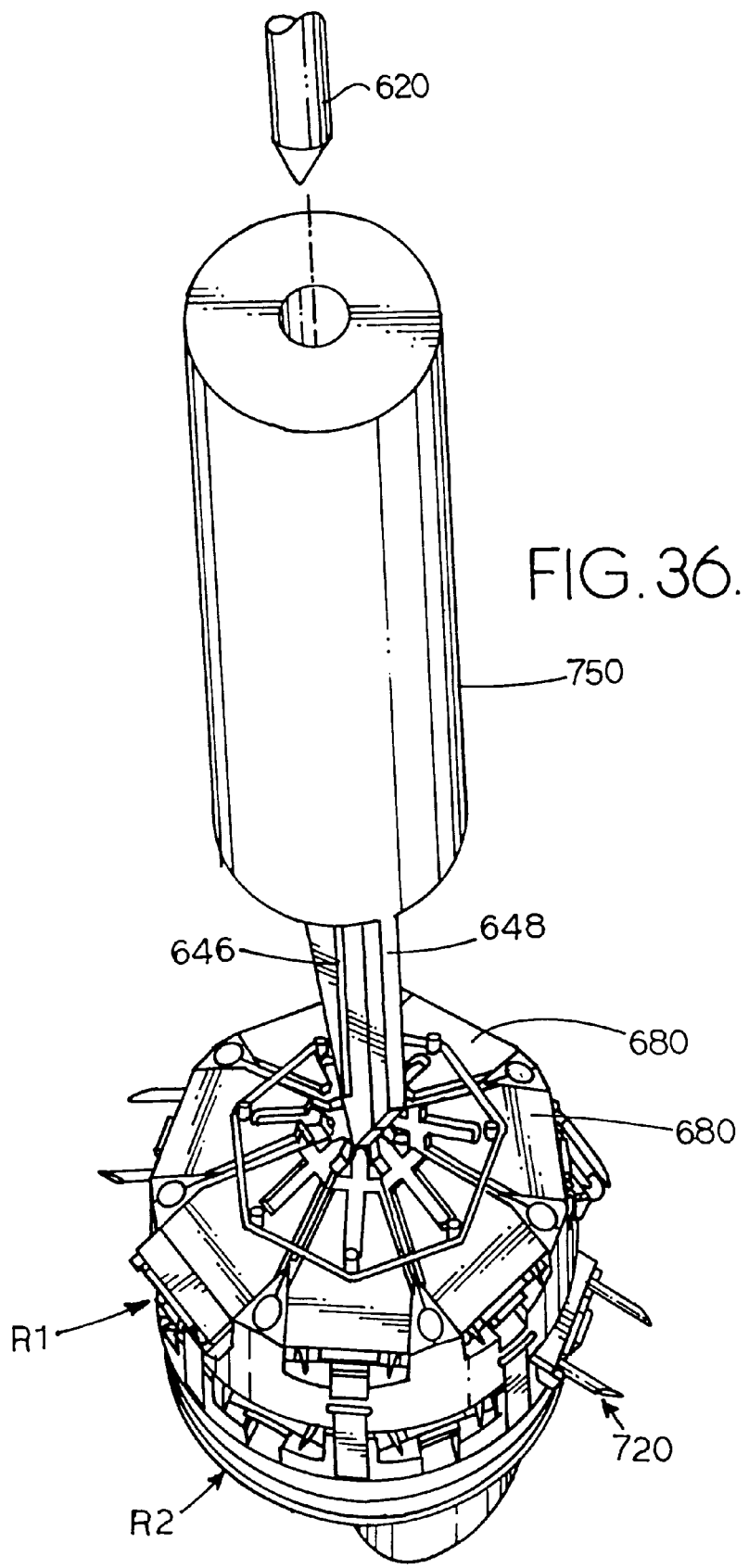

FIG. 36 is a perspective view of another form of staple delivery instrument according to the present invention.

Figure 37:
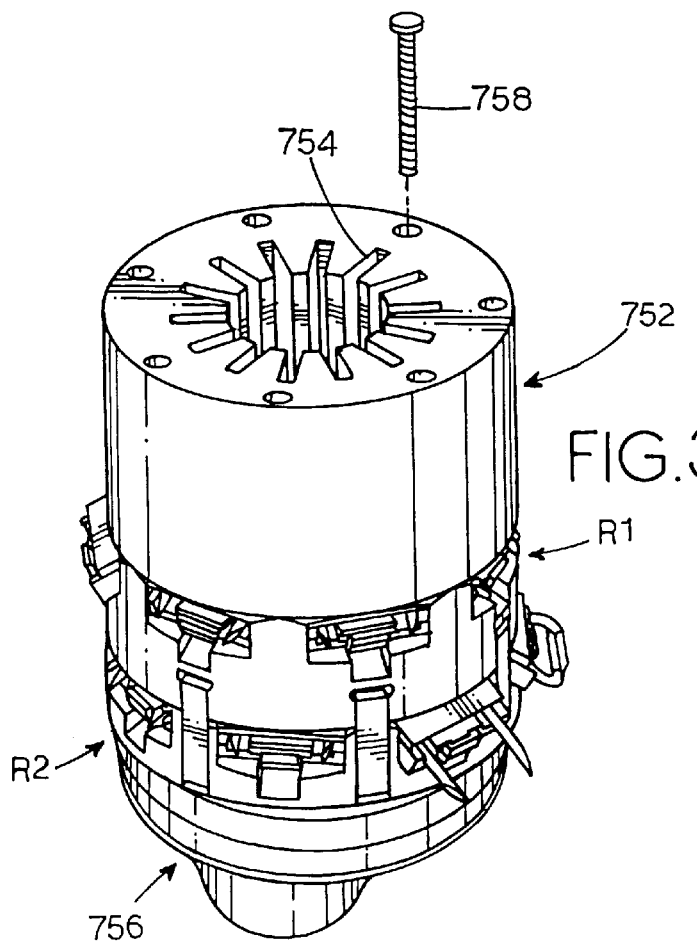

FIG. 37 is a perspective view of a head portion of the staple delivery instrument shown in FIG. 36.

Figure 38:
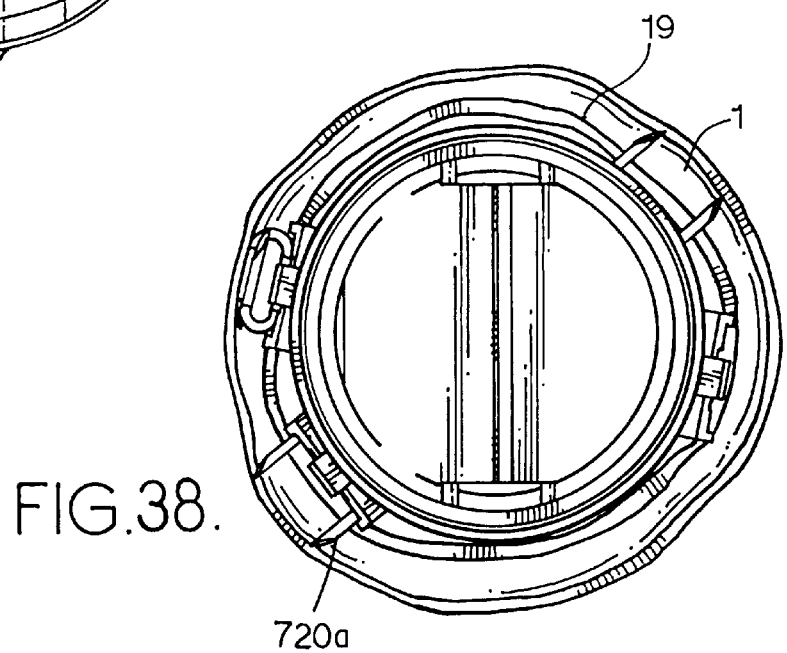
Figure 39B:
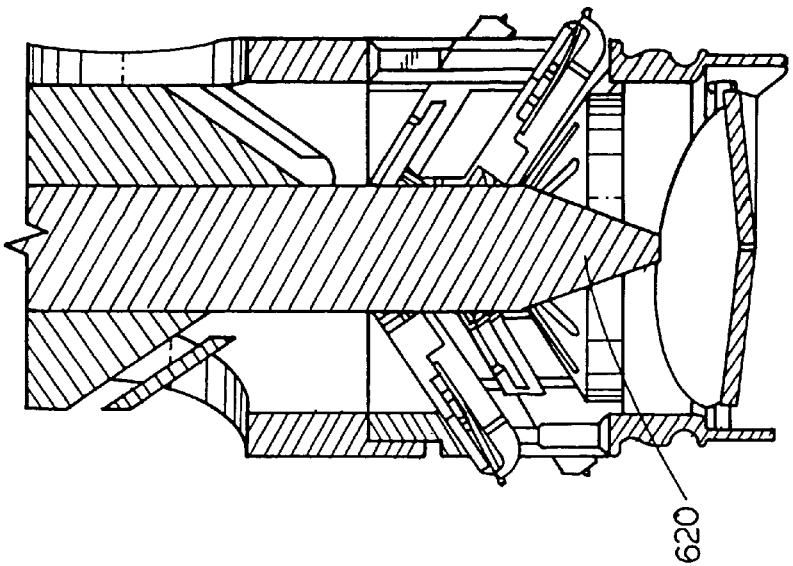
Figure 39A:
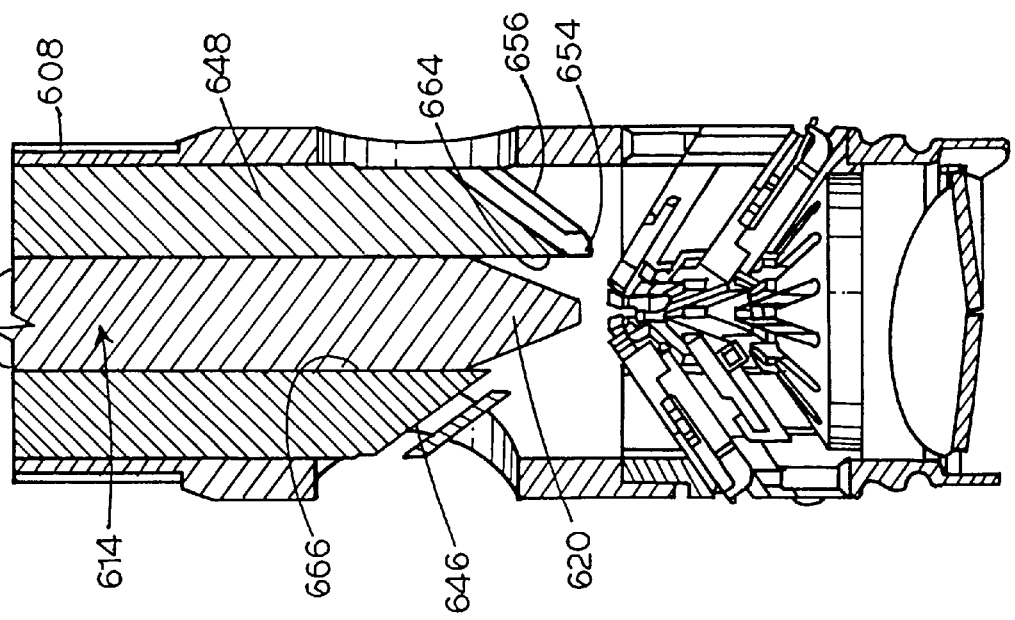
Figure 39C:
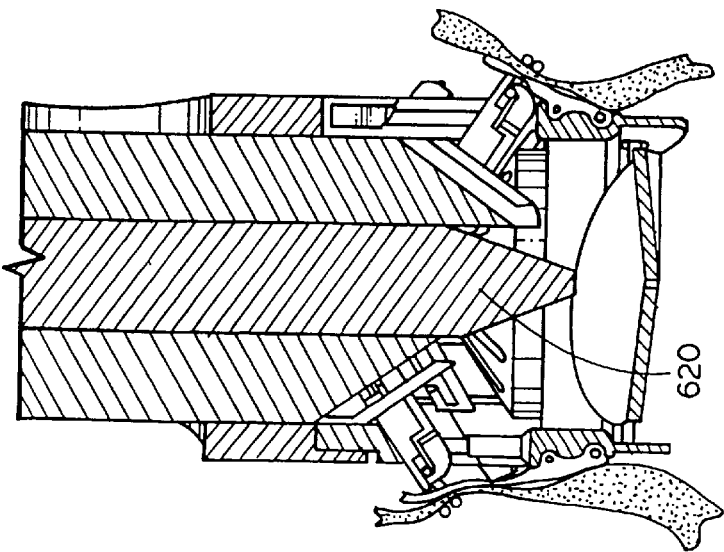
Figure 39D:
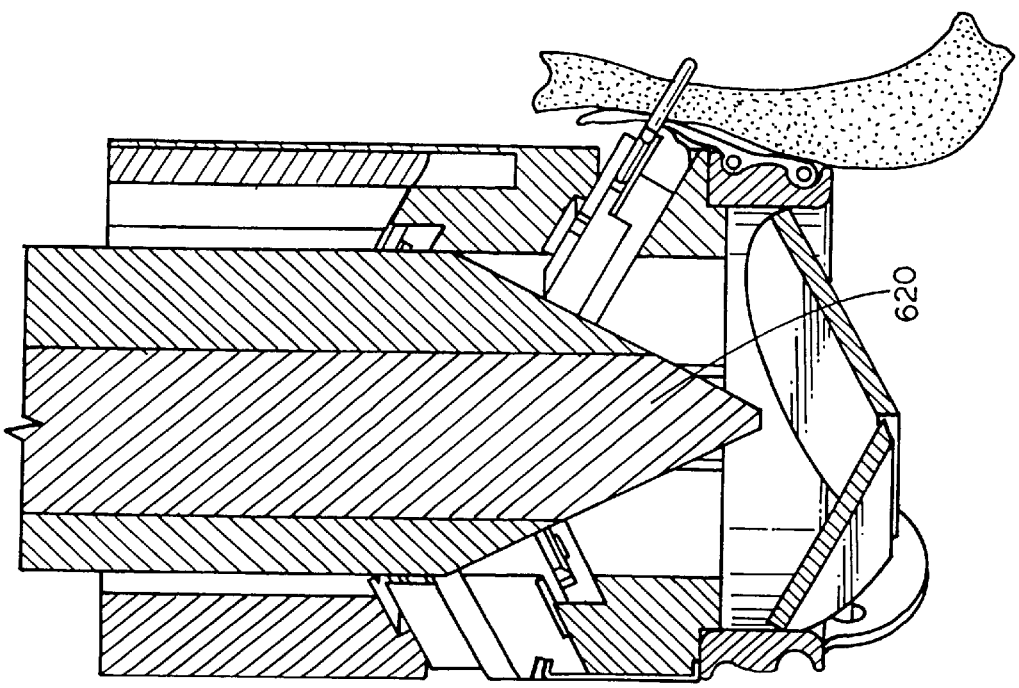

FIG. 38 is a top plan view of an anchor ring in place in an aorta illustrating how the means of the present invention can stretch the ring against the aorta and how the staples of the present invention attach the ring to the aorta.

FIGS. 39a–39d illustrate the operation of the staple delivery instrument shown in FIG. 36.

FIGS. 40a–40c further illustrate the operation of the FIG. 36 staple delivery instrument.

Figure 31:
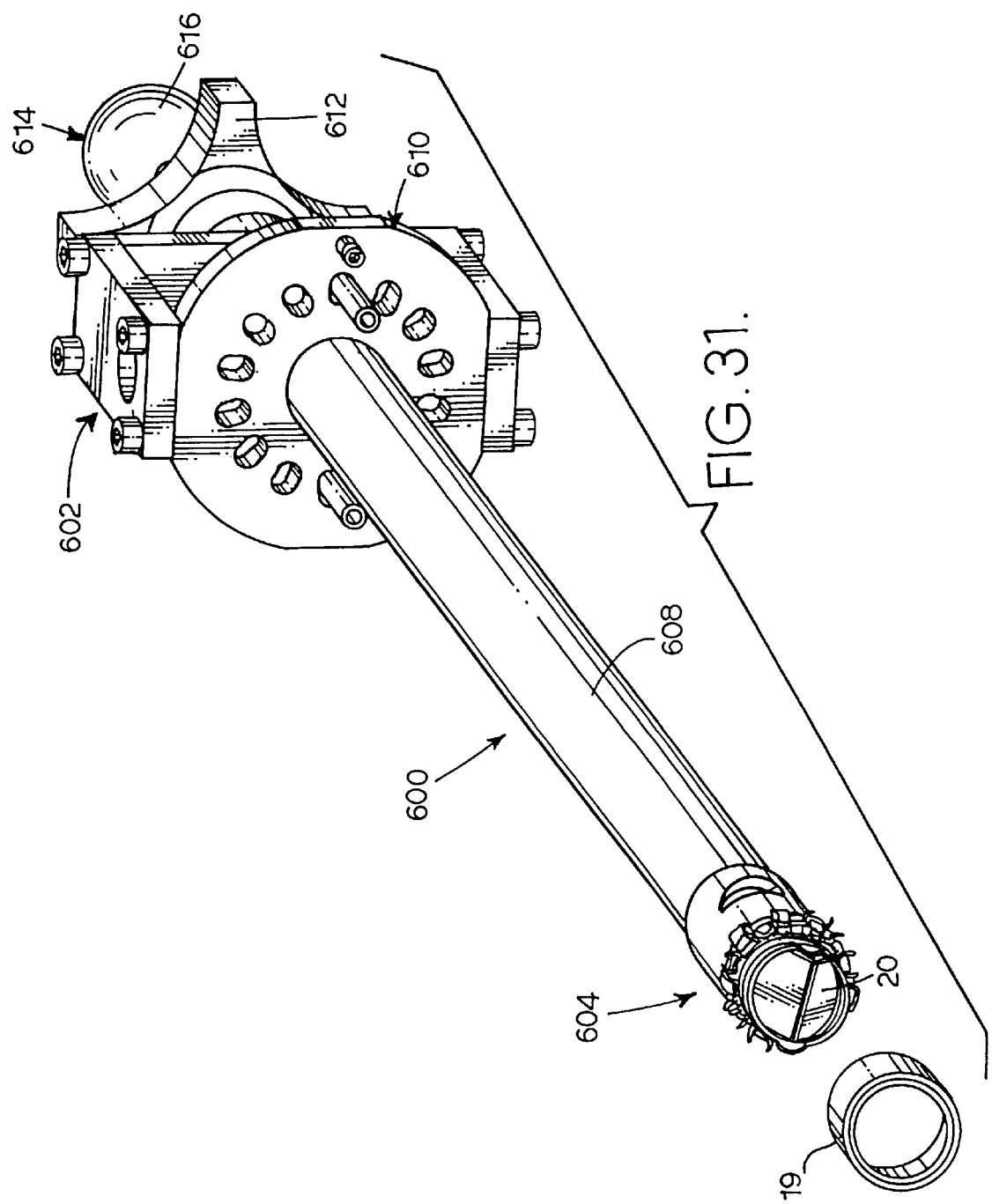
FIG. 31 is a perspective view of a staple delivery instrument.
Figure 41:
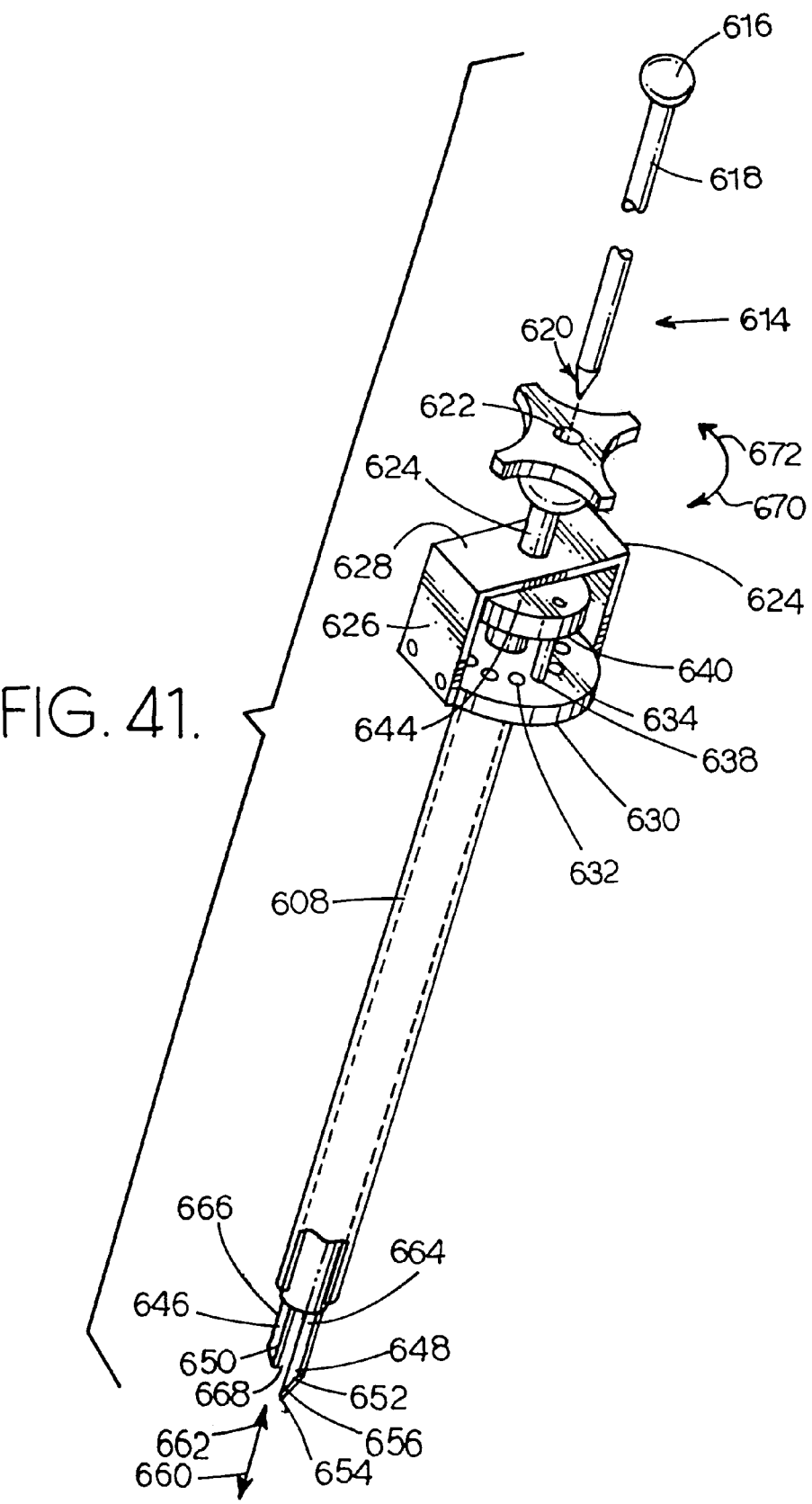

FIG. 41 is a perspective view of the device shown in FIG. 31 with the staple delivery assembly removed.

Figure 42:
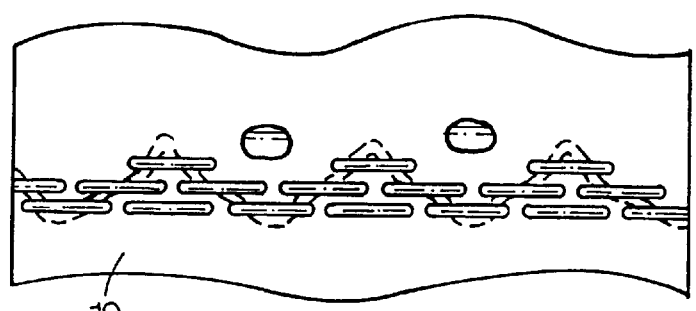

FIG. 42 is staple pattern in a cuff that can be established using a staple delivery instrument with three rows of driver assemblies.

Figure 43:
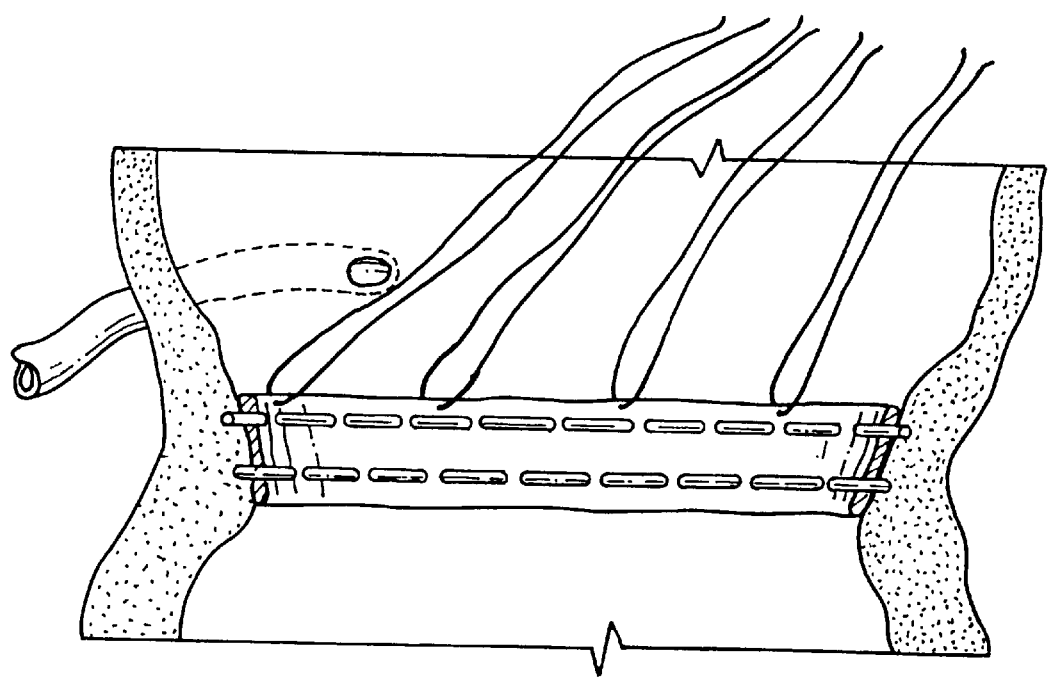
Figure 44:
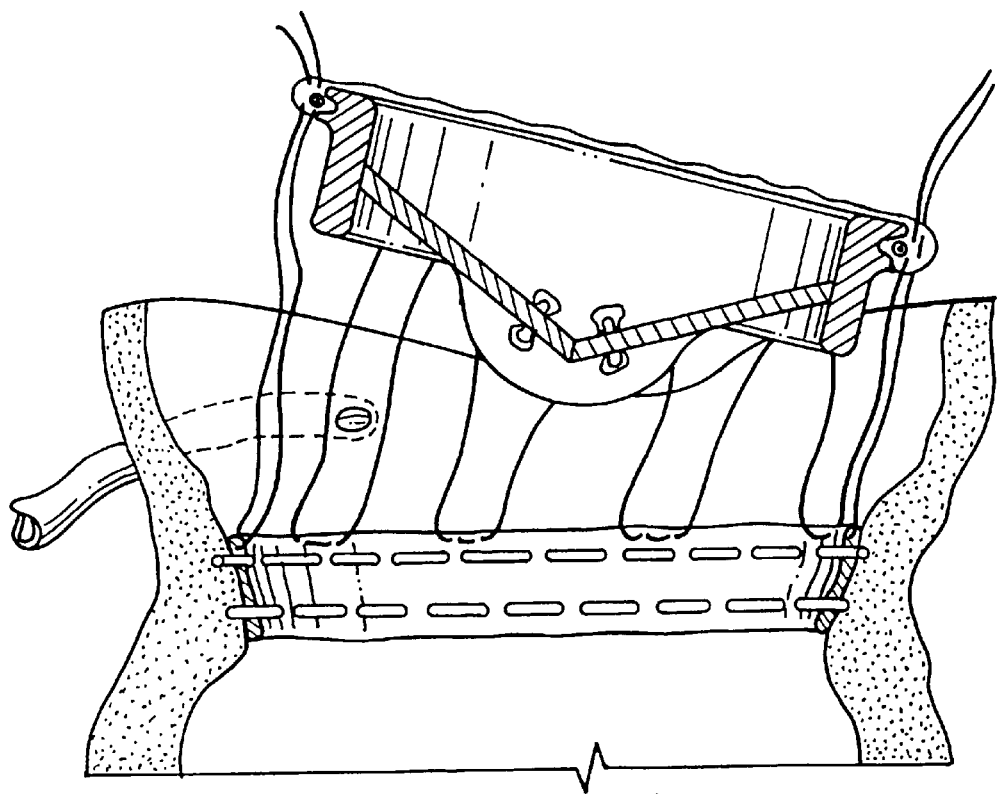
Figure 45:
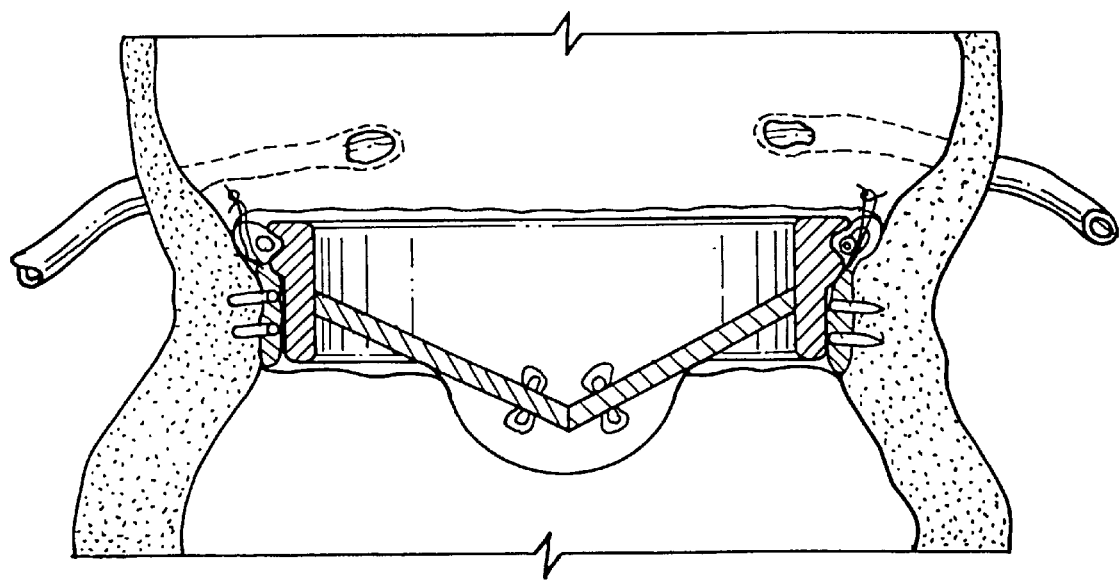

FIGS. 43–45 illustrate the steps in placing a heart valve onto a cuff that has been stapled to a patient's aorta.

Figure 46:
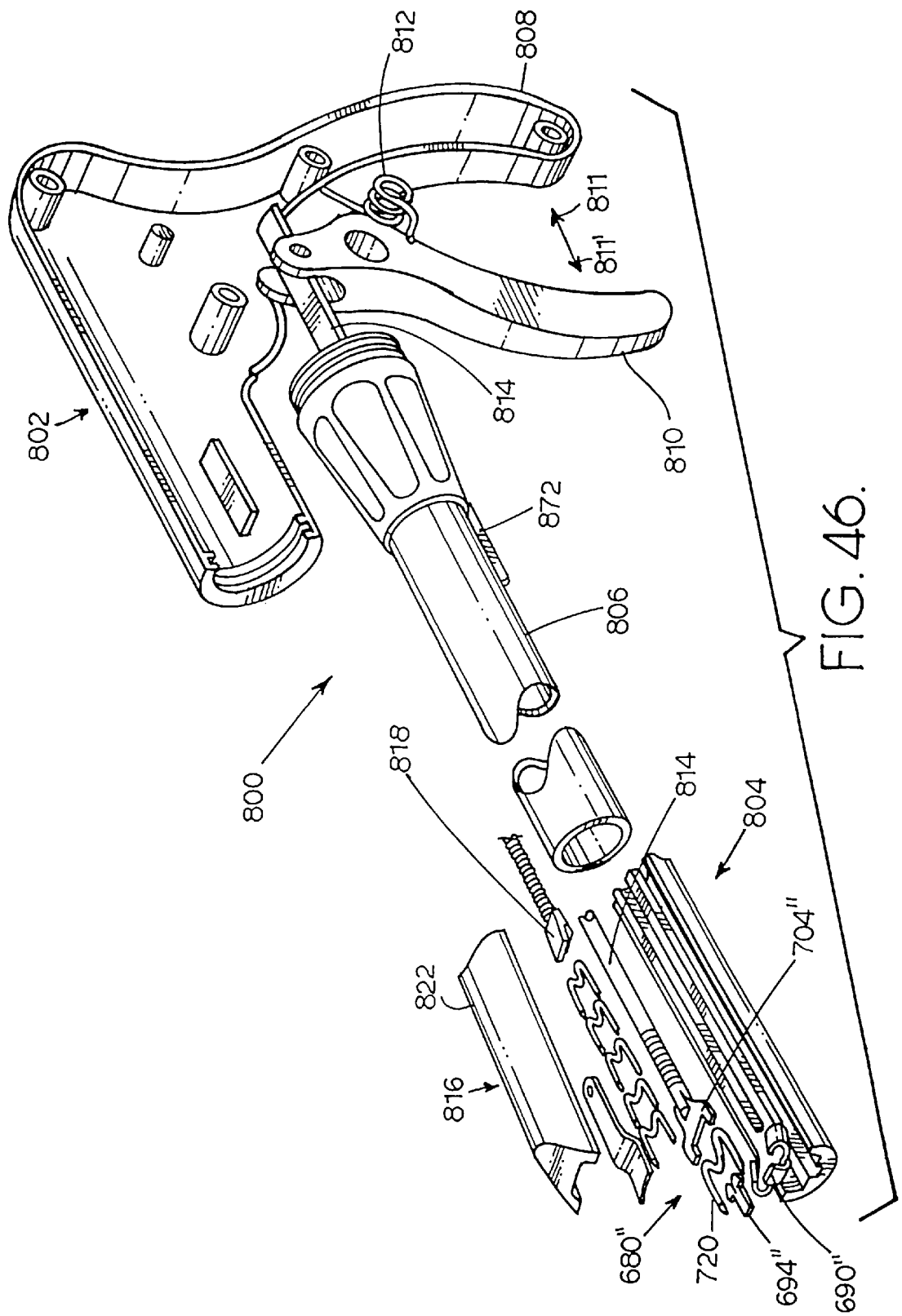

FIG. 46 is perspective of another staple delivery instrument.

Figure 47:
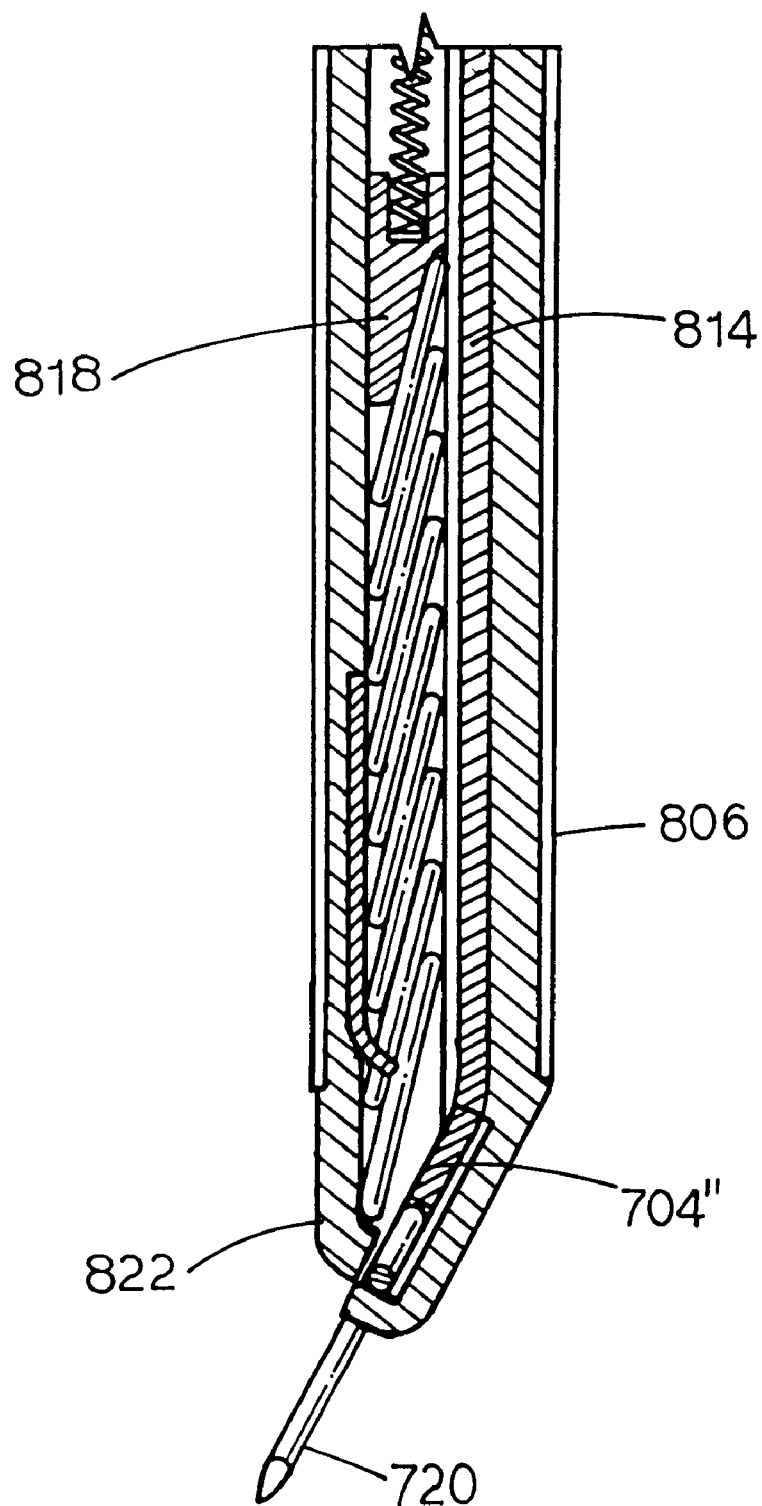

FIG. 47 is partial view of the FIG. 46 instrument illustrating the angled nature of the staple delivery associated with that instrument.

Figure 48:
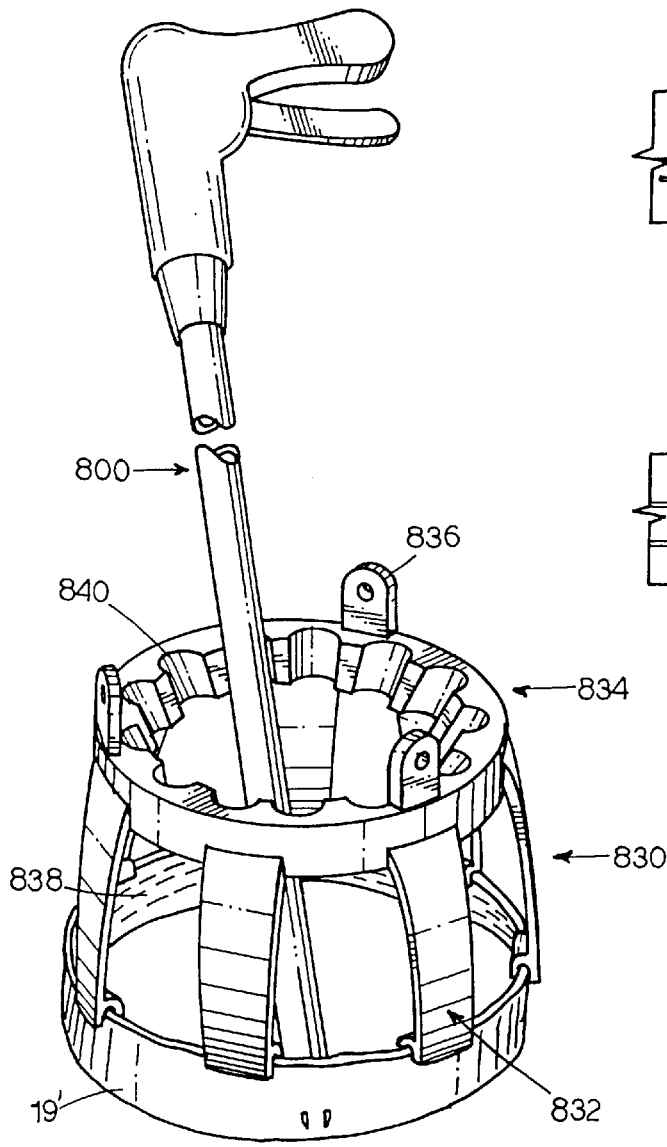

FIG. 48 shows an anchor ring placement element that can be used with the staple delivery instrument shown in FIG. 46.

Figure 49:
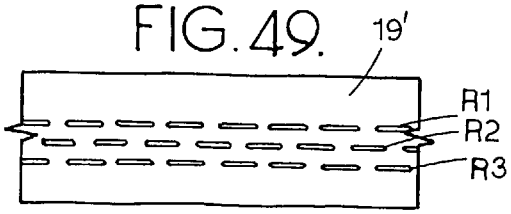

FIG. 49 illustrates multiple rows of staples placed using the staple delivery instrument shown in FIG. 46 and the anchor ring placement element shown in FIG. 48 and following a staple pattern established by icons placed on the anchor ring.

Figure 50A:
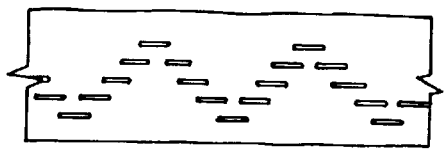

FIG. 50A shows a staple pattern established "on the fly" using the FIG. 46 staple delivery instrument and the FIG. 48 anchor ring placement element.

Figure 51:
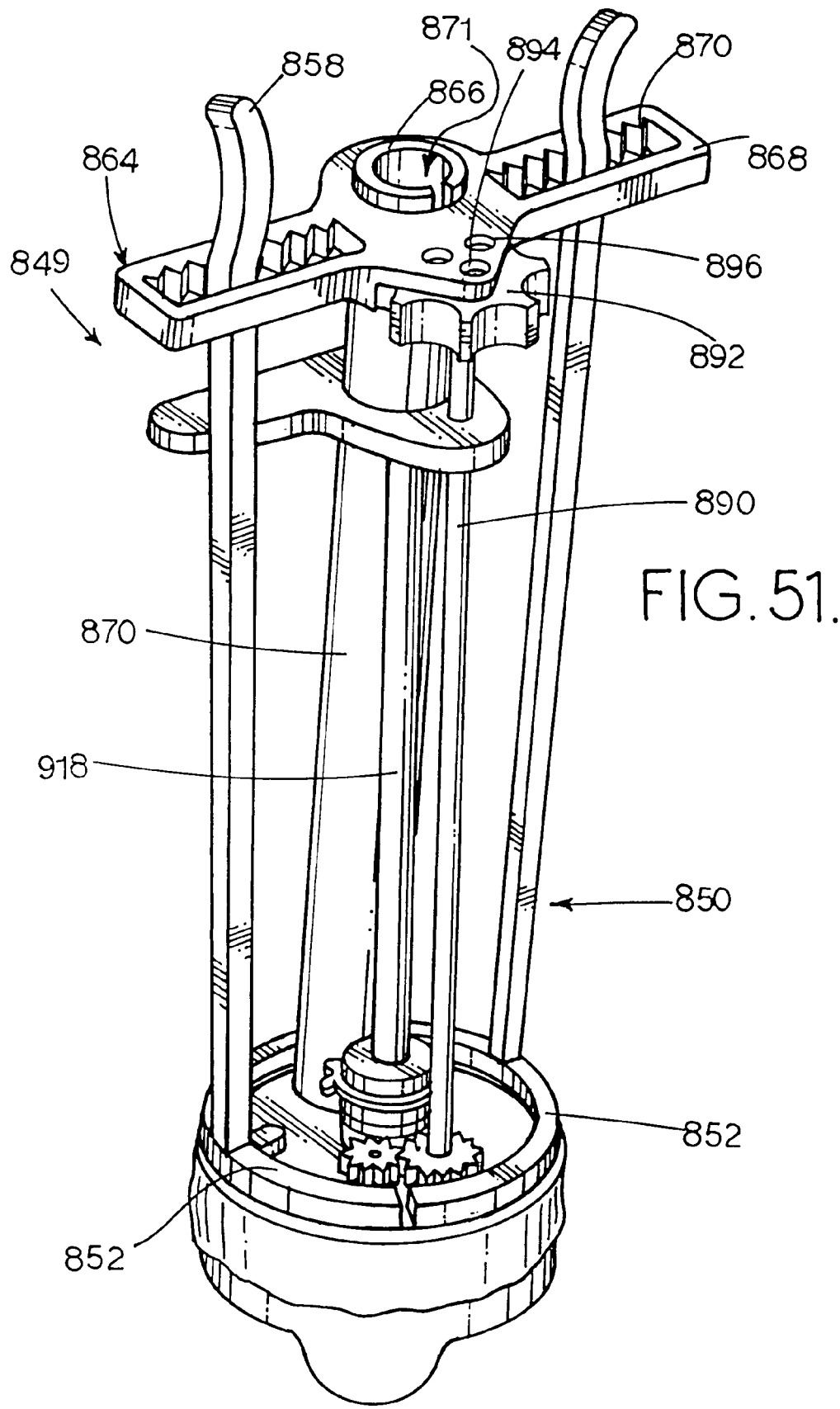

FIG. 51 is a perspective view of an automatic staple placement system that uses the staple delivery instrument shown in FIG. 46.

Figure 52:
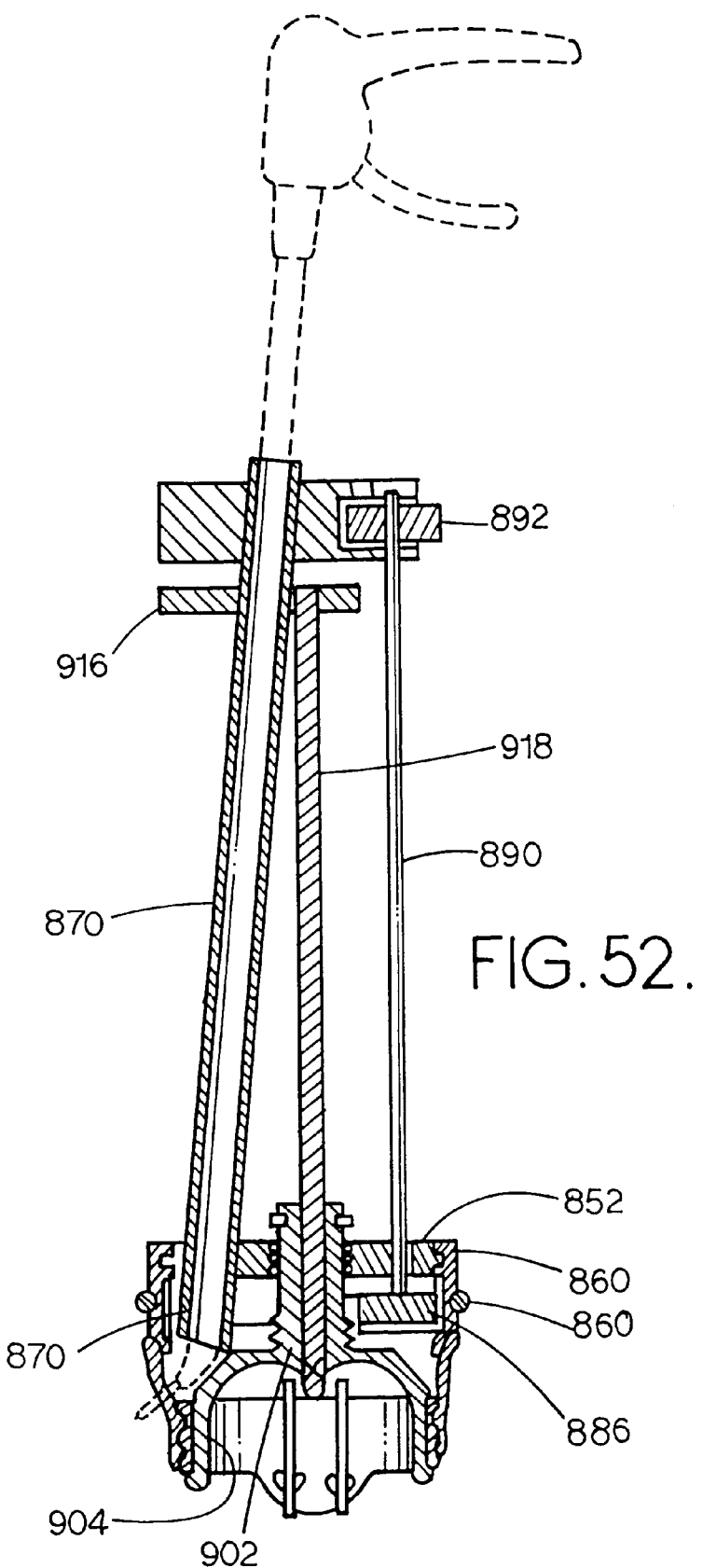

FIG. 52 is an sectional view of the FIG. 51 system showing the FIG. 46 tool in place in the system.

Figure 53:
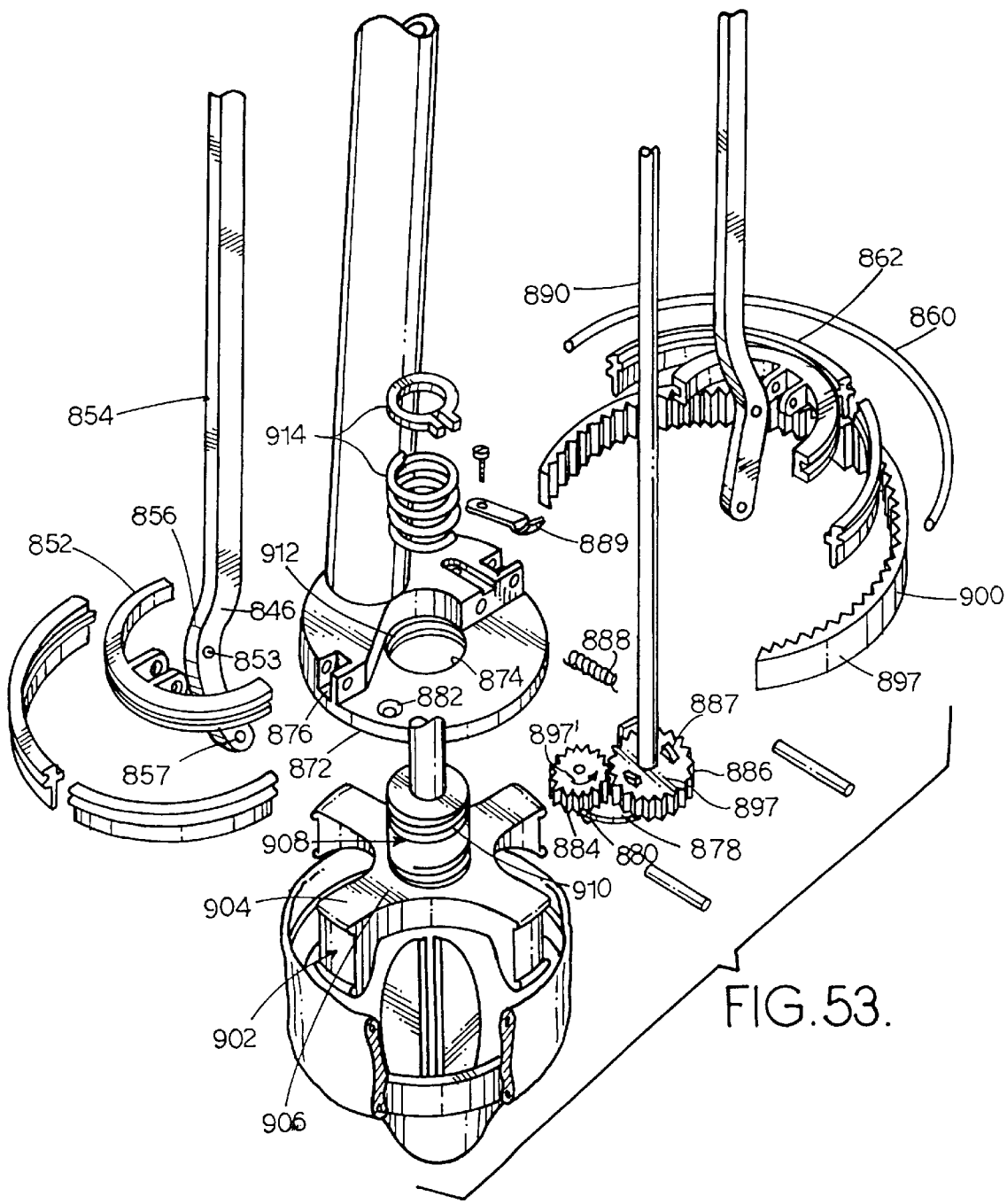

FIG. 53 is an exploded perspective partial view of the FIG. 51 system.

Figure 54A:
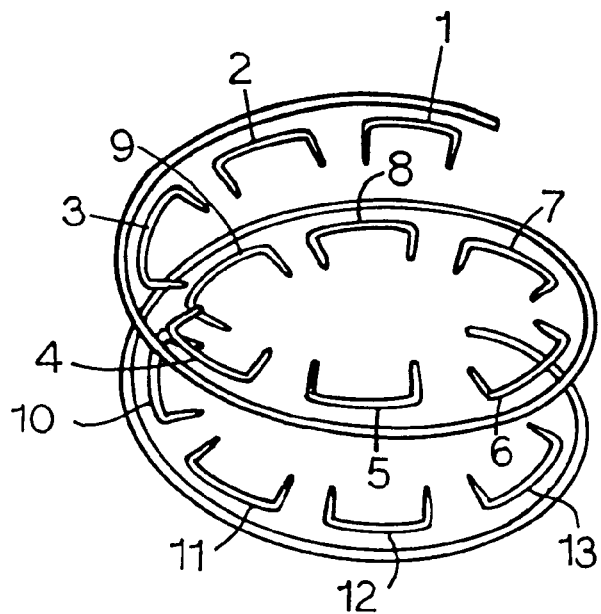
Figure 54B:
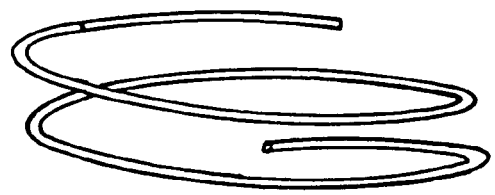
Figure 54C:
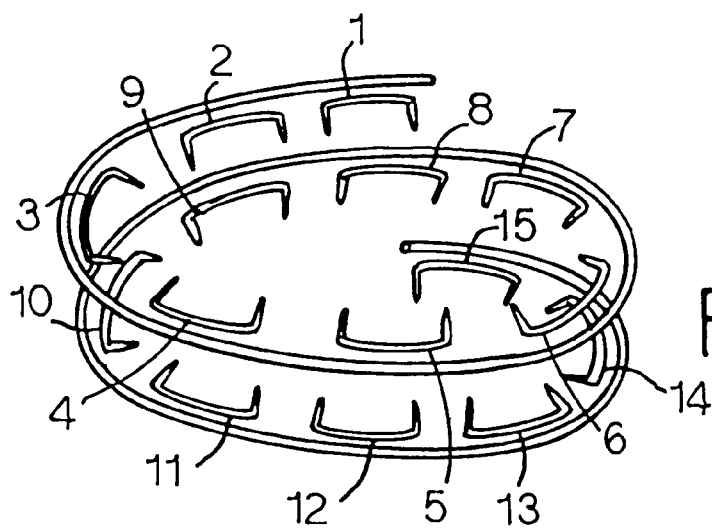

FIGS. 54*a*–54*c* illustrate helical staple patterns that are established using the staple system shown in FIG. 51.

Figure 55:
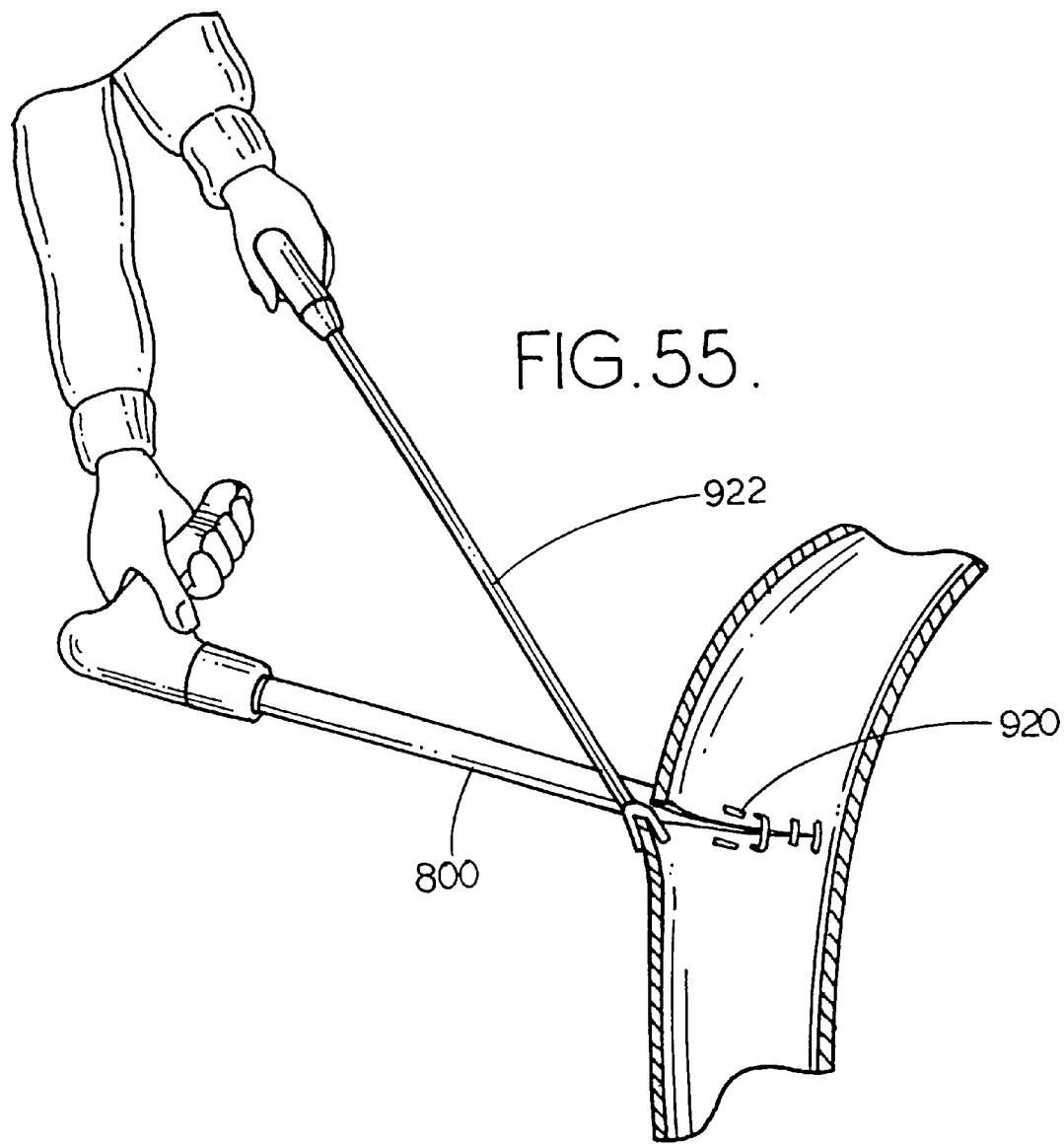

FIG. 55 illustrates the use of the FIG. 46 tool to close an aortomy.

Figure 56:
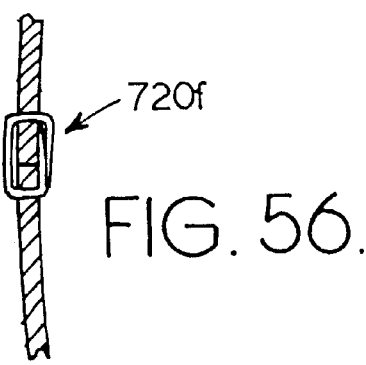

FIG. 56 illustrates the closed aortomy showing how the staple of the present invention brings incised edges together.

DETAILED DESCRIPTION OF THE PREFERRED EMBODIMENT OF THE INVENTION

The invention is a device and method of fastening an aortic valve prosthesis or vascular graft, into living tissue, particularly suitable for minimally invasive surgery. In the preferred embodiment, the heart valve is separable from its sewing cuff. The valve body has special grooves in its periphery to allow the valve to be attached to the sewing cuff after it has been fastened into the annulus of the patient's aorta. The sewing cuff is specially constructed to provide a means to open up or unfold it and then detachably retain it to the fastener tool to allow for remote attachment of the cuff deep in the aortic lumen. Once the fasteners have been driven and the cuff is securely attached to the aortic annulus, the cuff attachment means is released and the fastener driver tool is removed from the heart. The prosthetic heart valve is then inserted into the aortic lumen and docked to the cuff. A special element is provided between the heart valve body and the cuff to signal to the surgeon when the valve body is properly seated in the in-situ cuff. An annular extension spring provides tension to hold the valve in place. It provides a tactile feedback which indicates to the surgeon that the valve body is securely attached to the cuff. Once the valve body is properly seated in the cuff, the cuff is attached to the valve body with drawstrings or the like. It is noted that while drawstrings are one means for attaching the cuff to the valve body, many other means, such as will be known to those skilled in the art based on this disclosure, can also be used without departing from the scope of this disclosure. Once tightly secured to the valve body, the cuff drawstrings are trimmed thereby completing the installation.

Currently-available valve replacements are hand sewn into the aorta after surgical removal of the defective valve. A critical component of the present invention is that the cuff is fastened to the living tissue with a series of metal fasteners or staples. The staples are arranged in two rows and are staggered to ensure a secure fit between the cuff and the tissue. The fastener driving tool has two stapling mechanisms on two different levels with the staple driving mechanisms on each level being spaced apart by 105° (see FIG. 11). The staples in each row are set two at a time, preferably 180° apart in each row, with both rows being set at the same time. The staple mechanisms in one row is off set from the staple mechanisms in the other row. After forming the two sets of opposed fasteners, the attachment tool is rotated. This automatically indexes to the proper fastener offset to create two staggered rows of fasteners. The offset between staple mechanisms in the two rows is preferably a 30° index and will provide twelve fasteners per row for a 19–21 mm aortic annulus. The fastener driver tool has means to dilate between standard size valve bodies. Thus, the same fastener driving tool can be used on all sizes from 19–23 mm and then the next size up would cover ranges from 23–27 mm, the next 27–32 mm and so forth. This is an important advantage because the surgeon will always want to place the largest body in the cuff. Presently, if a surgeon chooses a 19 mm valve and finds the cuff to be slightly loose in the annulus, it is a major expense to cut loose the 19 mm valve and try again with a 21 mm valve. The fastener driver tool of the present invention may include an indicator that indicates to the surgeon when he is fastening the cuff what size valve the annulus has been stretched to, thus eliminating guesswork.

Figure 1:
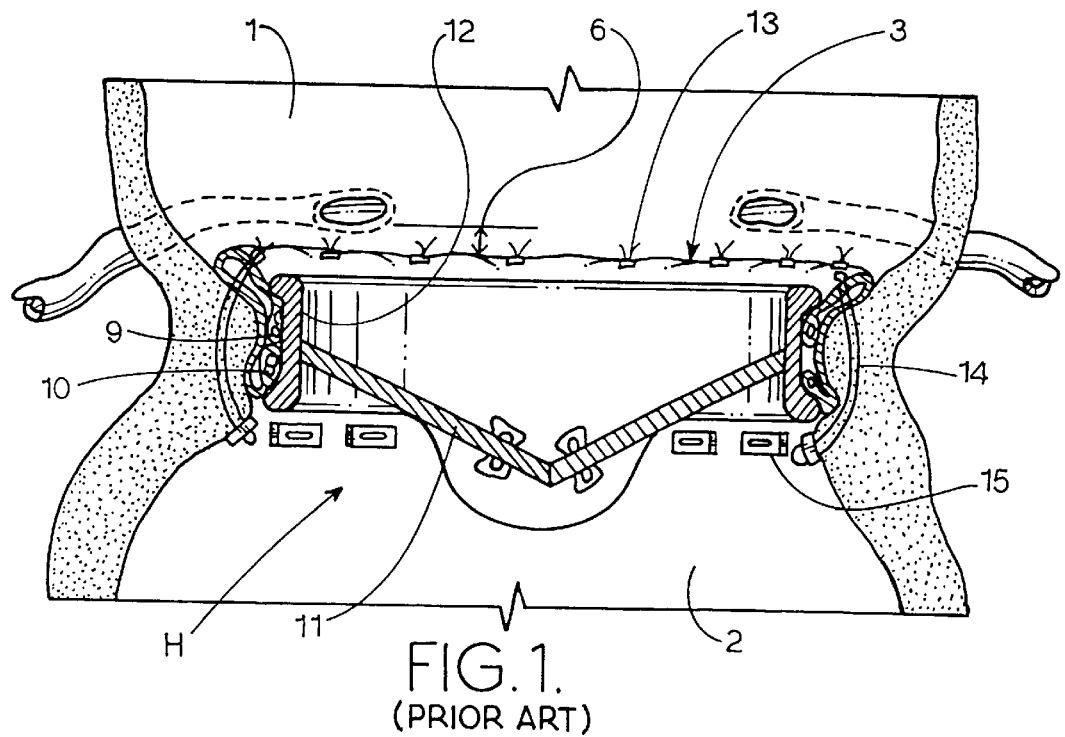
FIG. 1 shows a sectional view of a prior art prosthesis heart valve in place in a patient.

Referring first to FIG. 1, a prior art prosthetic heart valve II is shown installed in the annulus of an aorta 1 next to a left ventricle 2. Valve H is secured in place by a series of sutures 14 which are tied in knots 13. The sutures are most often used with felt pledgets 15 to spread the load of the sutures evenly so as not to tear the tissue. Valve H includes a cuff 3 which is attached to the perimeter of base 12 of valve H in the factory. Drawstrings 9 and 10 are used to effect this attachment. The cuff and valve body are implanted as a single unit with the cuff being hand sewn to the tissue. Leaflets 11 are also shown as is the distance between the top plane of the valve and the right coronary artery junction with the aorta. This distance is indicated in FIG. 1 by numeral 6.

Figure 2:
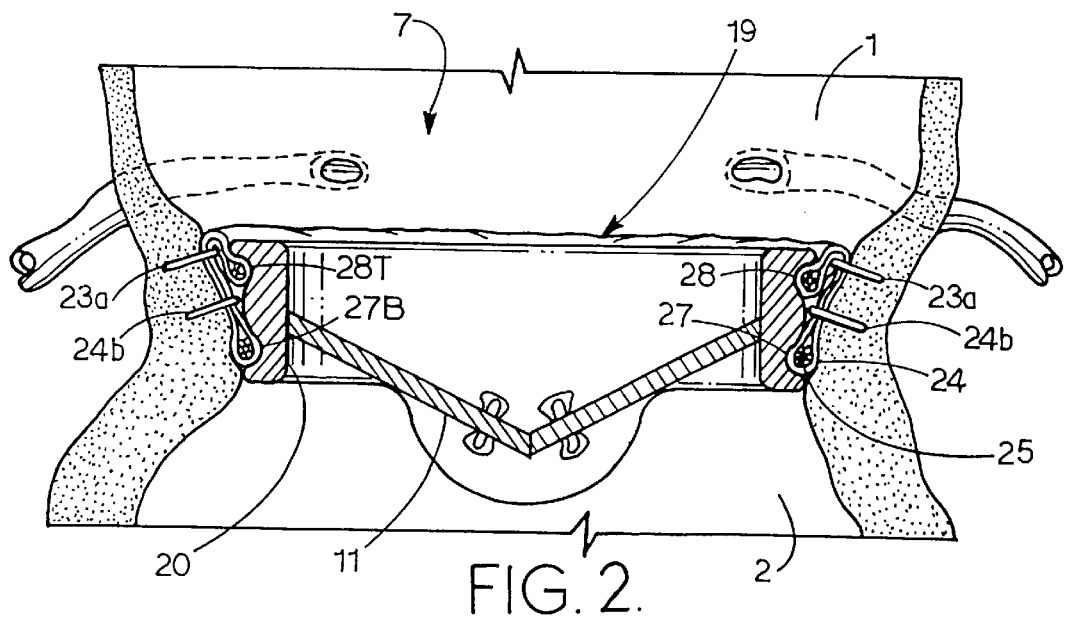
FIG. 2 is a sectional view of the prosthesis valve of the present invention installed in the aortic annulus of a patient.

Shown in FIG. 2 is a prosthetic valve 7 embodying the present invention installed and seated in the annulus of the left ventricle. Fasteners 23*a* and 24*b* are used to fasten sewing cuff 19 to the annulus of the aorta. The fasteners are staples in the preferred form of the invention. Drawstrings 27 and 28 are used to secure the cuff to the body 20 of the valve, and an indicating means 25, such as a garter spring or the like, is located in the lower section of the cuff. One form of the indicating means includes a garter spring inside a pocket in the cuff. Indicating means 25 is used to signal the surgeon when the heart valve body 20 has been seated properly in the cuff 19 prior to activating the drawstrings. Contact between means 25 and the valve body provides the surgeon with a tactile signal that the valve body is properly seated in the insitu cuff.

As can be seen by comparing FIGS. 1 and 2, prosthetic device 7 has no sutures, no pledgets and will be installed as two parts—the cuff followed by the body; whereas, device 11 has sutures 14, pledgets 15 and is installed as a single unit. However, as can also be seen, the cuff in both instances is still securely connected to the valve body and the cuff can remain a flexible material, such as Dacron or the like whereby the surgeon will still be able to use familiar material. As will be discussed below, the cuff 19 is totally flexible so it can be deformed to fit the aorta rather than requiring the aorta to be deformed to fit the valve as is the case with the valve shown in FIG. 1. Still further, the fully flexible nature of the cuff 19 permits easy deformation of the cuff and thus significantly reduces stress on the tissue surrounding the prosthesis. Still further, the fully flexible nature of cuff 19 permits it to be pressed against the tissue at all times during the installation process so the chance of puckering or paravalvular leak paths is significantly reduced, if not completely eliminated. Using staples in place of the hand-set sutures of the prior art will, as will be understood from the present disclosure, permit the installation of valve 7 using a surgical technique that is minimally invasive.

Figure 3:
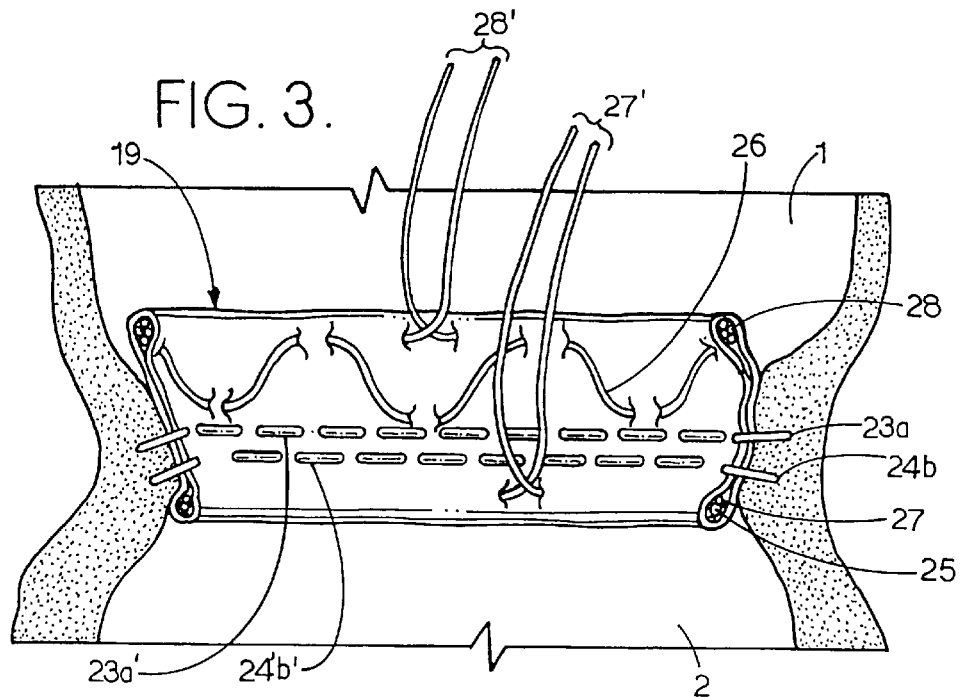
FIG. 3 is a sectional view of a sutureless cuff used in the present invention when the cuff has been stapled to the patient and prior to placement of the prosthetic valve body.

Cuff 19 is shown in place in the aorta prior to placement of the valve body in FIG. 3. Fasteners 23*a* and 24*b* are shown in two rows, with staples in one row being offset from corresponding staples in the other row. Thus, for example, staple 23*a*' in the top row corresponds to staple 24*b*' in the bottom row. The staggered nature of the staples in the two rows causes the cuff to be set by a continuous set of staples if the two rows are viewed together. That is, there is some portion of a fastener connecting the cuff to the tissue everywhere in the 360° of the circumference of the cuff. The two rows of staggered fasteners thus forms a means for connecting of the cuff to the tissue in a continuous manner about the entire perimeter of the cuff, and eliminates leak paths.

As shown in FIG. 3, the drawstrings 27 and 28 of valve 7 extend out of the cuff for a significant distance. As will be understood from this disclosure, these drawstrings have extensions 27' and 28' which extend out of the patient's body when the valve is being implanted. The extensions 27' and 28' are connected to the drawstrings 27 and 28 in the cuff which are means for fixedly attaching cuff 19 to body 20, and are actuating means attached to the drawstrings for operating the drawstrings from outside of the body after the sewing cuff has been attached to the patient to secure the cuff to the body 20. The prior art valve has no such drawstring extensions.

Figure 4:
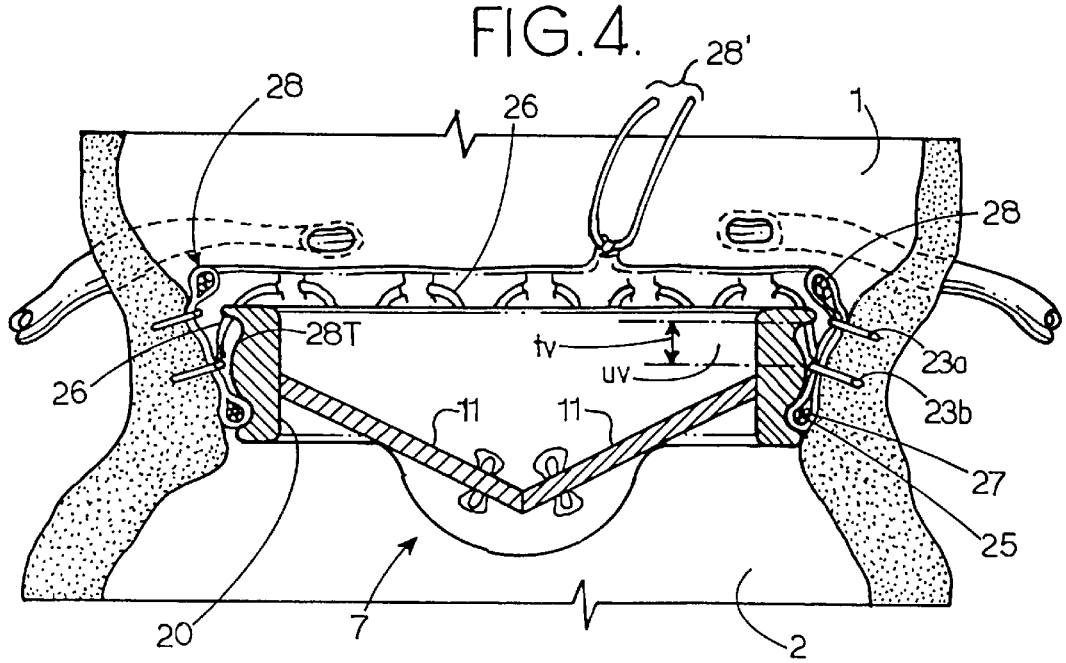
FIG. 4 is a sectional view of the prosthetic valve of the present invention after the cuff has been stapled in place and after the prosthetic valve body has been placed in the cuff and before the cuff is attached to the valve body.
Figure 5:
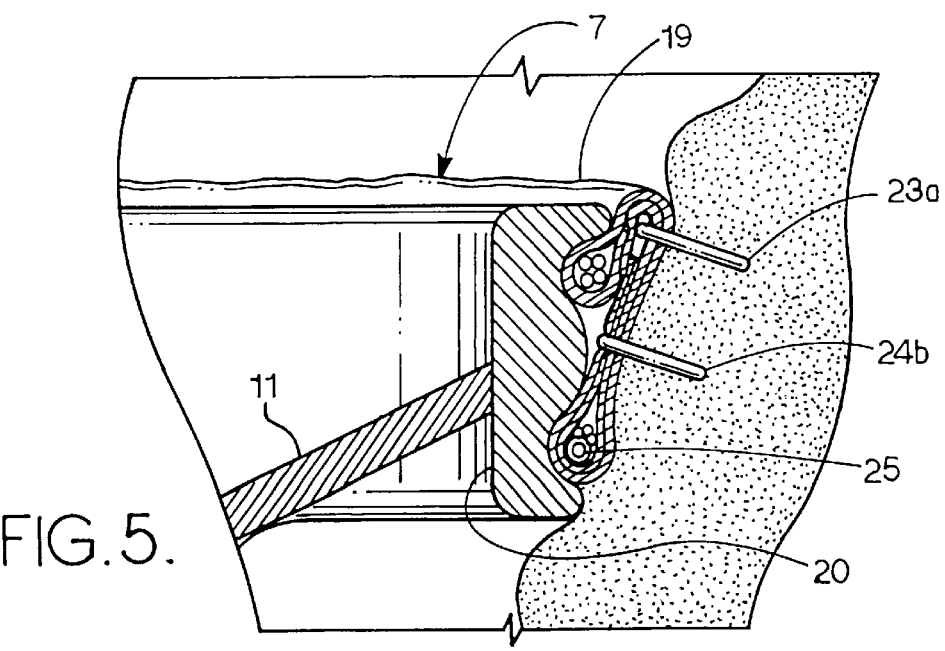
FIG. 5 is an enlarged sectional view of the sutureless prosthetic heart valve of the present invention with two rows of staples securing the cuff to the patient and the valve base attached to the cuff.

A zig-zag drawstring 26 is connected to extension 28' to be activated thereby. Drawstring 26 is sewn from top pouch 28 through the cuff and up again through the top pouch. When the activating means is activated, drawstring 28' is pulled and drawstrings 26 and 28 are activated. When drawstring 27 is pulled, drawstring 27 is activated and is pulled into recesses in the body of the valve. The recesses are shown in FIG. 2 at 28T and 27B respectively. FIG. 4 illustrates how the cuff will be drawn into the recesses of the valve body during this cinching procedure. In the FIG. 4 condition, the top cords have not yet been seated. When the cords are pulled tight and cinched up the zig zag drawstring will automatically pull the top cords down into the top recess. Further tightening will cinch the cords tight into the recesses. After tightening, knots can be defined in the cords to secure the means 27' and 28'. FIG. 5 shows the prosthesis after it has been set and the cuff attached to the body.

Figure 6:
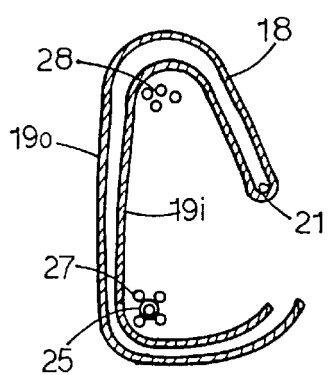
FIGS. 6, 7 and 8 illustrate how the sutureless cuff of the present invention is constructed.
Figure 7:
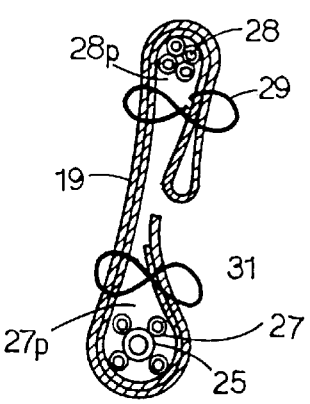
Figure 8:
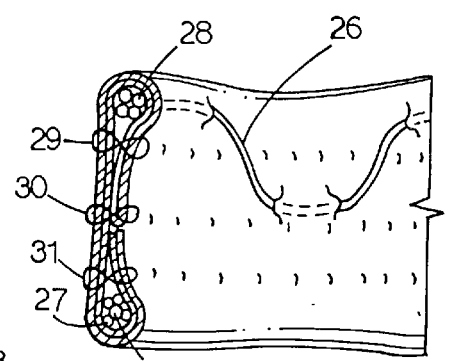

The sutureless cuff 19 is shown in FIGS. 6, 7 and 8. This cuff can be expanded for sizing. As shown in FIG. 6, the cuff is formed of a single, unitary tubular piece of fabric 18 which is folded over at location 21 to form an inner layer 19I and an outer layer 19O, with top cord 28 and bottom cord 27 being located at corners in the fabric. Cord 27 is adjacent to guide means 25. As shown in FIG. 7, stitching 29 and 31 create drawstring pouches 27P and 28P. A final suture stitch 30 is shown in FIG. 8 completes the cuff.

A tool T for placing the cuff in the patient and for applying the fasteners to attach the cuff to the patient is shown in FIGS. 9–16. This tool can be inserted into the patient to initially place the cuff in position, and to set the fasteners to attach the cuff. The tool is operated from outside the patient's body so the overall procedure is minimally invasive.

Figure 9:
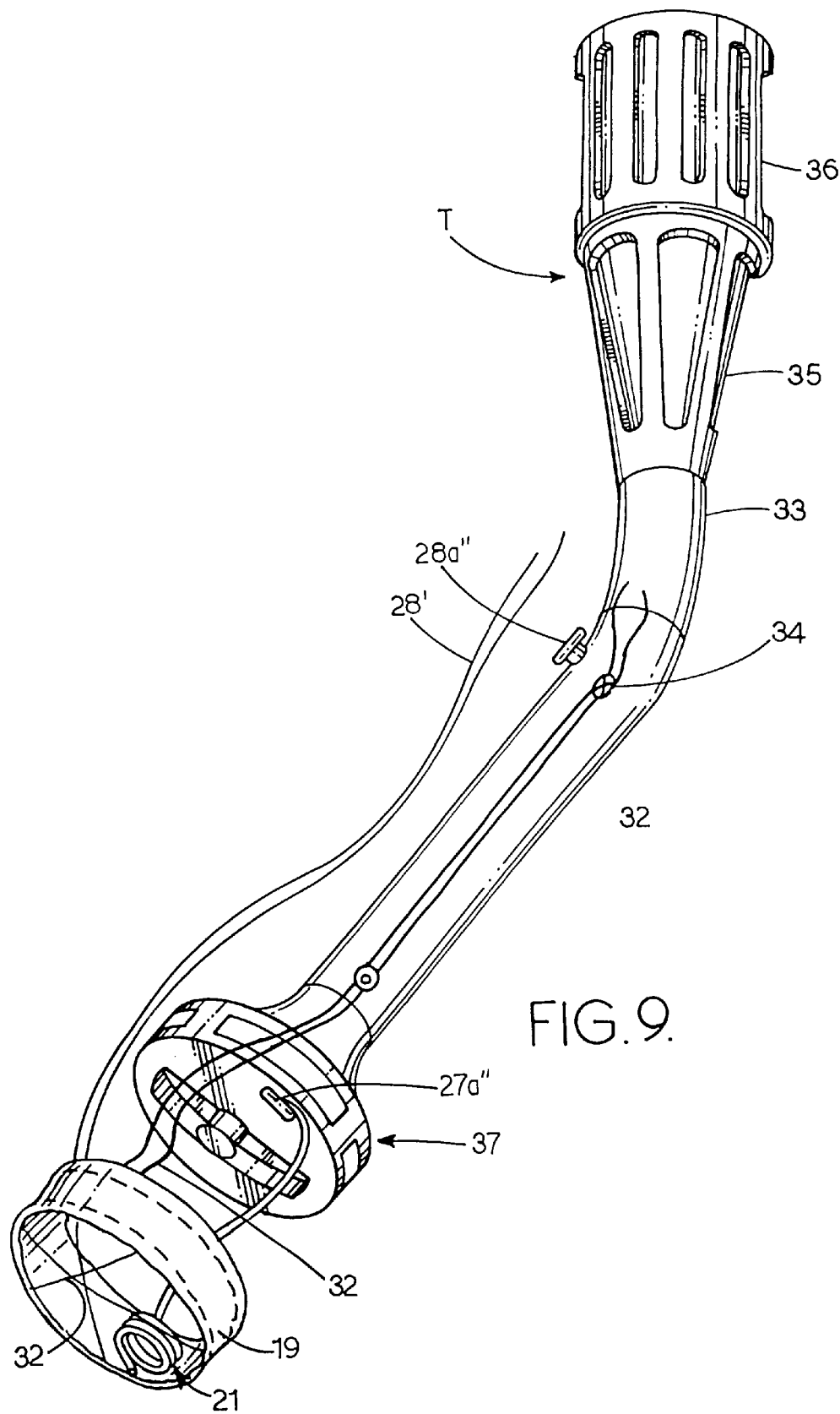
FIG. 9 is a side and bottom perspective view of a preferred form of a fastener driving tool used in the present invention.

Tool T broadly includes an operating handle 35 and a fastener deployment knob 36 on one end of a body 33 which can be curved if desired. An operating head 37 is on the other end of body 33. Anchor means 28a" are located adjacent to handle 35 and releasably attach the activating means 28' to the tool so these activating means are located outside of a patient's body during the cuff attaching procedure. As will be understood from the teaching of this disclosure, once the cuff is attached to the patient and the valve body is in place, the activating means are released from the tool and are operated to attach the cuff to the body. For the sake of clarity, the activating means are shown in FIG. 9 released from the tool. It is also noted that there will be a sleeve on the shaft to keep the drawstrings from winding up on the shaft.

Alternatively, the drawstrings can extend through the center of the shaft or held in a coiled at the bottom of the tool.

Suture stays 32 (see FIG. 9) are attached to the tool head 37, and the cuff is stretched over the head 37. The temporary suture stays 32 are drawn over the distal and proximal ends in order to secure the cuff to the head 37 during placement into the patient's body. The temporary suture stays 32 are tied to post 34 so that once the fasteners are deployed, the suture stays 32 can be cut to release the cuff 19 from the head 37 to help the surgeon with alignment of the body 20. The stays 32 act as a hammock or safety net to prevent the body 20 from being placed too low in the cuff which would result in the misalignment of lower drawstring 27 into the lower recess 27B. As deployment knob 36 is turned in a clockwise direction, each half revolution of the knob delivers two pairs of fasteners through the cuff. During that rotation, the latter part of the handle movement indexes head 37 inside the cuff 19 staggering the next pair of fasteners to be delivered. Drawstring activating means 28' is fed up along the shaft of the tool T to the holding cleats 28a" and are removed from this cleat, allowing tool T to be removed from the patient. Activation means 27' is retained coiled at the bottom of the instrument. The means 27' will be played out as the tool is removed from the patient whereby this means 27' will also be located outside the patient for activation.

The tool T has several functions. One function is to insert the cuff into the patient, another is to position the cuff in the patient, another is to fasten the cuff to the patient, and yet another is to hold the cuff securely against the patient's tissue during the fastening procedure. This last function is performed as a dilation and spreading procedure as will be understood from the teaching of this disclosure.

Figure 10:
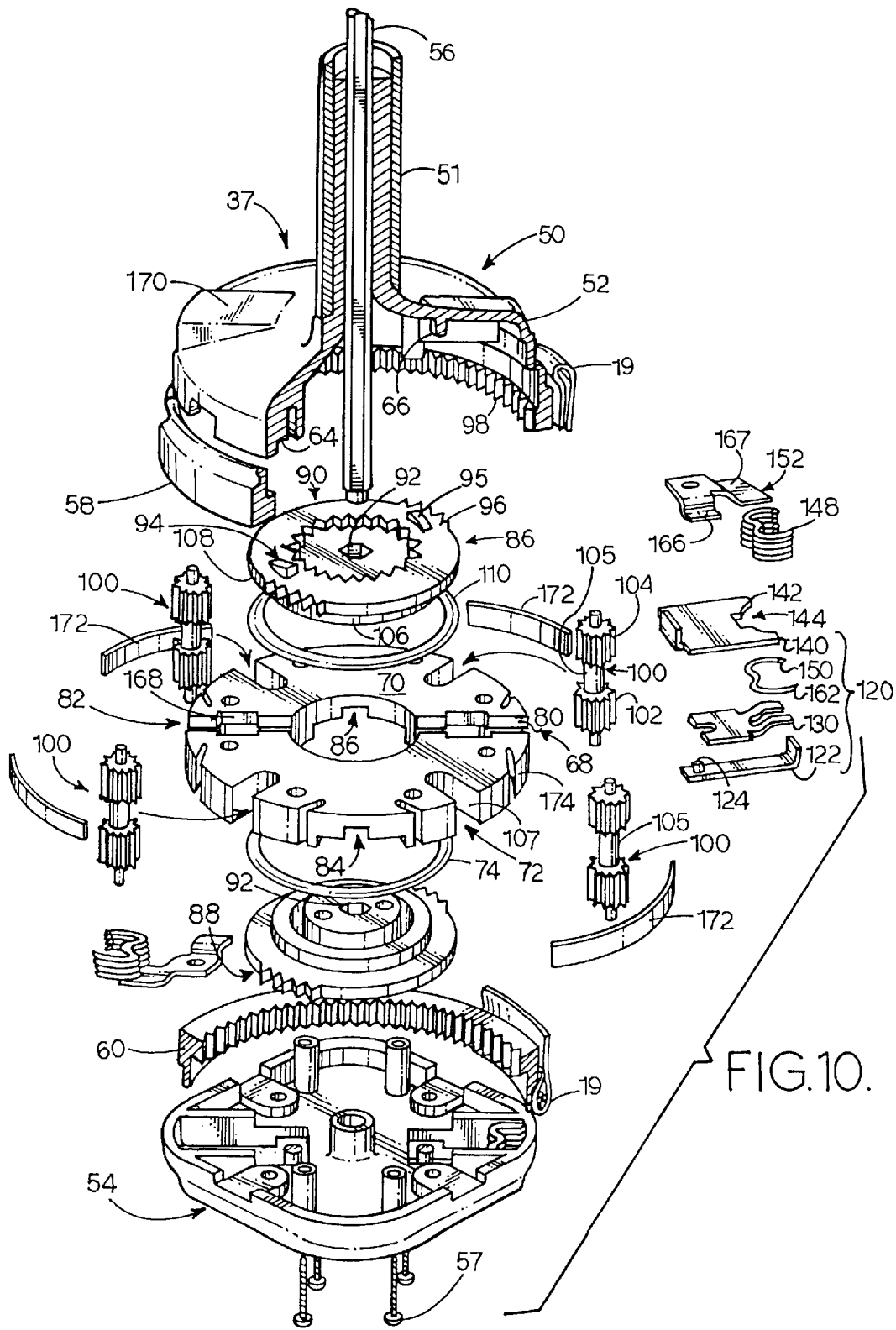
FIG. 10 is an exploded perspective view of the tool shown in FIG. 9.

Referring to FIG. 10, head 37 of tool T is shown as including a housing 50 which includes two sections, upper housing 52 and lower housing 54 both of which are attached to a hexagonal shaped drive shaft 56 and which are attached together by fasteners, such as screws 57. Drive shaft 56 is operatively connected to operating handle 36 to be rotated thereby. The housing sections are slidably connected to index rings 58 and 60 respectively and the cuff is connected to the index rings. As will be explained below, the housings are rotated during the fastening procedure, but the index rings remain stationary with respect to the housing so the cuff will remain stationary with respect to the housing. The index rings fit into grooves, such as groove 64, to be slidably connected to the housing sections. Upper housing 52 includes an anchor pin 66.

Also fixedly attached to the housing is a driver head plate 68 so that plate rotates with the housing. Plate 68 includes a top surface 70 and a bottom surface 72. Two identical fastener driver accommodating slots are defined on each surface of the driver head plate. These slots are identified in FIG. 10 by the reference numerals 80, 82, 84 and 86 and each extends radially of the plate. The slots are arranged so that top surface-located slots 80 and 82 are offset from each other by 180°, and bottom surface located slots are offset from each other by 180°, with the top surface-located slots being offset from the bottom surface located slots by 105°. After each fastener is set, the tool is rotated by 30° whereby the above-discussed stagger is established for the fasteners. The indexing of the head is achieved by movement of the handle 36 which is attached to a visually indicating means whereby a surgeon can keep track of where the fasteners are being set.

A cam means is located inside the housing. The cam means includes two cam plates, 86 and 88. The cam plates are identical, therefore, only one will be described. Cam plate 86 includes a top surface 90 and has a hexagonal hole 92 defined therethrough to attach the cam plate to drive shaft 56 for rotation therewith. An anti-retrograde means is included on cam plate 86 for preventing the cam plate from rotating in an undesired direction. Rotation in an undesired direction may interfere with the firm placement of the fasteners. The anti-retrograde means includes cleats 94 which are engaged by a one-way prong which permits rotation of the cam plate in one direction only. A second larger set of index lugs 95 can be provided to give feedback to the surgeon at the end of the fastener cycle. Index gear teeth 96 are defined on the outer peripheral edge of the cam plate and are operatively connected to index gear teeth 98 on the index ring 58 in a manner that rotates index ring 58 in a direction opposite to the direction of housing rotation at the same rate of rotation whereby the index ring remains stationary with respect to the patient as the housing rotates. This operation keeps the cuff, which is attached to the index ring, stationary with respect to the patient. Gears 96 and 98 are operatively coupled together by pinion 100 that is mounted at one end thereof on driver head plate 68 and at the other end thereof to the housing section 52, 54. Pinion 100 has a first gear teeth 102 engaging teeth 96 and second gear teeth 104 engaging gear teeth 98 for transmitting rotation of the cam plate to the index ring. Each pinion has a waist section 105 that is received in a pinion slot 107 defined in driver plate 68.

Figure 11:
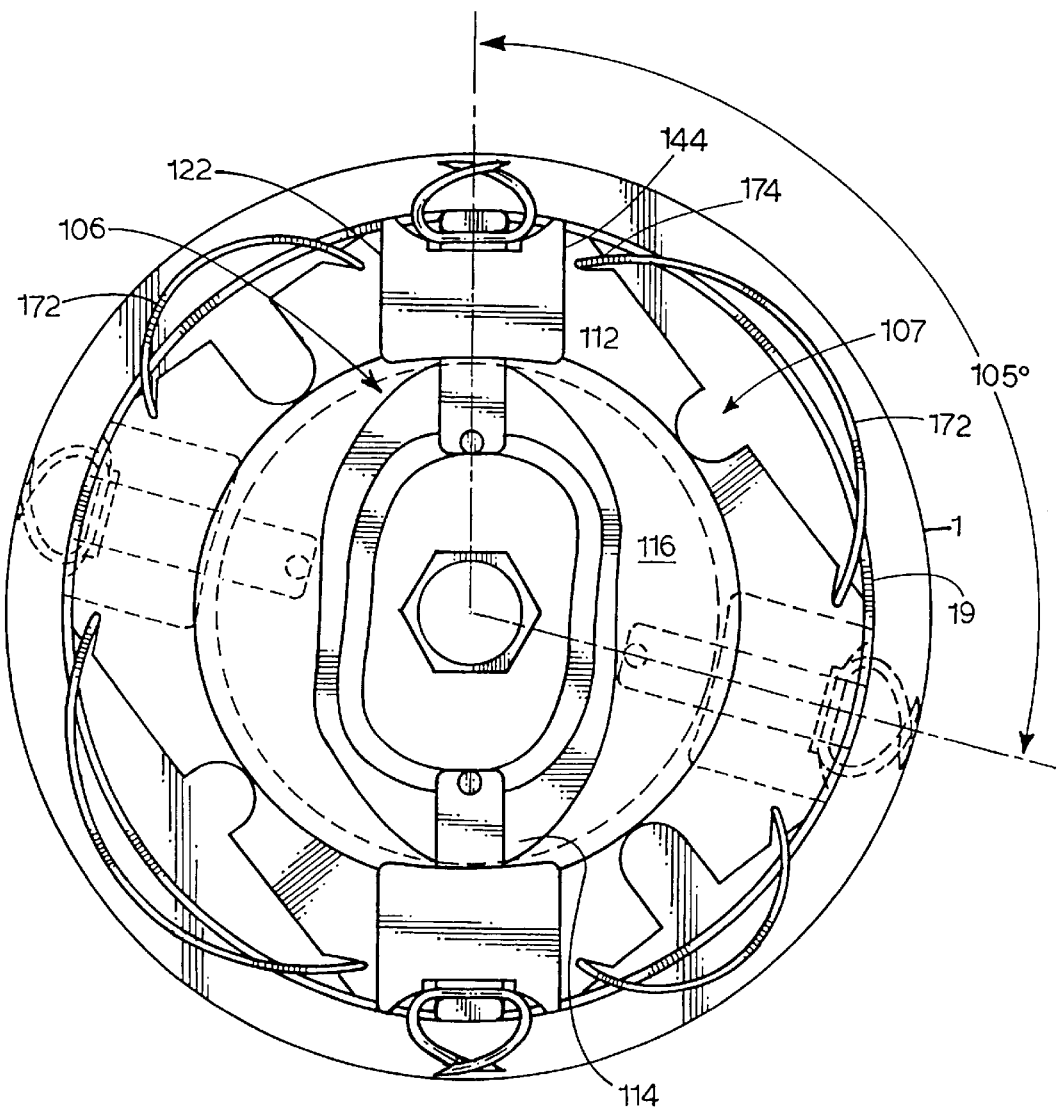
FIGS. 11, 12, 13 and 14 illustrate the various positions of the staple driving mechanism during operation of the fastener driving tool of the present invention.
Figure 14:
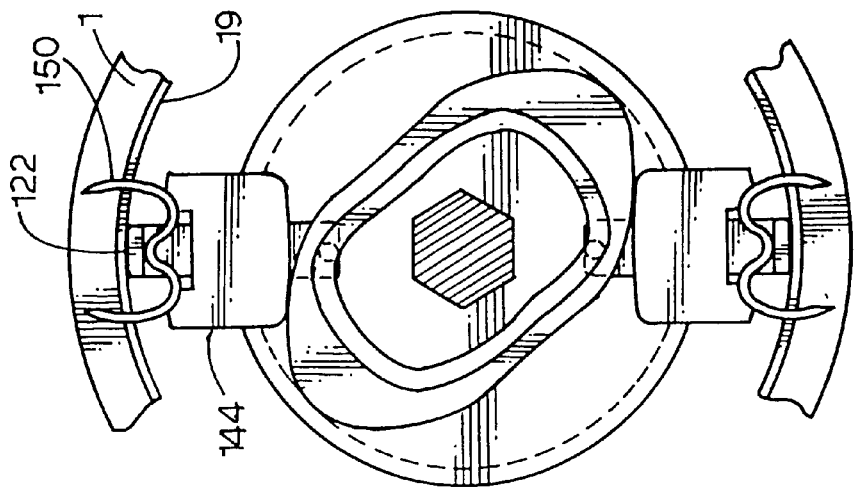
Figure 13:
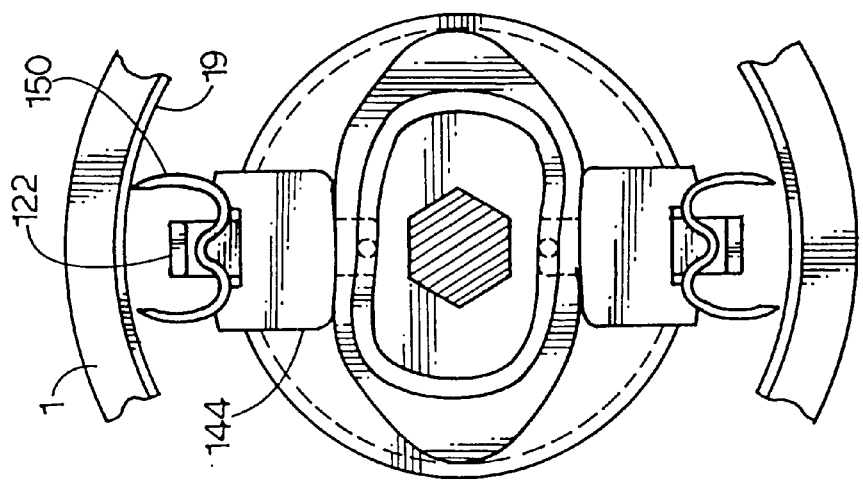
Figure 12:
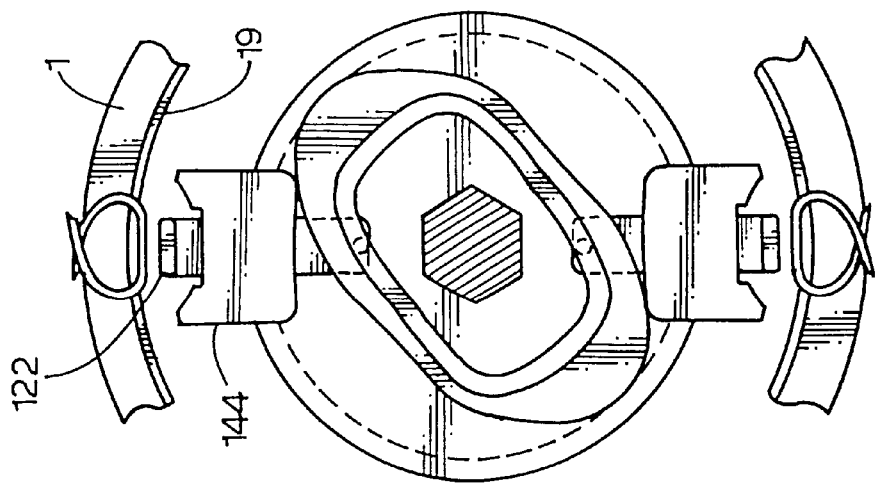

A cam 106 is mounted on surface 108 of cam plate 90 and has an elastomeric band 110 thereon. The cam 106 is shown in FIGS. 10–12 and rotates with the cam plate. The cam has two lobes, 112 and 114 spaced apart by 180° as well as a groove 116 defined therein for a purpose that will be understood from the ensuing disclosure. The cams are rotated with respect to the driver head plate 68 whereby each cam lobe passes each slot 80 and 82 once each revolution of the drive shaft 56. As will be understood, each revolution of drive shaft 56 thus drives two fasteners from the top surface of driver plate and two fasteners from the bottom of the driver plate. In this manner, even pressure is placed on the cuff and tissue during each fastener driving step because the slots are offset from each other by 180° on each surface of the driver plate. This keeps the cuff and tissue from puckering due to unbalanced fastener driving forces.

Each of the slots 80, 82, 84 and 86 has a fastener driver mechanism 120 accommodated therein. All of the fastener driver mechanisms are identical, therefore, only one mechanism 120 will be described. Mechanism 120 includes an anvil 122 mounted on driver plate 68 to slide thereon, with movement of the anvil in a direction that is longitudinal with respect to the anvil being radial with respect to the driver plate. The anvil includes a pin 124 that is slidably received in groove 116 defined in the cam so the anvil is moved into and out of the slot as the cam rotates. This anvil movement is timed so fasteners can be driven without jamming. A lifter spring 130 is mounted under the driver plate to remain stationary on that plate whereby the anvil moves with respect to the lifter spring. A driver 144 is slidably mounted in the slot and is attached to the cam lobe by ring 110 engaging both the cam lobe and a rider 111. The driver moves radially of the driver plate and is held against chordal movement with respect to that driver plate. Therefore, rotation of the cam plate moves the driver 144 radially inwardly and radially outwardly with respect to plate 68. The groove 116 is formed so that driver and anvil movements are in timed relation to each other. The driver includes two fastener-engaging tips 140 and 142 which are separated by a U-shaped opening 144 having an anvil-receiving notch 146 located therein.

A stack 148 of fasteners, such as staple 150, is contained in the housing to feed fasteners between the driver head and the anvil in a manner that is timed to place a fastener in driving position prior to the driver head moving radially outward in a fastener driving movement. Opening 144 is sized and shaped so that lifter spring 130 moves a driven fastener off of the anvil prior to the anvil moving arcuately away from the driving location and prior to a new fastener moving into the driving position between the driver and the anvil. A stack spring 152 is anchored to the housing section 52 by projection 66 and maintains force on the fasteners that is directed to feeding fasteners to a fastener-setting location after a previous fastener has been driven through the cuff and into the tissue. The anvil folds the fastener in a manner such that the sharp points 162 of the fastener drive directly through the cuff and the tissue rather than tear through the cuff and tissue. The anvil then folds the fastener after that fastener has pierced the cuff and the tissue to establish the closed fastener. Each stack spring also has an anti-retrograde spring 166 thereon. Spring 166 engages cleats 94 on the cam to prevent the cam from moving in an undesired retrograde direction. Fasteners are retained into the housing via recesses or doors, such as pocket 170. Each stack spring 152 also has two wings 167 that engage slots 168 defined in the driver plate to maintain the stack spring in the proper orientation and position to feed the fasteners, yet which will permit the stack spring to be removed via the door 170 to load fasteners. However, the preferred form of the tool is disposable.

As above discussed, it is a significant advantage of the tool T that the cuff is maintained in constant contact with the tissue during the fastener setting procedure. This advantage is realized by means of cuff dilation means, such as spring 172, mounted on the driver plate and extending radially outward from the outer peripheral edge of that driver plate. The springs curve gently outward and inward in a U shape to gently engage the cuff from the inside of that cuff and gently urge it against the tissue. The springs are mounted on the driver plate by spring-receiving slots, such as slot 174, defined in the outer peripheral edge of the driver plate so the spring is maintained on the plate and in the desired orientation.

For purposes of clarity, four positions of the fastener driver mechanism are shown in FIGS. 11, 12, 13 and 14. Beginning a cycle, a fastener has been driven through the cuff and the adjacent tissue, and is formed in FIG. 11 when the driver forces the fastener against the anvil. As the drive shaft is further rotated, the cam lobe moves from the FIG. 11 position to a retracted position shown in FIG. 12, with the anvil being pulled back after the set fastener has been pushed off that anvil by the lifter spring 130. Continued rotation of the drive shaft rotates the cam lobe into a loading position shown in FIG. 13 during which time, a new fastener is fed between the anvil and the driver. Further rotation of the drive shaft rotates the cam into an advance position shown in FIG. 14 which forces the driver against the fastener and the fastener through the cuff and the tissue.

Once all of the fasteners have been set, sutures 32 are unfastened from the cleat 34 on the body 33, cut and loosened to permit the tool to be removed from the patient. Then means 28' is removed from the cleat on the tool. Then, tool 85 is removed from the patient which plays out activating means 27' to the outside of the patient. A prosthetic valve body 20 is then inserted into the patient using a tool T' shown in FIG. 20, and is placed in position adjacent to the cuff. The valve body is moved until the surgeon is notified by the indicating means that the body is in the desired orientation. The activating means 27' and 28' are then activated to pull the cuff over and against the body by the above-discussed action of the drawstrings. Once the drawstrings are operated and the cuff is held tightly against the body 20, the activating means can be severed and removed from the patient. The prosthetic valve is now in place. Any tools can be removed from the patient and closure can be effected. As above discussed, the fasteners will be continuous over the entire perimeter of the cuff thereby further ensuring that no leak paths will develop. The continuous nature of the fastener coverage is best understood by visualizing a unit vector UV as shown in FIGS. 3 and 4, which is centered at the center of the cuff and being two rows thick, that is having a thickness indicated in FIGS. 3 and 4 by dimension $t_v$. As this unit vector moves through 360°, it will never be out of contact with a fastener whereby the entire circumference of the cuff is fastened to the tissue. The horizontal orientation of the fasteners further contributes to this feature.

Figure 20:
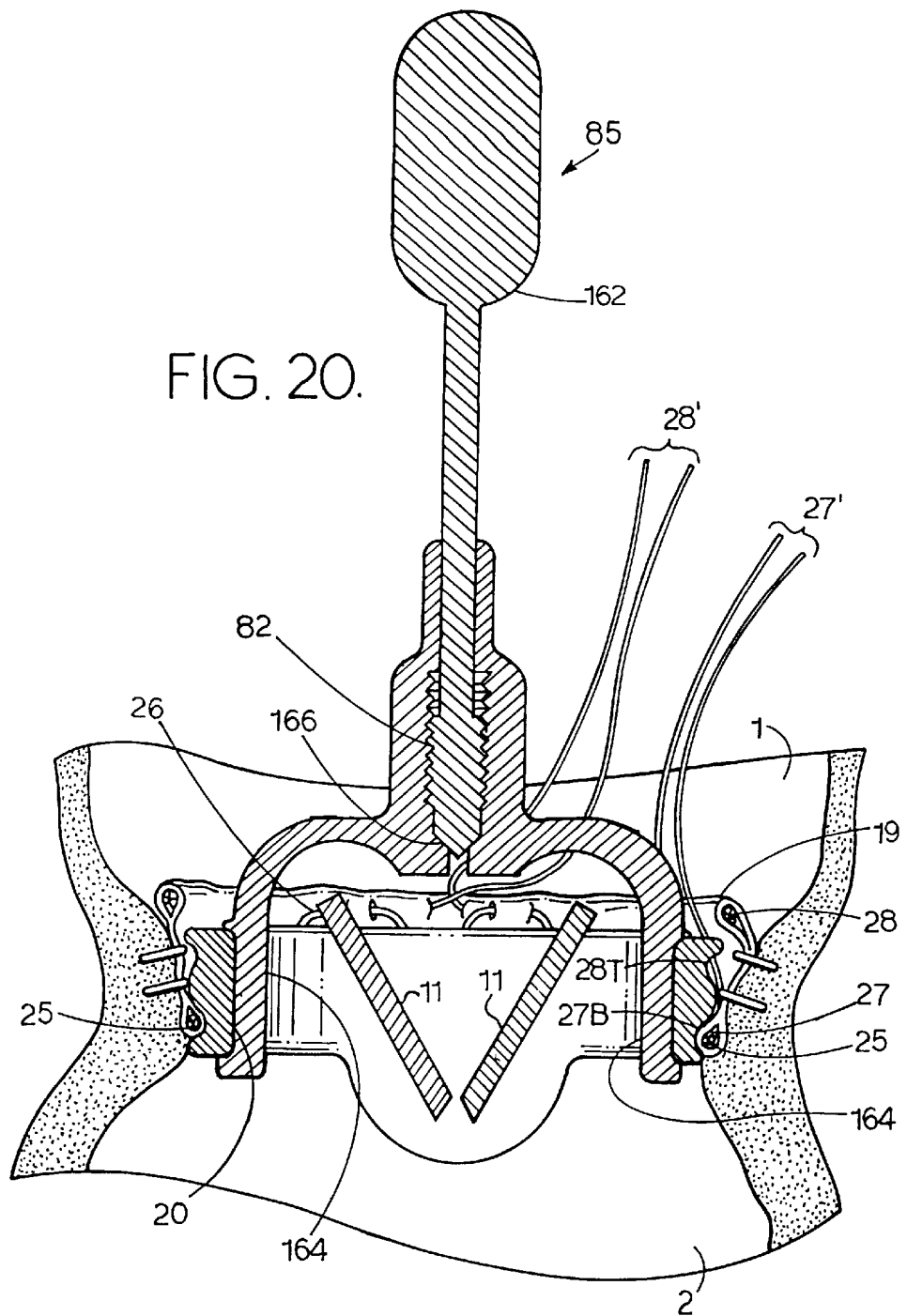
FIG. 20 shows a valve body holding tool inserting a valve body into an in-situ cuff.

As shown in FIG. 20, tool 85 includes a handle 162 and a pair of legs 164 which are spread apart by screwing handle 162 into the bottom of a holding fixture 164, forcing tapered edge 166 into the legs. The valve may then be inserted down into the cuff 19 until the garter spring 25 in the cuff is felt to detent into the lower recess 27B indicating proper seating of the valve body in the cuff.

Figure 16:
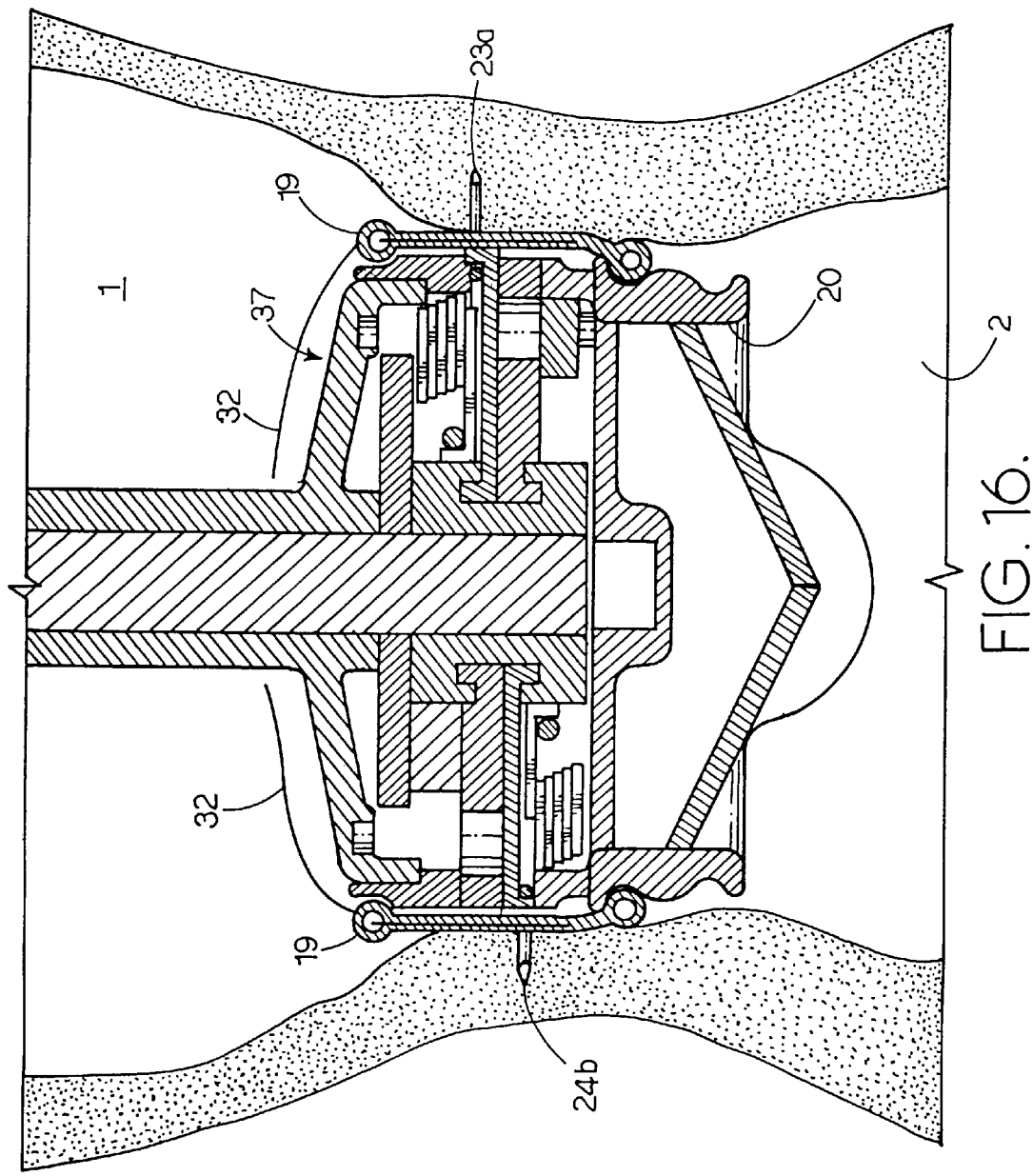
FIG. 16 shows the fastener driving tool in position after the cuff has been stapled to the patient and prior to movement of the valve body into position in the in-situ cuff.

An alternative form of the tool is shown in FIGS. 16–18 and maintains contact between the tool and the cuff whereby the cuff can be inverted after the valve body has been moved into position. The valve body is attached to the tool and to the cuff during fastening of the cuff to the tissue. After completion of the fastening step, the valve is pulled up thereby inverting the lower section of the cuff. The drawstrings are then cinched as above described.

Figure 28:
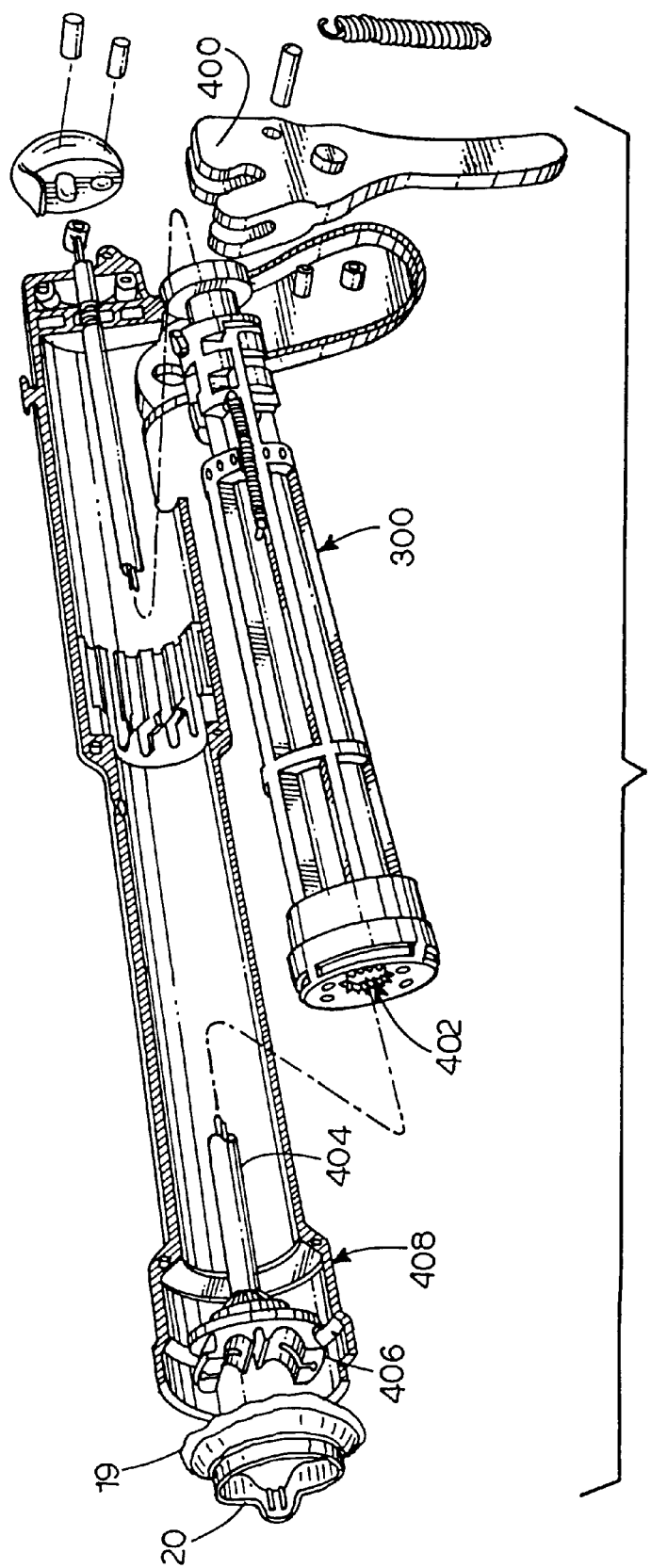
FIG. 28 is an exploded perspective view of another form of the tool which maintains the handle and shaft stationary during fastener delivery.
Figure 29:
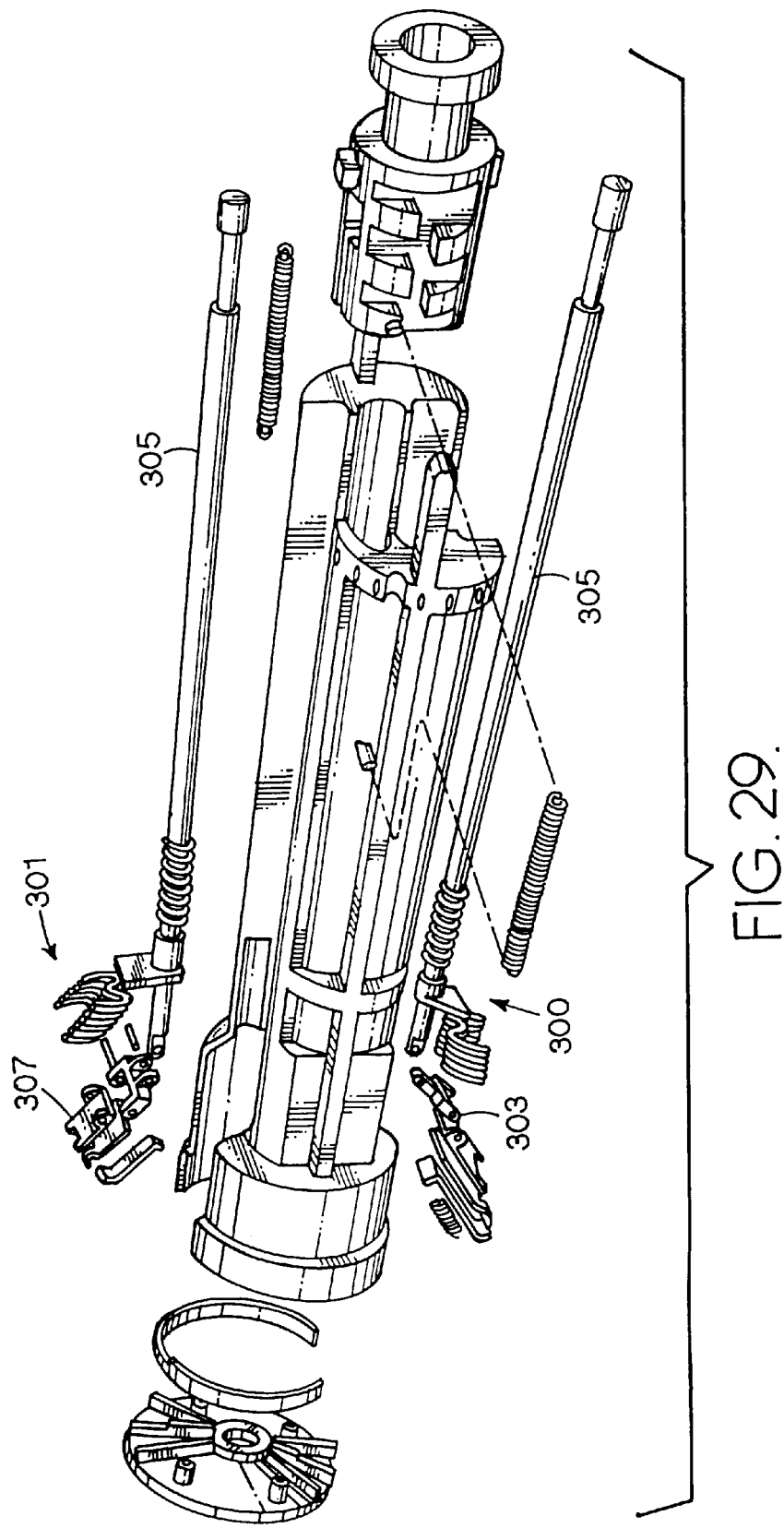
FIG. 29 illustrates a rotating fastener assembly for use in the tool shown in FIG. 28.
Figure 30:
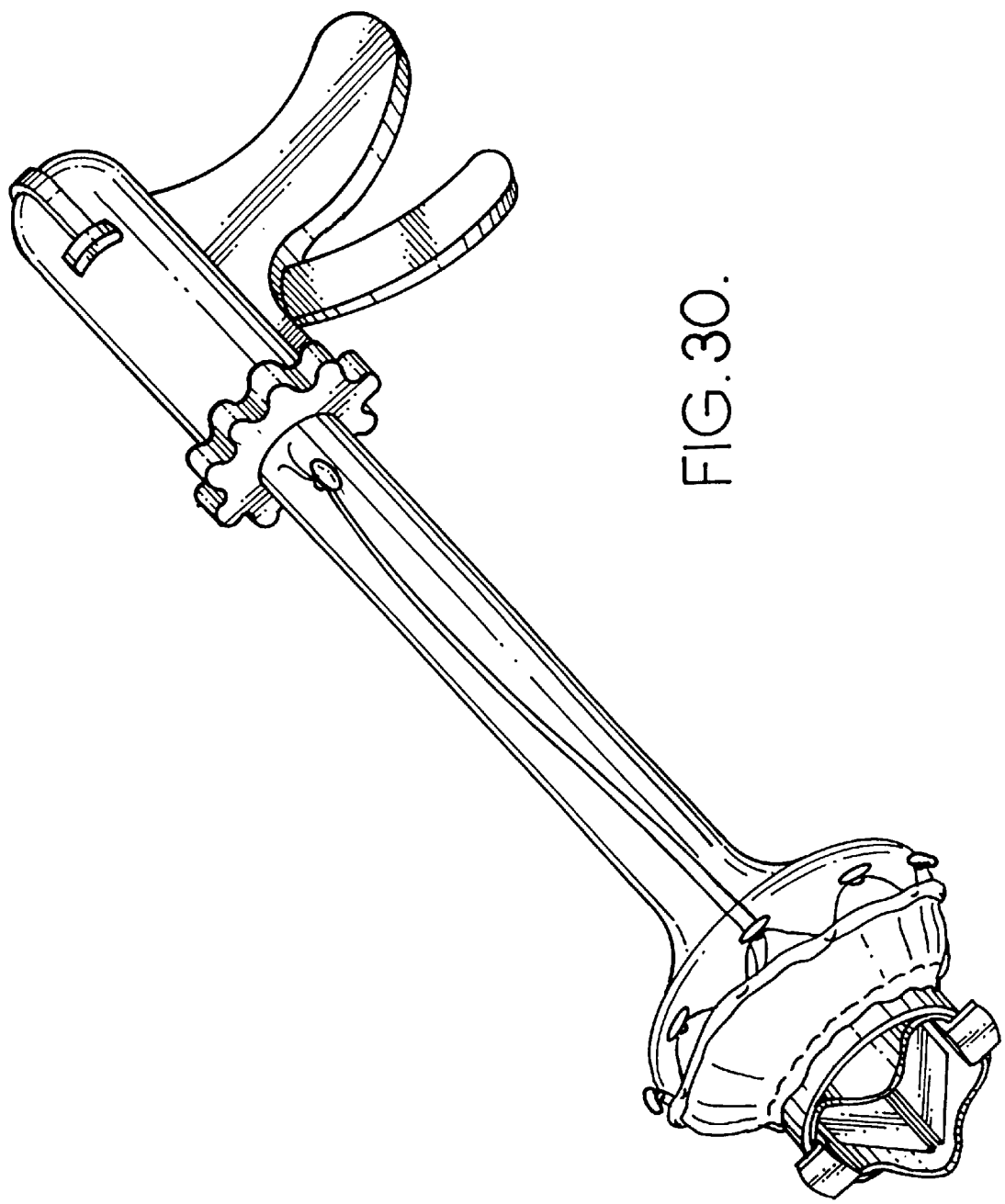
FIG. 30 is an assembled view of the FIG. 28 tool.

As above discussed, the central shaft experiences a counter-rotation as the driving head is indexed so the cuff is held stationary with respect to the patient's tissue while the fastener head is being indexed to the various positions. A further alternative form of the tool is shown in FIGS. 28 and 30 at T' and keeps the handle and the shaft stationary while the fastener delivery system rotates. A rotating fastener assembly 300 is shown in FIG. 29. Tool T' includes mechanisms necessary to deliver the fasteners and which are located inside the central shaft. A lever 400 actuates the mechanisms from within the housing. A central bore 402 is defined in the housing of the tool and has a central retaining stalk 404 therein on which the distal end 406 of the sewing cuff 19 is located. The heart valve base can also be attached to the stalk end 406 if the base is attached to the cuff 19 prior to setting the fasteners. The cuff is temporarily attached to the outer housing 408 and the stalk 404 which remain stationary during the fastening procedure and the fasteners are delivered in a coaxial method from between two stationary parts. Within the central fastener delivery assembly 300 are components similar to the above-described cam mechanisms needed to drive staples through the cuff and form them in the annular tissue from within. As above described, driver mechanisms 301 are diametrically opposed and offset with respect to each other to create the appropriate overlapping staple spacing discussed above. Staggering allows two distinct rows of staples to be formed as above discussed whereby total coverage of the cuff is effected. Toggle links 303 are used and are connected to longitudinal drive rods 305. Drive rods 305 translate handle-generated forces into fastener delivery forces at the toggle links 303.

Each toggle link 303 is connected to a staple driver 307. The fastener assembly 300 is rotated a plurality of times to form the two rows of staples. Flexible shafts (not shown) can also be used to permit the driving angle of the fasteners to be altered as necessary. Flexible shafts can also be used to permit the tool to operate to drive fasteners from the superior to inferior side of a suture cuff which might be pre-attached to the valve body. Such a cuff could be temporarily tied to the stationary housing. Upon insertion of the valve, cuff and instrument would be inserted into the annulus. Each fastener would form from the superior side of the cuff penetrating the cuff and annular tissue below. Again, as above discussed, one or more complete rows of fasteners would be formed holding the cuff to the annular tissue.

A balloon B (see FIG. 24) is used as a means for anchoring and positioning. Balloon B can either be attached to the fastener driving device or be separate. The balloon can be inflated using a hand pump HB. The balloon is pulled up snugly under the annular tissue and the device is brought down to it. Then, the tool can be drawn up close to the balloon trapping the annular tissue and aligning the tool for forming fasteners.

Figure 25:
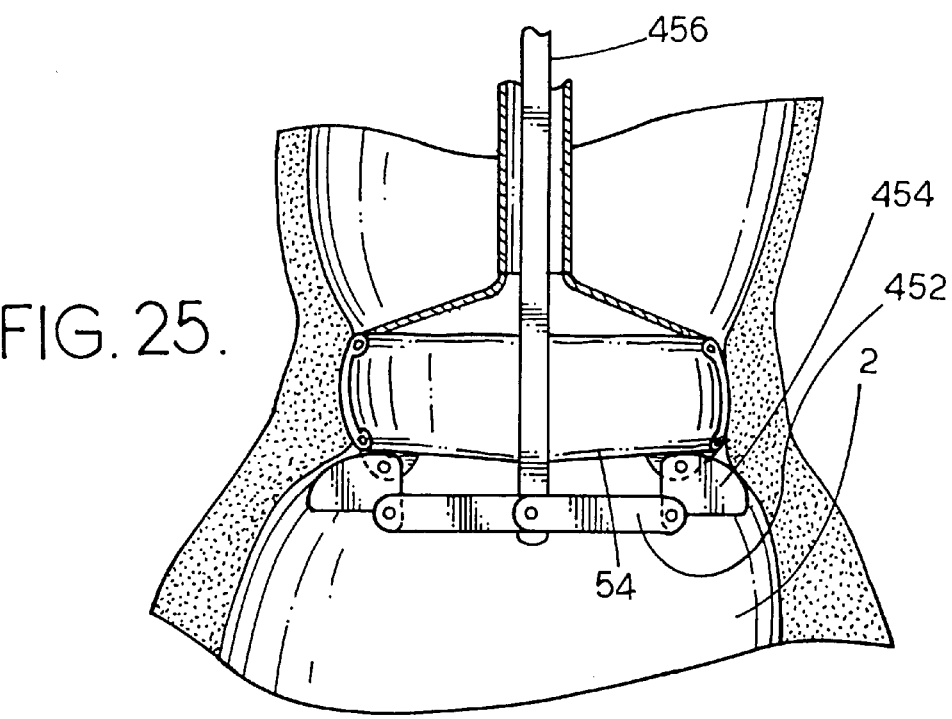

A second method (see/FIG. 25) uses levers 450 and links 452 to deploy small flanges 454 around the lower periphery of the lower housing 54. By actuating a central rod 456, the connecting links pivot the flanges outwardly providing a lip in which the surgeon can draw the tool upward locating the staples in the proper location in relation to the annular tissue.

Figure 26:
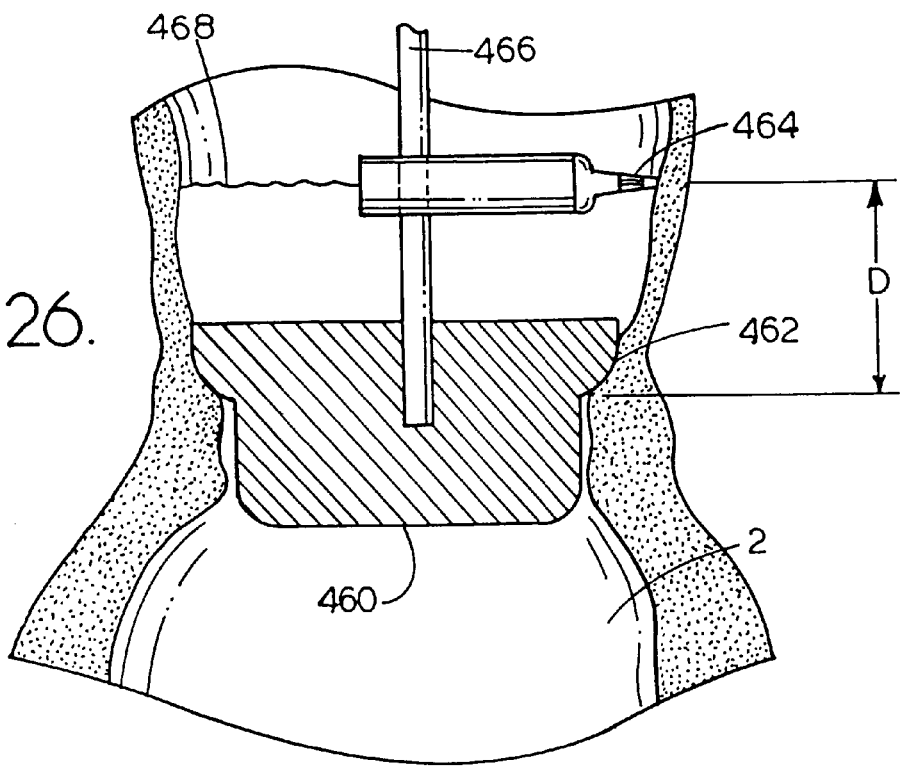

A third method (see FIG. 26) uses a clear cylindrical sizing tool 460 which uses a lip 462 or flange that sits on top of the annular tissue 464. It also has a special tissue marker mounted on a central shaft 466. The surgeon will visualize the contact of the annular tissue from above. The contact with the surface will create a wetted dark circle when properly seated on the annulus. At that point, the surgeon rotates the central shaft 466 which creates a line 468 inside the aorta. This line would have a distance D (FIG. 26) that would correspond to a pointer or landmark to be used to line up the device in the correct position.

Figure 27:
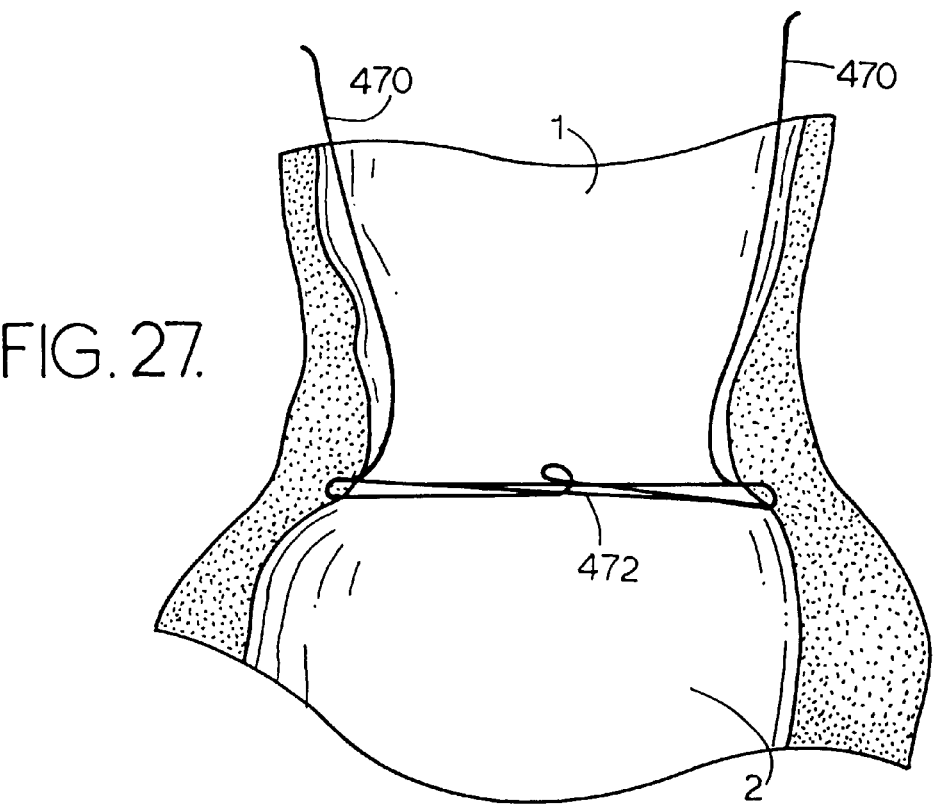

Still another way (see FIG. 27) to gauge the placement of the device is to drive sutures 470 below the annulus to create a safety net 472 that will not allow the device to plunge too deeply into the left ventricle 2. The device is then inserted until the resistance of the suture net is felt by the surgeon. Once the cuff is fastened into the annulus, the sutures can be cut and removed from the annulus.

In the interest of completeness, an open thoracotomy surgical technique for aortic valve replacement will now be discussed (see FIGS. 19A and 19B). A surgical incision 200 is made in one of several locations: a midline sternotomy incision; or a small anterior right or left thoracotomy; or a minithoracotomy (with or without rib removal); or a posterior thoracotomy; or a suprasternal or supraclavicular approach; or through port sites (mini incisions) over the chest wall. The pericardium is then opened. The patient is then placed on cardiopulmonary bypass using: right atrial cannulation; or femoral vein-femoral artery; or femoral artery-left atrium; or aortic-left atrial cannulation. The aorta is dissected for access and clamping. The aorta is then crossclamped and cardioplegia is delivered through: the aorta, coronary ostial cannulation or retrograde through the coronary sinus to arrest the heart. A venting device is then inserted.

The aortomy is then performed. The aortic valve is excised and the annulus, aorta and/or the anterior leaflet of the mitral valve, and septum are debrided as necessary and appropriate. A device or devices that determine the relative size of the annulus and that identify the position of the staples and stapling device, is inserted into the annulus. When appropriate, sizing and positioning are determined, a biologic marker is circumferentially traced over the top (most superior) edge of the position/sizing device, to guide the proper placement of the stapling device. A balloon or levers can also be used.

The position/sizing device is then removed and the stapling device is inserted and positioned in the annulus with the cuff of the valve. The stapling device is positioned with the cuff lying in the annulus and the position confirmed by its proximity to the circle previously marked. The stapling device is enabled to dilate the annulus with the valve cuff in situ.

The stapling device is then actuated. The appropriate size of mechanical valve skeleton is then inserted into the cuff. The valve and the perivalvular area are tested for proper size and the device is removed. Once the proper size is established, the skeleton is removed and the valve base is inserted. The drawstrings of the cuff are then tightened and tied securely to trap the mechanical valve to the cuff. This assures that the largest desirable valve base will be used. The aortomy is closed with traditional sutures or with vascular staples. The heart is de-aired and the crossclamp removed. The patient is then removed from cardiopulmonary bypass and the wounds are closed.

An alternative technique with the valve pre-attached includes the following steps. All methods up to and including placement of the biologic marker circumferentially over the top edge of the position/sizing device are repeated. Then, the position/sizing device is removed. The stapling device already pre-attached to a mechanical or tissue valve of appropriate size is lowered into the annulus. The stapling device and the cuff of the valve are positioned in the appropriate place in the annulus using the biological marker circle previously marked on the aortic wall for verification. The cuff-valve border at this time would be found in a slight subannular position.

The stapling device is then actuated. The drawstrings in the cuff of the valve are drawn and tied securely to bring the valve in proximity to the annulus. The remainder of the steps are the same as above described.

Yet a third technique for aortic valve replacement is through the left atrium. This technique includes the following steps: surgical incisions are made in the manner discussed above; the pericardium is opened; the patient may or may not then be placed on cardiopulmonary bypass. The technique then includes the use of imaging devices (both intra and extra-vascular) being used to guide the conduct of the operation. Purse string sutures (access) are then placed on the left atrium and aorta. Flexible imaging devices and instrumentation is then inserted through the left atrium (and aorta). The devices are lead through the mitral valve and into the left ventricle. The aortic valve is then imaged both through the aorta and left ventricle and is excised. The valve stapling device is then inserted through the left atrium and positioned in the aortic annulus. The stapling device is then activated and positioning assessed both through the left ventricle and aorta using the imaging devices. The stapling device is then removed, and all cannulation sites secured. The heart is then deaired and taken off cardiopulmonary bypass if appropriate. The wounds are then closed.

Figure 19A:
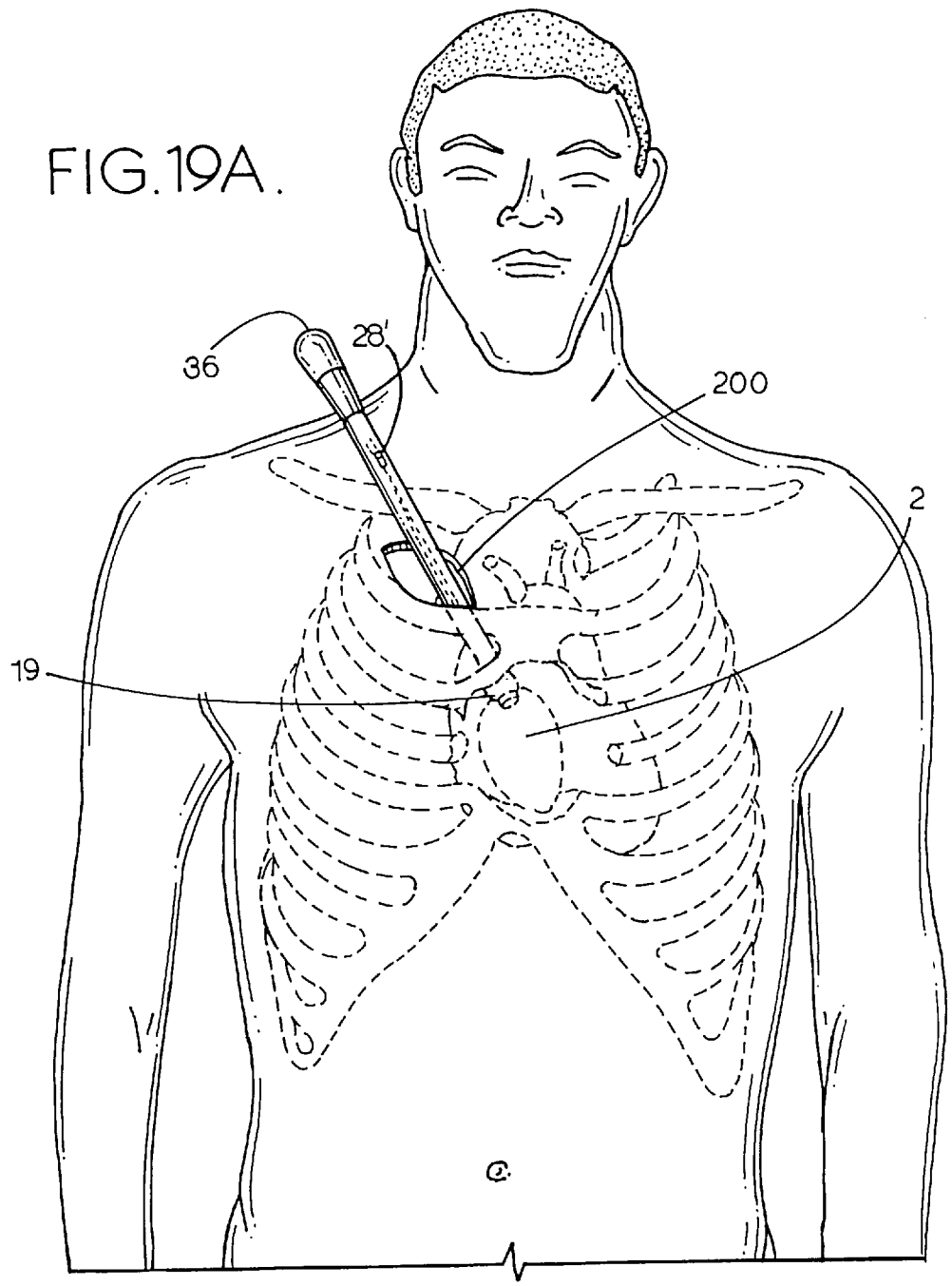
FIG. 19A illustrates the torso of a patient having the prosthetic valve of the present invention being placed using a fastener driving tool of the present invention in a minimally invasive surgical procedure according to the teaching of the present invention.
Figure 19B:
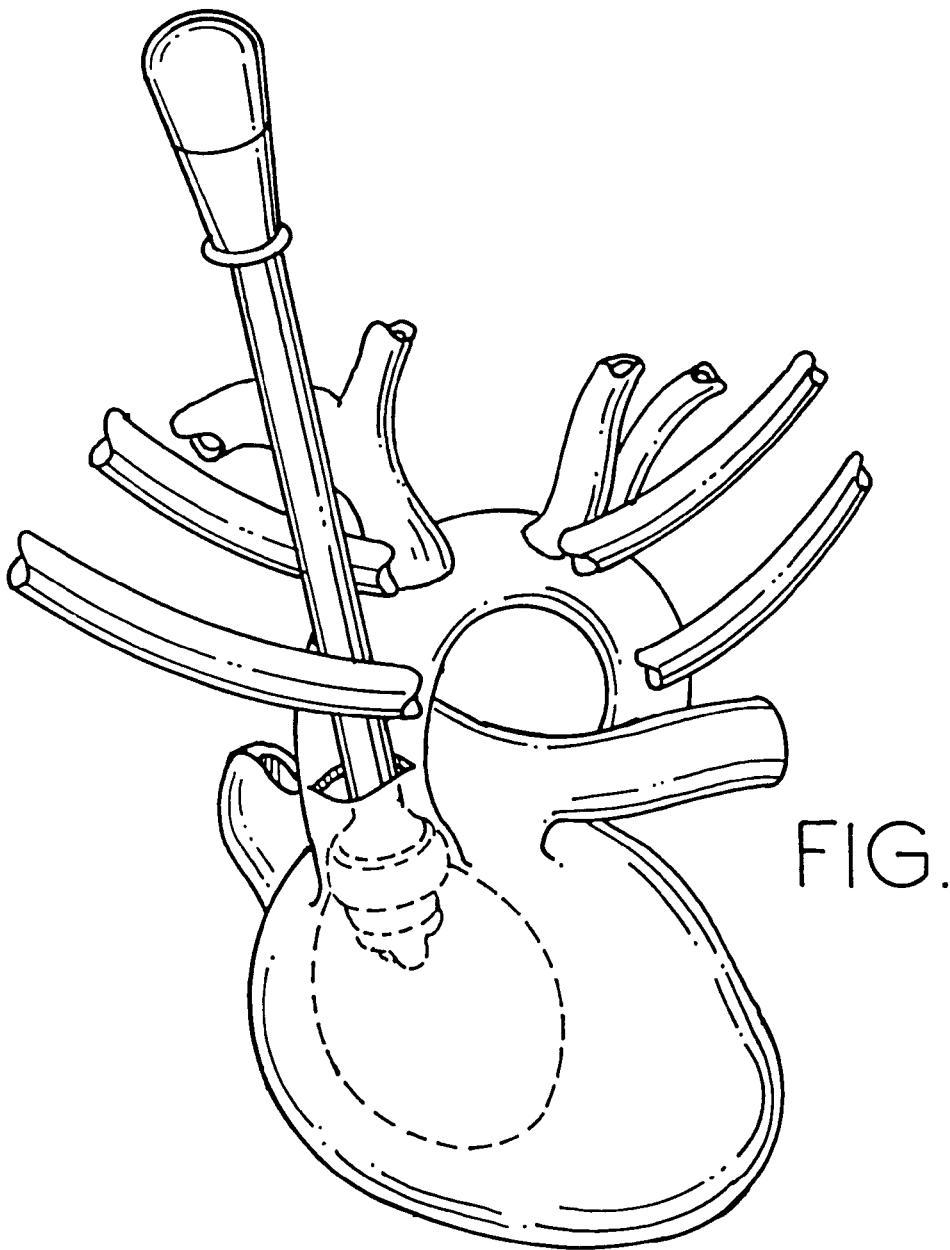
FIG. 19B illustrates the tool inserted into an aorta.

A minimally invasive surgical procedure is illustrated in FIGS. 19A and 19B. A torso with an overlapping rib cage is shown. Access to the aorta is gained through an incision 200 in the superstenal notch passing below the manubrium or via a mini-thoracotomy is performed in the area of the first and second ribs enabling visualization of the aorta. A small incision 202 across the aorta above the annulus is made. The fastener driving tool T with a cuff attached is inserted through the incision after the faulty valve has been excised. The knob 36 is rotated while holding the handle 35 to deploy the fasteners through the cuff 19 and into the aortic annulus. Once the fasteners have been driven into the aortic annulus, the stay sutures 32 are removed from cleat 34 allowing the head of the instrument to be removed from the patient's body. Activating means 27' and 28' are also removed from the cleats 27a" and 28a". The heart valve body is then placed into a holding fixture, such as the above-discussed fixture, and inserted into the aortic annulus in the same manner as the tool T. The valve body is then docked into the sewing cuff 19. The indicating means provides tactile feedback for the surgeon to determine when the heart valve body 20 is properly seated. Temporary stays 32 prevent the heart valve base from descending too far and aligning the drawstrings with the recesses in the valve body. Once the lower drawstring has been cinched up, the upper drawstring is pulled tight. The zig-zag drawstring 26 will then pull the cords into the top recess 28T.

Figure 23:
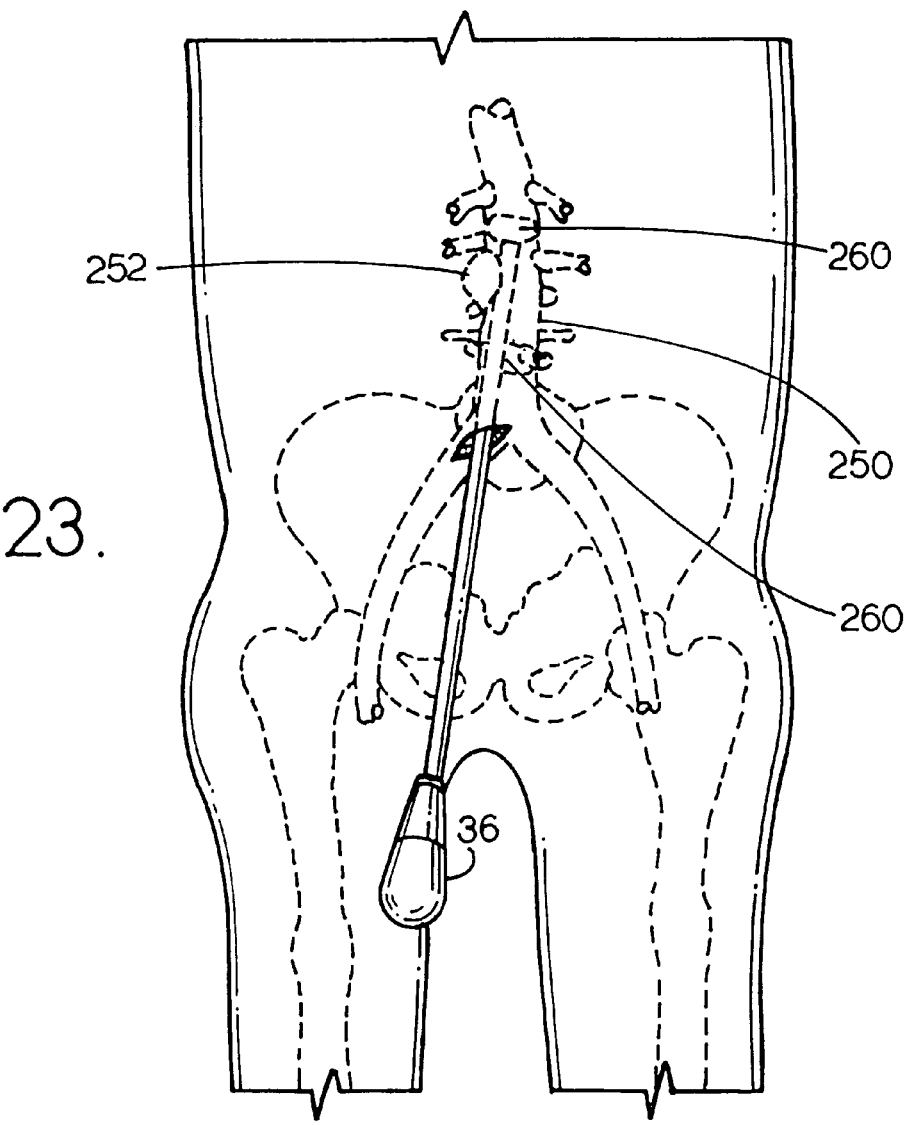
FIG. 23 shows use of the tool shown in FIG. 21 to repair an abdominal aortic aneurysm.

As shown in FIGS. 21–23, the system can be used to repair an abdominal aortic aneurysm (AAA) which may occur because of a thinning of the aortic wall 250. The wall balloons out under positive pressure and forms a pouch 252. These aneurysms present life-threatening consequences for the patient should they rupture. If detected prior to rupture, a graft 254 can be placed on the aorta, in an abdominal graft procedure to provide support to the weakened area of the wall. The graft is usually made from a tube of Dacron fabric and is most often sutured in place.

However, using the teaching of the present invention, the graft can be stapled in place. As shown in FIGS. 21 and 22, the dilating fastener deployment feature of the present invention permits fasteners to be formed from the inside toward the outside of the aortic wall. As shown in FIG. 21, the fastener deployment device has two driving heads 260 to deliver fasteners through the graft on either side of the aneurysm 252. At each end of the graft in FIG. 22 there is a metal ring 266, analogous to the garter spring discussed above. These rings help to keep the graft open once it is fastened to the aortic wall. FIG. 23 illustrates access to the aorta gained through entry in the femoral artery in the pelvic region. The fastener deployment device, with graft attached, would be inserted into the femoral artery and fed up to the area of the aneurysm. The distal head 260 is positioned beyond the aneurysm and the proximal head 260 is positioned to center the aneurysm underneath the graft. Fasteners are formed in a manner similar to that discussed above, completing the installation of the graft. Stay sutures may be used to hold the graft in place during fastening.

Figure 24:
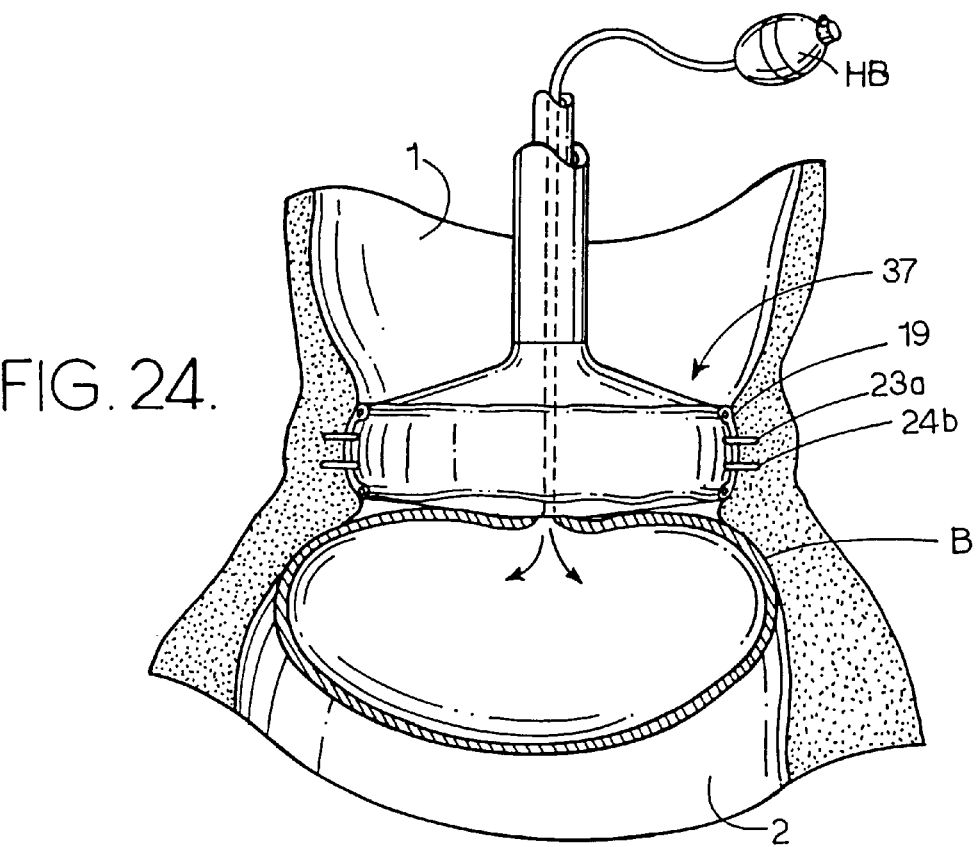
FIG. 24–27 show steps in placing a prosthesis.

During the installation of the fastener driving device, it will be important to obtain the correct anatomical positioning of the cuff to be fastened to the annular tissue. FIGS. 24–27 depict four different ways to accomplish this task. FIG. 24 shows the use of an inflatable balloon B in the left ventricle 2.

As discussed above, there are times when a surgeon wishes to use an articulated or curved shaft to accommodate anatomixal positioning of the instrument. As also discussed above, a curved shaft may be particularly advantageous in minimally invasive surgery where access to the proper fastening plane may be difficult or impossible with an instrument having a straight shaft. In such a case, instrument 600 shown in FIGS. 31, 36 and 37 is used to drive fasteners or staples radially outwardly. The advantage of the radial design is that it simplifies the delivery of longitudinal forces through the shaft of the instrument.

Referring to FIG. 31, it is seen that instrument 600 includes proximal end 602 that will be located outside the patient and which will be operated by the surgeon. Instrument 600 also includes a distal end 604 which will be located inside the patient and to which the cuff 19 will be attached and to which the heart valve 20 will be attached. A housing 608 can be articulated or flexible so the overall instrument can be bent as needed. Proximal end 602 contains an index mechanism 610 and a hand wheel 612.

As can be seen in FIGS. 31 and 41, a pre-fire rod 614 includes a handle 616 and a body 618 which is accommodated in a bore 622 defined through hand wheel 612 and through housing 608 to have its distal end 620 located near distal end 604 of the housing for a purpose that will be understood from the ensuing discussion. As will be understood, there are aligned bores in instrument 600 so pre-fire rod 614 will extend through instrument 600 from proximal end 602 thereof to distal end 604 thereof.

Index mechanism 610 includes a bracket 624 which is held stationary with respect to the patient during an operation. Bracket 624 is U-shaped and has two legs 626 which are connected together by a central leg 628. An index alignment plate 630 is attached to the distal ends of the legs 626 and includes a plurality of angularly spaced apart index alignment holes, such as hole 632. Housing 608 is attached to surface 634 of the index alignment plate 630. holes 632 are spaced apart a predetermined angular spacing as determined by the needs of a surgeon as will be understood by one skilled in the art based on the teaching of this disclosure.

Two index pins, such as pin 638, are mounted on a lower surface 640 of a wedge cam driver plate 642 which has an upper surface 644. Plate 642 is rotatable with respect to plate 630 whereby index pins 638 can be moved from one index hole 632 to another index hole. Two wedge cams 646 and 648 are each attached at one end thereof to the driver plate 642 to rotate therewith and each has a wedge shaped distal end 650 and 652 respectively. Each distal end 650 and 652 has a terminal end, such as end 654 of end 648 and a surface, such as surface 656 of end 648, that slopes outwardly from end 654 along the longitudinal direction toward proximal end 602. As driver plate 642 is moved in longitudinal directions 660 and 662, ends 648 and 650 are moved in corresponding directions. The purpose of this movement will be understood from the ensuing discussion. Each of the wedge cams includes an inner edge 664 and 666 that is spaced apart from the corresponding inner edge of the other wedge cam so that a gap 668 is defined therebetween. Pre-fire rod 614 is accommodated in gap 668 so that distal end 620 of the pre-fire rod is located adjacent to ends 654 of the wedge cam bodies.

The pre-fire rod is forced in directions 660 and 662 by moving handle 616 in the desired direction. Wedge cams 646 and 648 are also moved in directions 660 and 662 by movement of driver plate 642. Driver plate 642 is moved by turning hand wheel 622 in directions 670 and 672. A threaded shaft 674 is attached to hand wheel 612 to be rotated thereby and includes a distal end connected to driver plate 642. Shaft 674 is threadably accommodated in leg 628 of the bracket 624 to move in directions 660 and 662 in response to the rotational movement of the hand wheel 612 in directions 670 and 672. Shaft 674 is coupled to driver plate 642 to move that plate in directions 660 and 662 but to rotate relative to the plate so the plate does not rotate with the hand wheel. A suitable de-coupling joint is used to effect the connection between shaft 674 and plate 642.

Operation of the fastening tool described thus far is understood from FIG. 41. Thus, the wedge cam sloping surfaces 652 are oriented by disengaging index pins 638 from alignment holes 632, rotating driver plate 642 until the index pins are aligned with the selected holes, and then operating hand wheel 612 to move in direction 660 until the index pins are suitably seated in the selected index holes. Pre-fire rod 614 is then forced through the longitudinal bore until distal end 620 thereof is suitably positioned engaging all driver assemblies. The pre-fire rod extends the drivers and staples to force the cuff against the tissue. In addition, the legs of each staple protrude through the cuff into the tissue thereby coupling the instrument to the tissue. Further operation of the hand wheel will operate the fastener mechanism as will be described below.

As discussed above, the staple mechanism includes a plurality of staple assemblies 680 that are angularly spaced apart as shown in FIG. 36. The staple assemblies are also located in two rows that are spaced apart longitudinally of the instrument as indicated by rows R1 and R2. The assemblies are also offset so staples in row R1 are staggered with respect to staples in row R2.

Figure 32:
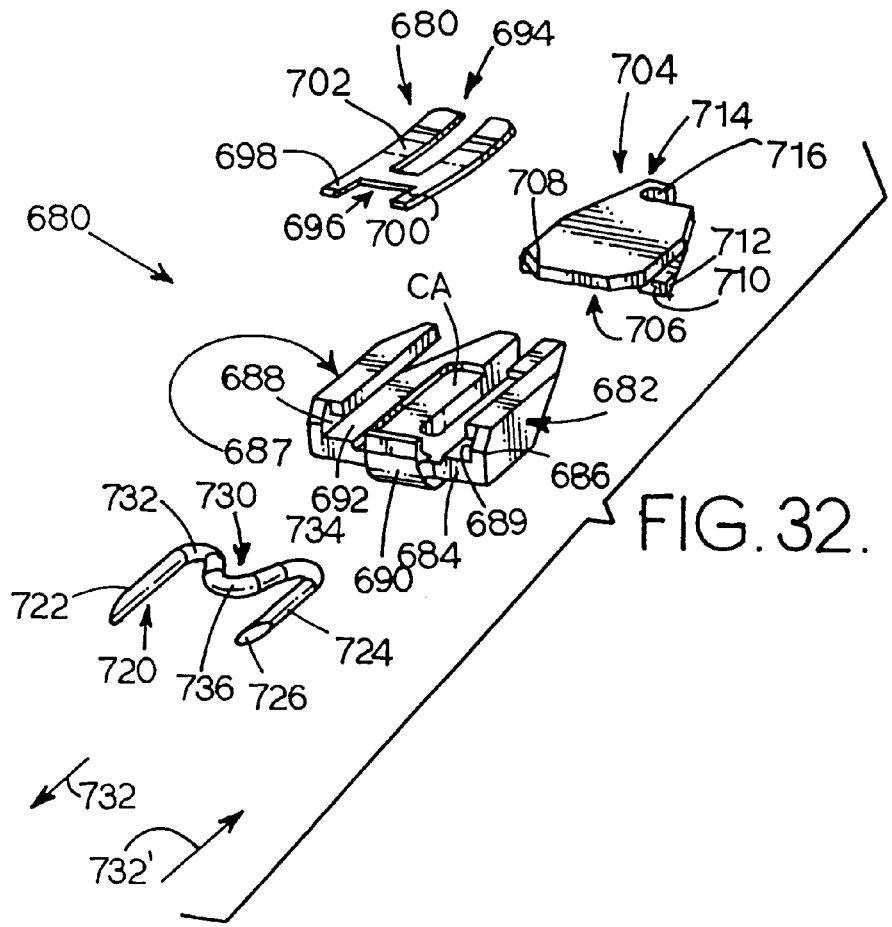
FIG. 32 is an exploded perspective view of a staple delivery assembly.

The assemblies are all identical therefore only one assembly will be described. As shown in FIG. 32, assembly 680 includes an anvil frame 682 having a base section 684 having sides 686 and 687 each having an inner surface 688 and 689 to define a cavity CA therebetween. A center anvil 690 is located centrally between the sides and extends upwardly above base surface 692. A lifter spring 694 is H-shaped and includes a U-shaped front end 696 with two legs 698 and 700 extending therefrom. Spring tabs 702 are located on the other end of each leg. The lifter spring is curved so front end 696 curves upwardly from base surface 692 when the lifter spring is seated thereon. Spring tabs 702 engage the anvil frame to hold the spring in place in the cavity CA. End 696 will be located adjacent to center anvil 690.

Figure 33:
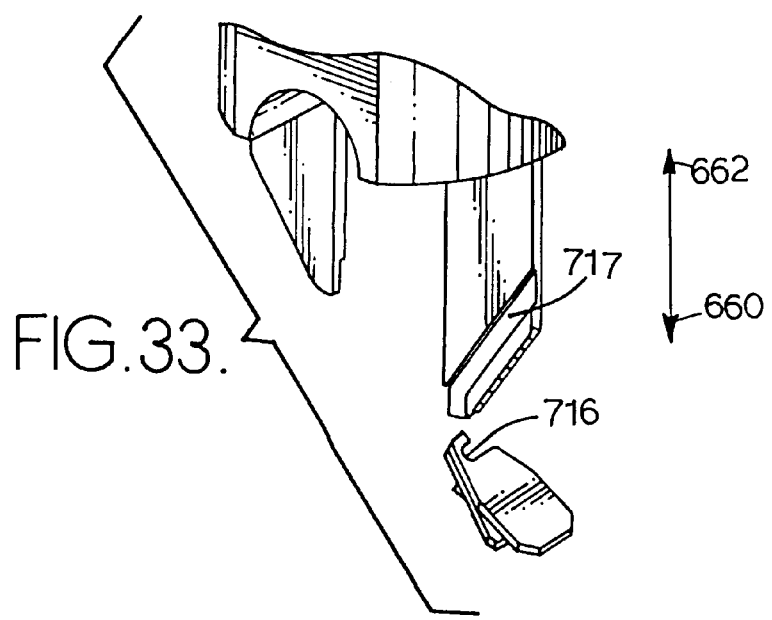
FIG. 33 is an exploded perspective view of a staple guide means for guiding movement of the staple delivery assembly shown in FIG. 32.

A driver 704 is wedge shaped and is received in cavity CA. Driver 704 includes a front edge 706 having two surfaces 708 and 710 thereon with a driver stop 712 on an undersurface thereof. The legs 708 and 710 will be located adjacent to center anvil 690 when the driver completes a fastener driving step as will be understood from the following discussion. An engaging element 714 extends rearwardly from the driver 704 and includes a hook 716 for engaging a corresponding groove 717 (see FIG. 33) defined in each of the wedge cams.

A W-shaped staple 720 is received in cavity CA and includes two legs 722 and 724, each having a sharp tip, such as tip 726 that is forced through the patient's tissue and through the cuff. The staple further includes a doubly curved center section 730 having a first curve 732 and 734 connecting each leg to the center section and a central curve 736. The central curve 730 is located to be engaged by center anvil 690 when the staple is forced in direction 732 by driver 704 engaging curves 732 and 734. Legs 722 and 724 slidably engage surfaces 688 and 689 to be held straight during the movement in direction 732 until the legs leave the anvil frame. Legs 722 and 724 are parallel and pierce the article being stapled before they are folded over through contact of the section 736 with center anvil 690.

As can be understood from the foregoing, as staple 720 is forced in direction 732, legs 722 and 724 move in direction 732 in sliding engagement with surfaces 688 and 689. After staple center section 736 engages center anvil 690, further movement in direction 732 causes the legs 722 and 724 to fold towards each other until they overlap each other. This is a two step movement of the staple: a first linear movement of the legs; and then a folding over of the legs. The first linear movement causes the legs to push through the tissue and the material of the cuff in a linear direction before the legs are folded over. Thus, the staple can take a significant bite of the material and the tissue before folding. This is helpful if the tissue is hard or is covered with calcium, and is also important to prevent bunching of the tissue.

The staple disclosed herein is narrow in its preform width and can resist gathering of the cuff and tissue during the forming process. Staple designs such as box staples gather and bunch material between the legs of the staples as they are formed. Bunching is inconsistent with the needs of this device. If a staple bunches, far too much material in the cuff is used (gathered) and by the time the staple pattern comes around to making a full circumferential line, the fabric is too tight and can pull away from the aorta wall.

Return movement of the assembly is indicated in FIG. 32 by arrow 732', and is caused by hook 716 being engaged in groove 717. The groove is sloped so that as the wedge cam is moved in direction 660, the driver is moved in direction 732, and as the wedge cam is moved in direction 662, the driver is moved in direction 732'.

An alternative form of the assembly is shown in FIG. 35 as assembly 680'. Assembly 680' is similar to assembly 680 except driver 704' includes a rear projection 734 and two forward projections 708' and 710' which engage curves 732 and 734 of the staple to drive the staple as described above. Assembly 680' includes a U-shaped lifter spring 702' which has two legs 698' and 700' with tabs 702' for engaging recesses 703 to hold the spring in the anvil frame. Assembly 680' is moved in direction 732 in the same manner as assembly 680, but includes a post 740 on top of a frame plate 742 that is fixed to the anvil frame. A garter spring 744 (see also FIG. 36) or the like is wrapped around the posts of the assemblies 680 to return them in direction 732'. Operation of assembly 680' is similar to the above-described operation of assembly 680.

Figure 34E:
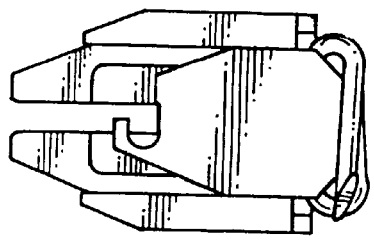
Figure 34B:
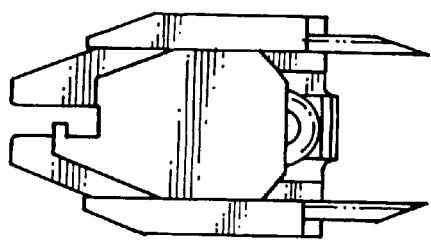
Figure 34D:
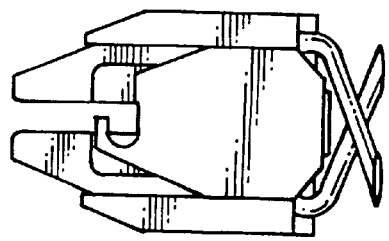
Figure 34A:
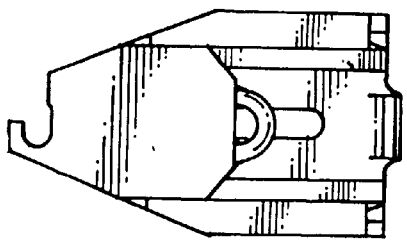
Figure 34C:
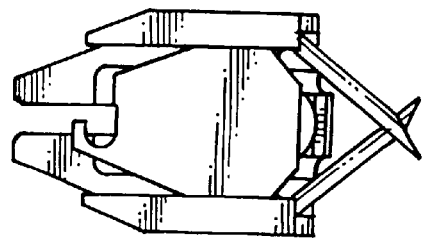

Operation of the staple is illustrated in FIGS. 34a–34e for assembly 680 and in FIGS. 34a'–34e' for assembly 680'. Thus, FIG. 34a shows a staple in a nested position, FIG. 34b shows the first step in which the legs of the staple are pushed linearly out of the anvil frame to advance the staple, FIG. 34C shows the crown or central curve engaging the center anvil to initiate the folding of the legs, FIG. 34D shows the legs being folded over and FIG. 34E shows the staple in its final form.

Operation of the instrument can be understood from FIGS. 36, 37, 38, 39a–39d, and 40A–40C. As shown, a wedge cam body 750 is slidably received in housing 608 and has wedge cams 646 and 648 thereon. The wedge cams are inserted into a wedge cam alignment block 752 via slots, such as slot 754. The wedge cam alignment block 752 is fixed to a head 756 by fasteners, such as threaded bolt 758. Head 756 contains all of the above-described assemblies 680 or 680' in staggered rows R1 and R2.

Wedge cam driver plate 642 is moved in direction 662 to release index pins 638 from index alignment holes 632 which moves the wedge cams out of the slots 754. The driver plate 642 is then rotated in direction 670 or direction 672 to align index pins 638 with new index alignment holes and thus align the wedge cams with new slots.

Hand wheel 612 is then rotated to drive plate 642 in direction 660 to set the wedge cams in the slots near the rear ends of the staple drivers. Pre-fire rod 614 is then driven down in direction 660 to move anvil frames radially outward into a pre-fire position, such as shown for staple 720' in FIG. 36 which drives the staple through the cuff material and through the tissue. A frame stop 760 is located on the bottom of each anvil frame and engages a corresponding shoulder in the instrument to stop movement of the anvil frame in direction 732 when the pre-fire rod moves past the anvil frame. Hand wheel 612 is then operated to drive the wedge cams in direction 660 which drives the staples in direction 732. This drives the staple through the cuff and through the tissue and folds the staple legs over as above discussed. The lifter spring then moves the folded staple over the center anvil 690 to release the staple from the assembly. A plurality of staples are stored in the instrument so another staple is ready for deployment as soon as the operation is complete.

The hand wheel is then rotated in the opposite direction, the pre-fire rod is left in place until all staples have been formed, then it is retracted, which releases the stretching force on the cuff and tissue which releases the instrument.

Operation of the instrument is shown in FIGS. 39a–39d and 40A–40C. FIG. 42 shows an anchor ring with three rows of staples being shown in a cuff 19. Once the staples are deployed, the heart valve can be moved onto the stapled cuff, and attached thereto as above discussed. This is illustrated in FIGS. 43–45. FIGS. 43, 44 and 45 show the sequence of attaching a heart valve prosthesis to the anchor ring. Prior to installing th ering, a set of running sutures are connected between th ering and the heart valve. Typically three suturs are used. A running suture is one which alternates between the anchor ring and the heart valve prosthesis. Note that in this embodiment the prosthesis has a cuff to capture the running suture. Other mehods of joining the anchor ring to the valve may occur to those skilled in the art based on the teaching of this disclosure. A running suture is not commonly used in valve attachment because it produces a weaker attachment than do individual sutures with felt pledgets. However, a running suture makes for faster attachment than individual sutures because there is less knot tying. In this case, thre is no concern for weakness in a running suture technique because each loop of suture is secured through cuff material at both ends. The anchor ring can have reinforcing material, such as material R, embedded in it in the area where tthe sutures will loop through. This will help spread the load out and create a better seal between the anchor ring and the prosthesis. As shown in FIG. 38, the staples extend through the cuff and into the tissue before they are folded over. Thus, as shown for staple 720a the staple legs extend deep into the tissue to get full depth bite of tissue before folding, and the cuff is stretched over the tissue as shown for tissue AT.

As above discussed, there are times when a surgeon wishes to apply one staple at a time so better control over the number and placement of the staples can be exercised. This can be achieve using instrument 800 shown in FIGS. 46 and 47.

Instrument 800 fires one staple at a time and can be positioned as desired prior to firing the staple. As will be discussed below, using instrument 800, a surgeon can establish any desired stapling pattern, either one preset on the cuff or one that the surgeon makes up on the fly. It is noted that the operation of the staple and the staple forming assembly of instrument 800 is basically identical to the staple and staple forming assembly discussed above. Therefore, only the differences between instrument 800 and the above-described assembly will be discussed.

Instrument 800 includes a hand-grip section 802 on the proximal end thereof, and a staple forming and deploying assembly 804 on the distal end thereof with a shaft housing 806 connecting the two ends. Hand-grip section 802 includes a handle 808 on which a forming trigger 810 is pivotally mounted for movement in directions 811 and 811', with return spring 812 biasing the trigger in return direction 811'. A drive bar 814 is connected at a proximal end thereof to trigger 810 to be moved in directions 811 and 811' with the trigger. Drive bar 814 is located inside housing 806 and has a staple driver 704" on the distal end thereof. Staple driver 704" is part of a staple driving and forming assembly 680" which drives staple 720 toward center anvil 690" to move the legs of the staple outwardly and through the cuff and the tissue and then to fold the legs over as above discussed. A lifter spring 694" ejects the staple after it has been formed. A plurality of staples are stored in a housing 816 on the distal end of the shaft, and a spring biased magazine guide 818 urges the staples under a transfer spring 820 mounted on shroud 822 which biases the staples into position to be moved by the driver 704" upon actuation of forming trigger 810. Operation of the staple forming assembly will not be discussed as it was discussed above with reference to FIGS. 34a–34c'.

As shown in FIG. 47, distal end 804 is angled so a staple exits that end at an angle Θ to the longitudinal centerline of the instrument. In the preferred embodiment, angle Θ is an acute angle. A flexible section 824 between drive bar 814 and driver 704" permits the drive bar to move linearly while forcing the staple at an angle to that movement. The purpose of this angled discharge is to permit the surgeon to accurately locate the staple being driven in the exact position he desires. As will also be understood from the following discussion, this angled discharge permits the instrument 800 to be used in conjunction with a plurality of different systems.

As just mentioned, a surgeon may want to locate each staple individually. He may use a guide or he may simply locate on the fly. One form of stapling guide system is shown in FIG. 48. Using this system, a cuff is first attached to the patient's tissue using the just discussed staple driving tool, instrument 800, in conjunction with a guide and support assembly 830. In the interest of clarity, a cuff that is installed on the patient separate from the heart valve will be referred to as an anchor ring. Once the anchor ring is installed on the patient, the heart valve is drawn to it in the manner discussed above, such as shown in FIGS. 43–45, for example. As shown in FIG. 48, an anchor ring 19' is releasably fixed to flexible fingers 832 of a cage, with the top of each finger being fixed to an index ring 834 and biasing outwardly from that ring. The anchor ring 19' is positioned on the lower ends of the fingers and is biased radially outwardly. The index ring 834 has lugs 836 that are fixed to a stationary stabilizer whereby the guide 830 is held stationary during the operation. The outward flex of fingers 832 force the ring 19' against the patient's tissue thereby ensuring a snug fit between the anchor ring and the patient's tissue, and can accommodate various sizes of aortas.

As can be seen in FIG. 48, anchor ring 19' includes a plurality of stapling icons, such as icon 838 to guide a surgeon in placing the staples. Using icons 838, a stapling pattern shown in FIG. 49 will be established in ring 19' with staggered rows R1, R2 and R3 of staples. To assist the surgeon in following the icons, index ring 834 includes a plurality of grooves, such as groove 840 which receive the instrument 800 and serve to position it with respect to an icon. If a surgeon wishes, he can staple in any pattern he wishes. This option is illustrated in FIG. 50A shows a scalloped staple pattern that generally follows the natural cusp shaped curves of a valve annulus could be selected if desired. Other patterns could also be selected as will occur to those skilled in the art based on the teaching of this disclosure.

As above described, the legs of each staple are first extended to pierce the cuff and the tissue to approximate the cuff or anchor ring on the tissue, then the staple is formed. The instrument is removed from the vicinity of a formed staple and is moved to the next groove. Once the anchor ring is stapled to the patient, the guide 830 is removed and the heart valve is located to be attached to the anchor ring as above described.

A more automated system for placing an anchor ring on a patient is illustrated in FIGS. 51–53. This system uses the above described instrument 849 and includes one system for locating the anchor ring and a second system for automatically indexing the location of the staple placement. Both system are shown in FIGS. 51 and 52.

The anchor ring is placed in the patient by first system 850 which includes two arcuate expander shoes 852 each pivotally connected at pivot 853 to an expander arm 854 at an arcuate section 856 of that arm located near the distal end of the arm. A pivot 857 is located on the distal end of each expander arm, and the proximal end of each arm is located outside the patient during use. The surgeon grasps each of the expander arms near the proximal ends 858 thereof and manipulates these arms to expand the anchor ring against the patient's tissue. An O-ring 860 exerts a radially inward bias that opposes outward movement of the expander shoes. Cuff liners, such as cuff liner 860 are interposed between the expander shoes and the O-ring and contact the anchor ring. Cuff liners 862 serve as an outer circumferential edge of the system 849.

System 849 further includes a top guide element 864. Element 864 includes a central section 866 and two wing sections 868. Central section 866 accommodates the top end of guide tube 870 through which instrument 800 fits to be guided into stapling position within the patient. A key hole slot 871 can engage a key 872 (see FIG. 46) on housing 806 of instrument 800 to further control placement of the instrument. As can be seen in FIG. 52, the bottom end of guide tube 870 is positioned adjacent to the cuff liners and is angled with respect to the plane established by the expander arms. The angled nature of the staple discharge section discussed above thus places the staples in the proper position for discharge through the anchor ring and through the patient's tissue to attach the anchor ring to the tissue. Each element 864 further includes a plurality of ratchet teeth 870 that engage the expander arms to hold them in a selected location and orientation.

The tool shown in FIG. 46 has only one set of drivers and thus the mechanical complexity is low enough to make manufacturing efficient. Additionally, since manufacturing small parts is difficult, and small parts do not handle stresses well, the reduction in parts for the FIG. 46 tool is advantageous. Use of the system shown in FIG. 46 is evident from the disclosure herein, and thus will only be briefly discussed. Once the diseased valve is removed and the tissue is decalcified, the valve base alignment ring is placed down into the aorta and is held in place with the stabilizing arms. Next, the surgeon looks down through the aorta at the cuff and uses the serrations on the inside of the ring to guide the staple driving tool toward the cuff. He then extends the legs of the staple beyond the distal end of the driving instrument and places the staple according to the icons on the cuff. He then pushes the staple legs through the cuff to penetrate the aortic tissue thereby approximating the cuff to the tissue. Subsequently, he forms the staple with the staple forming device and then removes the device. The device is then moved to the next serration, thereby stabilizing the top edge of the staple driving shaft and then places the protruding staple legs into the next printed icon. The process is continued until either a helical or circular staple pattern is established. The process is completed when at least two overlapping rows of staples are formed in the cuff.

Once the anchor ring is securely stapled in place, the cuff is released from its attachment to the expander by cutting sutures and the tool is removed. Docking sutures which were pulled up out of the body cavity during the staple forming procedure are then sewn into the heart valve cuff and the valve is lowered into place either within the circumference of the anchor ring or superiorly depending on the configuration of the heart valve prosthesis. Docking sutures can be in the form of individual pairs passing through the cuff or running sutures. Typically, there are three running sutures. Other docking procedures can be envisioned by those skilled in the art according to the teaching of this disclosure and are intended to be included within the scope of this disclosure. If the surgeon wants to adjust the superior/inferior placement he may do this by altering the placement of the docking sutures in the heart valve cuff.

The second element of the instrument 849 automatically indexes the location of the staple delivery. The second element includes a base 872 that is located within the cuff liner and includes a central internally threaded hole 874 and two pivot connections 876 to which pivots 857 of the expander arms are connected. The thread in hole 874 is helical for a purpose that will be discussed below. An idler plate 878 is mounted on base 872 by pivot pin 880 being inserted into hole 882 defined in base 872. An idler 884 is rotationally mounted on idler plate 878 and is engaged by index gear 886 that is also rotationally mounted on idler plate 878. An idler plate spring 888 is mounted at one end thereof on base 872 and at the other end thereof to idler plate 878 and is held in place on base 872 by flexible rack 900 mounted on cuff liner 862. Index gear 886 is connected to a distal end of index drive shaft 890, with the proximal end of shaft 890 being attached to an index wheel 892. Index wheel 892 is rotationally mounted to element 864 at a central location 894 having index indicators 896 thereon. Index drive shaft 890 is rotated by rotation of index wheel 892, with index indicators providing a visual indication of the amount of rotation undergone by the index drive shaft. As shown, rotation of index gear 886 in direction 897 causes corresponding rotation of idler 884 in direction 897'. Index gear 886 is engaged with flexible gear rack 900 which is held in place on the cuff liners. When the index wheel is moved in direction 897, the plate 872 follows in direction 897" since the flexible gear rack is stationary. Idler gear 884 is constructed of an elastomeric material and merely helps the rotation of the plate by turning against shaft 908. Flexible gear rack 900 is fixed to one cuff liner 860. Since alignment tube 870 is fixed to base 872, tube 870 will rotate with the base.

As shown in FIG. 53, heart valve HV is attached to cuff 19 and to heart valve base holder 902. Base holder 902 includes arms 904 radiating outwardly from central section 906 on which an externally threaded projection 908 is mounted. Thread groove 910 is helical and matingly engages thread 912 defined on base 876 adjacent to hole 874. A retainer and spring 914 ensures proper engagement between threads 908 and 912. Valve base holder 902 is released from the heart valve by operating release lever 916 connected to release shaft 918 to lift the shaft 918 upwardly. Lifting release shaft 918 causes fingers 904 to rotate inwardly to release the anchor ring from the holder 902. The anchor ring is firmly secured to the patient when the release lever is operated and the inwardly rotated arms are flexible enough to move past the fixed anchor ring.

It is noted that the anchor ring is fixed to the patient by the outward flexing of the arms 854, and an initial staple can be placed to further fix the anchor ring to the patient to begin the process. Thus, any item fixed to the anchor ring is fixed, and any other element will move with respect to the anchor ring after that ring is initially fixed to the patient. Thus, since the base 872 is not fixed to the anchor ring, it will rotate with respect to the anchor ring, while base holder 902 is fixed to the anchor ring. Thus, rotation of shaft 890 rotates the base 872 with respect to holder 902. Since holder 902 is threadably engaged with base 872, rotation of base 872 causes the base to move longitudinally on the holder 872. Thus, base 872 moves both rotationally and longitudinally on the cuff or anchor ring. The staple delivery location, being fixed to the base, thus moves both rotationally and longitudinally with respect to the cuff. Such simultaneous rotational and longitudinal movement causes the staple delivery location to describe a helical path on the fixed cuff. Such a helical path is shown in FIGS. 54A–54C, for various sizes of staples and various staple spacings (21 mm spacing in FIG. 54A, and 21.5 mm spacing in FIG. 54C). This helical path permits a single line of staples to be set without unwanted gaps and with any degree of overlap desired.

The system shown in FIG. 51 assures that each staple is placed with the proper spacing between staples and that the rows are properly spaced. In addition, this alignment procedure is very forgiving and is adjustable to aorta diameter. This is because staples can be spaced apart a linear distance instead of an arcuate distance. The staples are placed in a single continuous row which takes the form of a helix to complete overlapping multiple rows when the line is long enough to complete two or more revolutions of the helix. It additionally allows the second revolution of the line to be placed much closer to the first revolution because the line is not constrained by packaging multiple driver assemblies. The line distance is regulated only by how fine or coarse the helix angle is on the index mechanism.

Use of the FIG. 51 system is evident from the above disclosure and thus will only be summarized. The surgeon advances the staple in the tool to expose the straight legs of the staple, The straight legs of the staple are then pushed through the cuff to penetrate the aortic tissue.

Once the surgeon has felt the penetration of the staples into the tissue, he then forms the staple. Once the staple is formed and the lifter spring has lifted the staple off of the anvil, the staple driving tool is removed from the receptacle. While holding on to the proximal end of the tool, the index wheel is rotated one-half of a full rotation as indicted by colored markers on the index wheel as seen through the index wheel indicators. The staple driving tool is then again inserted into the staple alignment receptacle and keyed to maintain staple alignment. Once again, the staple legs are advanced forward and penetrated through the cuff and the annular aortic tissue, then the staple is fully formed. This process is repeated until two full rotations of the indexing base are accomplished, thus providing two overlapping helical rows of staples.

One form of the device has the timing wheel held within the indexing mechanism. The first step is to place the valve base and the cuff into the aorta with the index valve holder. The second step is to dilate the cuff and make it snug against the aorta by using the dilation control on the index valve holder. The internal platens, which press the cuff against the annulus expand. By expanding these platens, the indexing mechanism takes on the diameter of the distal section. This calibrates the indexing mechanism for the specific annulus size. An incremental movement of the index planetary gear will make certain that the receptacle has indexed the proper amount to ensure that the next staple is fired precisely one increment from the previous staple, independent of annulus size. As the index mechanism is shifted to the next position, the planetary gear ensures that the mechanism will place the receptacle one increment away. After the staple driving device has fired the first staple, the driving device is removed from the instrument and the index holder is indexed to the next position. If desired, the device can form two rows of staples by extending the index feature to an upper position after firing a first row of staples.

With regard to the index gear 886, it is noted that each one-half rotation thereof provide one staple increment. The index spring 998 on the base engages lugs on index gear 887 to signal the user when the index gear has made one-half of a revolution through an audible tactile "click." Further note that the flexible gear rack is connected at one end to one of four cuff liner parts and is allowed to float freely from thereon thereby allowing the index gear rack to expand as the expander arms push on the cuff liners to accommodate larger or smaller sizes of aorta. In addition, the gear rack is taller than the index gear in order to allow the index gear to continue to engage the index rack as the alignment tube plate rises up the threads to produce the helical pattern. It is also noted that the expander arms are made of a slippery polymer to reduce friction with the cuff liners. Each shoe, through a small dovetail, engages at least two cuff liners.

A further use of the instrument 800 is illustrated in FIGS. 55 and 56 for closing the aortomy 920. This procedure is achieved using staples alone. The surgeon approximates the incised edges of the aorta with forceps 922, and tool 800 is placed next to the approximated edges and operated to deploy a staple. Due to the dual movement of the staple discussed above, the legs of the staple move through the tissue before they are folded over. As they fold over, the edges are brought together so formed staple 720f closes the incision as shown in FIG. 56.

It is understood that while certain forms of the present invention have been illustrated and described herein, it is not to be limited to the specific forms or arrangements of parts described and shown with the elements being shown, such as the tool T, being the best mode, but not the only mode.

We claim:

1. A tool for placing a prosthesis in a patient in a minimally invasive manner comprising:
    A) a housing;
    B) an operating shaft associated with said housing and extending out of a patient's body during use;
    C) an operating handle mounted on a proximal end of said operating shaft;
    D) a means associated with said housing for delivering and forming at least one fastener to attach a sewing cuff of a prosthesis valve to a patient and including
        (1) an anvil located in position to engage and close a fastener when that fastener has been forced against said anvil, and
        (2) a driver element in position to engage a fastener and force that fastener against said anvil for closing the fastener; and
    E) means for releasably mounting the sewing cuff on said housing during operation of said means for delivering and forming at least one fastener.

2. A tool for placing a prosthesis in a patient during surgery comprising:
    A) a housing;
    B) a driver mechanism on said housing for driving and forming a first W-shaped fastener;
    C) a means on said housing for loading a second W-shaped fastener in the driver mechanism for driving and forming; and
    D) means on said housing for approximating a prosthesis against a patient while said fasteners are driven and formed to attach the prosthesis to the patient.

3. A tool for placing a prosthesis in a patient in a minimally invasive manner comprising:
    A) a housing;
    B) an operating handle connected to said housing;
    C) a means associated with said housing and controlled by said operating handle for delivering and forming at least one fastener to attach a prosthesis to a patient and including means for storing a plurality of fasteners, whereby fasteners are accommodated on a tool used to place the prosthesis in the patient, and including a stapler containing a plurality of W-shaped staples;
    D) means for releasably supporting a flexible cuff portion of the prosthesis while a fastener is being formed; and
    E) means for approximating said flexible sewing cuff against a patient while a fastener is being forced through said flexible sewing cuff and is being formed.

4. In combination:
    A) a prosthesis including
        (1) a prosthesis body,
        (2) an expandable flexible sewing cuff separate and spaceable from said prosthesis body, and
        (3) means for securely attaching said prosthesis body to said flexible sewing cuff after said flexible sewing cuff has been attached to a patient; and
    B) a tool system for placing said prosthesis in the patient in a minimally invasive manner including
        (1) a housing,
        (2) an operating handle connected to said housing,
        (3) means associated with said housing and controlled by said operating handle for delivering and forming at least one fastener to attach said flexible sewing cuff to the patient and including means for storing a plurality of fasteners which are used for attaching said flexible sewing cuff to the patient whereby fasteners are accommodated on said tool,
        (4) means for supporting said flexible sewing cuff while a fastener is being formed, and
        (5) means for expanding and approximating said flexible sewing cuff against the patient while a fastener is being forced through said flexible sewing cuff and into the patient's tissue and is being formed to attach said flexible sewing cuff to the patient.

5. In combination:
    A) a multiple part prosthesis which includes
        (1) a prosthesis body,
        (2) an expandable flexible sewing cuff separate and spaceable from said prosthesis body, and
        (3) means for securely attaching said prosthesis body to said flexible sewing cuff after said flexible sewing cuff has been attached to a patient; and
    B) a tool system for placing said prosthesis in the patient in a minimally invasive manner including (1) a housing,
(2) an operating handle,
(3) means associated with said housing and controlled by said operating handle for delivering and forming a fastener to attach one part of said multiple part prosthesis to the patient,
(4) means for storing fasteners on said tool,
(5) means for releasably supporting said flexible sewing cuff while the fastener is being formed, and
(6) means for expanding and approximating said flexible sewing cuff against the patient while the fastener is being formed.

6. In combination:
A) a prosthesis including
   (1) a prosthesis body,
   (2) an expandable flexible sewing cuff separate and spaceable from said prosthesis body, and
   (3) means for securely attaching said prosthesis body to said flexible sewing cuff after said flexible sewing cuff has been attached to a patient; and
B) a tool system for placing said prosthesis in the patient in a minimally invasive manner including
   (1) a housing,
   (2) an operating shaft,
   (3) a mechanism on said housing for delivering and forming a fastener and including means for storing a plurality of fasteners during operation of said fastener delivery and forming mechanism to attach said prosthesis to a patient,
   (4) means on said housing and connected to said operating shaft for actuating said fastener delivery and forming mechanism,
   (5) means for releasably supporting said flexible sewing cuff of said prosthesis while fasteners are being formed, and
   (6) means for expanding and releasably approximating said flexible sewing cuff against the patient while fasteners are being penetrated through said flexible sewing cuff of the prosthesis and are being formed to attach said flexible sewing cuff to the patient.

7. In combination:
A) a prosthesis including
   (1) a prosthesis body,
   (2) an expandable flexible sewing cuff separate and spaceable from said prosthesis body, and
   (3) means for securely attaching said prosthesis body to said flexible sewing cuff after said flexible sewing cuff has been attached to a patient; and
B) a tool system for placing said prosthesis in the patient in a minimally invasive manner including
   (1) a housing,
   (2) a plurality of tissue penetrating fasteners stored in said housing,
   (3) an operating shaft,
   (4) a fastener delivery and forming mechanism on said housing for delivering and forming a tissue-penetrating fastener and including means for storing tissue-penetrating fasteners during operation of said fastener delivery and forming mechanism to attach the flexible sewing cuff to the patient,
   (5) means on said housing and connected to said operating shaft for actuating said fastener delivery and forming mechanism,
   (6) means for releasably supporting said flexible sewing cuff of the prosthesis while fasteners are being formed, and
   (7) means for expanding and releasably approximating said flexible sewing cuff of the prosthesis against a patient while fasteners are being formed.

8. In combination:
A) a prosthesis including
   (1) a prosthesis body,
   (2) an expandable flexible sewing cuff separate and spaceable from said prosthesis body, and
   (3) means for securely attaching said prosthesis body to said flexible sewing cuff after said flexible sewing cuff has been attached to a patient; and
B) a tool system for placing said prosthesis in the patient in a minimally invasive manner including
   (1) a housing,
   (2) an operating handle connected to said housing,
   (3) a means associated with said housing and controlled by said operating handle for delivering and forming at least one fastener to attach said flexible sewing cuff to the patient and including means for storing a plurality of fasteners, whereby fasteners are accommodated on the tool used to place the flexible sewing cuff in the patient,
   (4) means for releasably supporting said flexible sewing cuff of said prosthesis while a fastener is being formed,
   (5) means for expanding and approximating said flexible sewing cuff against the patient while a fastener is being forced through a portion of said flexible sewing cuff and is being formed; and
   (6) means on said means for delivering and forming at least one fastener for releasably holding the portion of said flexible sewing cuff against the patient.

9. In combination:
A) a multiple part prosthesis including
   (1) a prosthesis body, said prosthesis body including a valve,
   (2) an expandable flexible sewing cuff separate and spaceable from said prosthesis body, and
   (3) means for securely attaching said prosthesis body to said flexible sewing cuff after said flexible sewing cuff has been attached to a patient; and
B) a tool system for placing said prosthesis in the patient in a minimally invasive manner including
   (1) a housing,
   (2) an operating handle,
   (3) a means associated with said housing and controlled by said operating handle for delivering and forming a fastener to attach one part of said multiple part prosthesis to the patient whereby fasteners are accommodated on the tool used to place the flexible sewing cuff of the prosthesis in the patient and including means for storing a plurality of fasteners,
   (4) means for releasably supporting said flexible sewing cuff while a fastener is being formed, and
   (5) means for expanding and approximating said flexible sewing cuff of the multipart prosthesis against the patient while the fastener is being formed.

10. In combination:
A) a prosthesis including
   (1) a prosthesis body,
   (2) an expandable flexible sewing cuff separate and spaceable from said prosthesis body, and
   (3) means for securely attaching said prosthesis body to said flexible sewing cuff after said flexible sewing cuff has been attached to a patient; and
B) a tool system for placing said prosthesis in the patient in a minimally invasive manner including
   (1) a housing,
   (2) an operating handle connected to said housing, (3) a means associated with said housing and controlled by said operating handle for delivering and forming at least one fastener to attach said flexible sewing cuff of the prosthesis to the patient and including means for storing a plurality of fasteners, whereby fasteners are accommodated on the tool used to place the sewing cuff in the patient, said fastener delivering and forming means including a plurality of arcuately spaced apart fastener delivery locations thereon, (4) means for releasably supporting said flexible sewing cuff of the prosthesis while a fastener is being formed, (5) means for expanding and approximating said flexible sewing cuff against the patient while a fastener is being forced through a portion of said flexible sewing cuff and is being formed, and (6) a pre-fire rod means for extending tips of the fasteners through said flexible sewing cuff into the patient's tissue prior to forming the fasteners to attach the flexible sewing cuff of the prosthesis to the patient.

11. In combination:

A) a prosthesis which includes a sewing cuff which is flexible, expandable and deformable to fit the size and shape of a patient's tissue during installation of said flexible sewing cuff in the patient; and B) a tool system for placing said prosthesis in the patient in a minimally invasive manner including
 (1) a housing,
 (2) an operating handle connected to said housing,
 (3) a means associated with said housing and controlled by said operating handle for delivering and forming at least one fastener to attach a prosthesis to a patient and including means for storing a plurality of fasteners, whereby fasteners are accommodated on the tool used to place the flexible sewing cuff in the patient,
 (4) means for releasably supporting said flexible sewing cuff of said prosthesis while a fastener is being formed, and
 (5) expander arms for approximating a portion of said sewing cuff against the patient while a fastener is being forced through said flexible sewing cuff and is being formed.

12. In combination:

A) a prosthesis including
 (1) a prosthesis body,
 (2) an expandable flexible sewing cuff separate and spaceable from said prosthesis body, and
 (3) drawstrings which securely attach said prosthesis body to said flexible sewing cuff after said flexible sewing cuff has been attached to a patient; and B) a tool system including
 (1) a housing,
 (2) an operating handle connected to said housing,
 (3) a driver and anvil associated with said housing and controlled by said operating handle which deliver and form at least one fastener to attach said flexible sewing cuff to the patient and including a storage pocket which stores a plurality of fasteners which are used for attaching said flexible sewing cuff to the patient whereby fasteners are accommodated on said tool,
 (4) an anchor which supports said flexible sewing cuff while a fastener is being formed, and
 (5) expander arms positioned to engage the inside of said flexible sewing cuff and urge said flexible sewing cuff against the patient's tissue while a fastener is being forced through said flexible sewing cuff and into the patient's tissue and is being formed to attach said flexible sewing cuff to the patient.

13. In combination:

A) a multiple part prosthesis which includes
 (1) a prosthesis body,
 (2) an expandable flexible sewing cuff separate and spaceable from said prosthesis body, and
 (3) drawstrings which securely attach said prosthesis body to said flexible sewing cuff after said flexible sewing cuff has been attached to a patient; and B) a tool system including
 (1) a housing,
 (2) an operating handle,
 (3) an anvil and driver associated with said housing and controlled by said operating handle and which deliver and form a fastener to attach one part of said multiple part prosthesis to the patient,
 (4) a storage pocket which stores fasteners on said tool,
 (5) an anchor which releasably supports said flexible sewing cuff while the fastener is being formed, and
 (6) expander arms which expand and approximate said flexible sewing cuff against the patient while the fastener is being formed.

14. In combination:

A) a prosthesis including
 (1) a prosthesis body,
 (2) an expandable flexible sewing cuff separate and spaceable from said prosthesis body, and
 (3) drawstrings which securely attach said prosthesis body to said flexible sewing cuff after said flexible sewing cuff has been attached to a patient; and B) a tool system including
 (1) a housing,
 (2) an operating shaft,
 (3) a driver and anvil on said housing which delivers and forms a fastener and including a storage pocket in which a plurality of fasteners are stored during operation of said driver and anvil and which attaches said flexible sewing cuff of said prosthesis to the patient,
 (4) an anchor which releasably supports said flexible sewing cuff of said prosthesis while fasteners are being formed, and
 (5) engaging arms which engage said flexible sewing cuff and expand and approximate said flexible sewing cuff against the patient while fasteners are being penetrated through said flexible sewing cuff of the prosthesis and are being formed to attach said flexible sewing cuff to the patient.

15. In combination:

A) a prosthesis including
 (1) a prosthesis body,
 (2) an expandable flexible sewing cuff separate and spaceable from said prosthesis body, and
 (3) drawstrings which securely attach said prosthesis body to said flexible sewing cuff after said flexible sewing cuff has been attached to a patient; and B) a tool system including
 (1) a housing,
 (2) a plurality of tissue penetrating fasteners stored in said housing,
 (3) an operating shaft,
 (4) an anvil and driver on said housing which deliver and form a tissue-penetrating fastener and including a storage pocket in which is stored tissue-penetrating fasteners during operation of said anvil and driver to attach said sewing cuff to the patient, (5) anchors which releasably support said flexible sewing cuff of the prosthesis while fasteners are being formed, and (6) engaging arms which expand and approximate said flexible sewing cuff of the prosthesis against a patient while fasteners are being formed.

16. In combination:

A) a prosthesis including
  (1) a prosthesis body,
  (2) an expandable flexible sewing cuff separate and spaceable from said prosthesis body, and
  (3) drawstrings which securely attach said prosthesis body to said flexible sewing cuff after said flexible sewing cuff has been attached to a patient; and B) a tool system including
  (1) a housing,
  (2) an operating handle connected to said housing,
  (3) an anvil and driver associated with said housing and controlled by said operating handle which deliver and form at least one fastener to attach said flexible sewing cuff of said prosthesis to the patient and including a pocket in which a plurality of fasteners are stored, whereby fasteners are accommodated on the tool used to place the flexible sewing cuff in the patient,
  (4) anchors which releasably supports said flexible sewing cuff of said prosthesis while the fastener is being formed, and
  (5) engaging arms which expand and approximate the flexible sewing cuff against the patient while a fastener is being forced through a portion of said flexible sewing cuff and is being formed.

17. In combination:

A) a multiple part prosthesis including
  (1) a prosthesis body, said prosthesis body including a valve,
  (2) an expandable flexible sewing cuff separate and spaceable from said prosthesis body, and
  (3) drawstrings which securely attach said prosthesis body to said flexible sewing cuff after said flexible sewing cuff has been attached to a patient; and B) a tool system including
  (1) a housing,
  (2) an operating handle,
  (3) an anvil and driver associated with said housing and controlled by said operating handle and which deliver and form a fastener to attach one part of said multiple part prosthesis to the patient whereby fasteners are accommodated on the tool used to place the flexible sewing cuff of the prosthesis in the patient and including a pocket in which a plurality of fasteners are stored,
  (4) an anchor which releasably supports said flexible sewing cuff while a fastener is being formed, and
  (5) engaging arms which expand and approximate said flexible sewing cuff of the multipart prosthesis against the patient while the fastener is being formed.

18. In combination:

A) a prosthesis including
  (1) a prosthesis body,
  (2) an expandable flexible sewing cuff separate and spaceable from said prosthesis body, and
  (3) drawstrings which securely attach said prosthesis body to said flexible sewing cuff after said flexible sewing cuff has been attached to a patient; and B) a tool system including
  (1) housing,
  (2) an operating handle connected to said housing,
  (3) a an anvil and driver associated with said housing and controlled by said operating handle and which deliver and form at least one fastener to attach said flexible sewing cuff of the prosthesis to the patient and including a pocket in which a plurality of fasteners are stored whereby fasteners are accommodated on the tool used to place the sewing cuff in the patient, said anvil and driver including a plurality of arcuately spaced apart fastener delivery locations thereon,
  (4) an anchor which releasably supports said flexible sewing cuff of the prosthesis while a fastener is being formed,
  (5) engaging arms which approximate said flexible sewing cuff against the patient while the fastener is being forced through a portion of said flexible sewing cuff and is being formed, and
  (6) a pre-fire rod which extends tips of the fasteners through said flexible sewing cuff into the patient's tissue prior to forming the fasteners to attach the flexible sewing cuff of the prosthesis to the patient.

19. In combination:

A) a prosthesis which includes a sewing cuff which is flexible and deformable to fit the size and shape of a patient's tissue during installation of said flexible sewing cuff in the patient; and B) a tool system including
  (1) a housing,
  (2) an operating handle connected to said housing,
  (3) an anvil and driver associated with said housing and controlled by said operating handle and which delivers and forms at least one fastener to attach said flexible sewing cuff to the patient and including a pocket in which a plurality of fasteners are stored, whereby fasteners are accommodated on the tool used to place the flexible sewing cuff in the patient,
  (4) an anchor which releasably supports said flexible sewing cuff of said prosthesis while a fastener is being formed, and
  (5) expander arms which approximate a portion of said flexible sewing cuff against the patient while a fastener is being forced through said flexible sewing cuff and is being formed.

20. The tool defined in claim 1 further including a plurality of means for operating said fastener handling means.

21. The tool defined in claim 20 further including a plurality of anvils on said mechanism.

22. The tool defined in claim 21 further including a plurality of driver elements on said mechanism.

23. The tool defined in claim 21 wherein said plurality of anvils are in staggered relationship with each other.

24. The tool defined in claim 1 further including means for controlling the position of a fastener on said means for accommodating fasteners.

25. The tool defined in claim 1 wherein said fastener is W-shaped.

26. The tool defined in claim 1 further including means for ejecting a fastener from said fastener handling means.

27. The tool defined in claim 1 further including means for storing a plurality of fasteners in said fastener handling means.

28. The tool defined in claim 27 wherein said fasteners are located in a plurality of rows.

29. The tool defined in claim 1 wherein said means on another end of said operating shaft for operating said fastener handling means includes a cam.

30. The tool defined in claim 1 wherein said fastener handling means further includes a linkage means for linking said means on another end of said operating shaft for operating said fastener handling means and said operating knob.

31. The tool defined in claim 1 wherein said operating shaft is flexible.

32. The tool defined in claim 1 further including an indexing means for controlling location of said means for storing, delivering and forming a fastener.

33. The tool defined in claim 29 further including a plurality.

34. The tool defined in claim 28 wherein the fasteners in one row are staggered with respect to the fasteners in an adjacent row.

35. The tool defined in claim 1 further including means for releasably mounting a prosthetic valve body on the tool.

36. The tool defined in claim 1 wherein said means on said housing for forcing the sewing cuff against the patient's tissue as said fastener handling means is operated includes a biasing element.

37. The tool defined in claim 1 wherein said anvil is located to close a fastener after that fastener has penetrated the sewing cuff and the patient's tissue.

38. The tool defined in claim 28 wherein the fasteners of said plurality of fasteners are angularly spaced apart from each other.

39. The tool defined in claim 1 further including means for rotating said means for storing, delivering and forming a fastener about an axis extending through said operating shaft.

40. The tool defined in claim 1 further including means for rotating said means for accommodating fasteners about an axis extending through said operating shaft.

41. The tool defined in claim 1 further including means for forcing the sewing cuff against the patient's tissue as said fastener handling means is operated.

42. The combination defined in claim 4 in which said tool system further includes means for separating the tool system from the prosthesis.

43. The tool defined in claim 1 further including means for rotating said fastener handling means about an axis through said housing.

44. The tool defined in claim 1 further including means for rotating said fastener handling means about an axis through said sewing cuff.

45. The tool defined in claim 25 wherein said fastener includes two legs and a crown connecting said legs together, with said legs being linear and said crown being arcuate.

46. The tool defined in claim 45 further including means for supporting said legs and wherein said crown is located between said anvil and said driver element so that said forcing said crown against said anvil causes said legs to rotate toward each other.

47. The combination defined in claim 4 wherein said fastener delivery and forming means further includes a plurality of fastener delivery locations.

48. The combination defined in claim 47 wherein said fastener delivery locations are arcuately spaced apart from each other.

49. The combination defined in claim 48 further including additional fastener delivery locations which are spaced apart from the first mentioned fastener delivery locations longitudinally of said fastener delivery mechanism.

50. The combination defined in claim 48 further including a pre-fire rod means for extending tips of the fasteners through the prosthesis into the patient's tissue prior to forming the fasteners.

51. The combination defined in claim 47 further including a plurality of wedge cam means for forming fasteners.

52. The combination defined in claim 48 further including means for returning said fastener delivery means to an initial position.

53. The combination defined in claim 48 wherein said fastener delivery means includes a wedge cam alignment block.

54. The combination defined in claim 53 wherein said wedge cam alignment block includes a plurality of slots.

55. The combination defined in claim 48 further including indexing means on said means for supporting said flexible cuff.

56. The combination defined in claim 4 wherein said fastener delivery means includes expander arms.

57. The combination defined in claim 56 wherein said expander arms include expander shoes thereon.

58. The combination defined in claim 57 wherein said expander arms further include ratchet engagement means for maintaining expansion force exerted by said expander arms on the prosthesis.

59. The combination defined in claim 56 further including a means for indexing the means for storing, delivering and forming a fastener between positions.

60. The combination defined in claim 59 further including an index transmission means for connecting an index input element to an index output element.

61. The combination defined in claim 60 wherein said output element includes an increment means for moving said means for storing, delivering and forming a fastener relative to the prosthesis in response to movement of said said input element.

62. The combination defined in claim 56 further including means for releasing the prosthesis from the tool.

63. The combination defined in claim 56 further including a guide tube on the tool.

64. The combination defined in claim 4 wherein said means associated with said housing further includes a stapler containing a plurality of W-shaped staples.

65. The combination defined in claim 56 wherein said fastener handling means includes means for moving it in a helical path with respect to the prosthesis.

66. The combination defined in claim 56 wherein said means associated with said housing includes means for moving it in a single continuous curvilinear path with respect to the flexible sewing cuff of said prosthesis.

67. The combination defined in claim 4 further including staple-pattern defining icons on the prosthesis.

68. The combination defined in claim 4 further including means for delivering staples at an acute angle with respect to the longitudinal centerline of said fastener handling means.

69. The combination defined in claim 4 further including flexible arms on said means for approximating said flexible sewing cuff against the patient.

70. The combination defined in claim 61 further including means for signalling a user when said index gear has moved through a predetermined angle.

71. The combination defined in claim 5 tool wherein said multipart prosthesis includes a valve.

72. The tool defined in claim 2 wherein the means for placing a prosthesis includes means for indexing the means for placing a prosthesis.

73. The combination defined in claim 4 wherein said means for securely attaching the prosthesis body to said flexible sewing cuff includes extensions that extend outside the patient.

74. The combination defined in claim 5 wherein said means for securely attaching the prosthesis body to said flexible sewing cuff includes extensions that extend outside the patient.

75. The combination defined in claim 6 wherein said means for securely attaching the prosthesis body to said flexible sewing cuff includes extensions that extend outside the patient.

76. The combination defined in claim 7 wherein said means for securely attaching the prosthesis body to said flexible sewing cuff includes extensions that extend outside the patient.

77. The combination defined in claim 8 wherein said means for securely attaching the prosthesis body to said flexible sewing cuff includes extensions that extend outside the patient.

78. The combination defined in claim 9 wherein said means for securely attaching the prosthesis body to said flexible sewing cuff includes extensions that extend outside the patient.

79. The combination defined in claim 10 wherein said means for securely attaching the prosthesis body to said flexible sewing cuff includes extensions that extend outside the patient.

80. The combination defined in claim 11 wherein said means for securely attaching the prosthesis body to said flexible sewing cuff includes extensions that extend outside the patient, patient.

81. The combination defined in claim 12 in which said drawstrings include extensions that extends out of the patient during installation of said flexible sewing cuff in the patient.

82. The combination defined in claim 13 in which said drawstrings include extensions that extends out of the patient during installation of said flexible sewing cuff in the patient.

83. The combination defined in claim 14 in which said drawstrings include extensions that extends out of the patient during installation of said flexible sewing cuff in the patient.

84. The combination defined in claim 15 in which said drawstrings include extensions that extends out of the patient during installation of said flexible sewing cuff in the patient.

85. The combination defined in claim 16 in which said drawstrings include extensions that extends out of the patient during installation of said flexible sewing cuff in the patient.

86. The combination defined in claim 17 in which said drawstrings include extensions that extends out of the patient during installation of said flexible sewing cuff in the patient.

87. The combination defined in claim 18 in which said drawstrings include extensions that extends out of the patient during installation of said flexible sewing cuff in the patient.

88. The combination defined in claim 19 in which said prosthesis further includes a prosthesis body and drawstrings which connect said body to said flexible sewing cuff, wherein said drawstrings include extensions that extends out of the patient during installation of said flexible sewing cuff in the patient.

89. The combination defined in claim 4 wherein said means for expanding and approximating said flexible sewing cuff extends radially outward from said housing.

90. The combination defined in claim 5 wherein said means for expanding and approximating said flexible sewing cuff extends radially outward from said housing.

91. The combination defined in claim 6 wherein said means for expanding and approximating said flexible sewing cuff extends radially outward from said housing.

92. The combination defined in claim 7 wherein said means for expanding and approximating said flexible sewing cuff extends radially outward from said housing.

93. The combination defined in claim 8 wherein said means for expanding and approximating said flexible sewing cuff extends radially outward from said housing.

94. The combination defined in claim 9 wherein said means for expanding and approximating said flexible sewing cuff extends radially outward from said housing.

95. The combination defined in claim 10 wherein said means for expanding and approximating said flexible sewing cuff extends radially outward from said housing.

96. The combination defined in claim 11 wherein said expander arms extend radially outward from said housing.

97. The combination defined in claim 12 wherein said expander arms extend radially outward from said housing.

98. The combination defined in claim 13 wherein said expander arms extend radially outward from said housing.

99. The combination defined in claim 14 wherein said engaging arms extend radially outward from said housing.

100. The combination defined in claim 15 wherein said engaging arms extend radially outward from said housing.

101. The combination defined in claim 16 wherein said engaging arms extend radially outward from said housing.

102. The combination defined in claim 17 wherein said engaging arms extend radially outward from said housing.

103. The combination defined in claim 18 wherein said engaging arms extend radially outward from said housing.

104. The combination defined in claim 19 wherein said expander arms extend radially outward from said housing.

* * * * *